US011918645B2

(12) United States Patent
Georges et al.

(10) Patent No.: US 11,918,645 B2
(45) Date of Patent: *Mar. 5, 2024

(54) VACCINES AGAINST HEPATITIS B VIRUS

(71) Applicant: Altimmune UK Ltd., Leeds (GB)

(72) Inventors: Bertrand Victor Gilbert Georges, London (GB); Carlton Bradley Brown, Santa Cruz la laguna (GT)

(73) Assignee: Altimmune UK Limited, Leeds (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/861,189

(22) Filed: Jul. 9, 2022

(65) Prior Publication Data

US 2023/0090379 A1 Mar. 23, 2023

Related U.S. Application Data

(60) Continuation of application No. 16/423,149, filed on May 27, 2019, now Pat. No. 11,382,969, which is a division of application No. 14/655,041, filed as application No. PCT/GB2013/053410 on Dec. 20, 2013, now Pat. No. 10,300,132.

(30) Foreign Application Priority Data

Dec. 24, 2012 (GB) ..................................... 1223386

(51) Int. Cl.
| | |
|---|---|
| *A61K 39/29* | (2006.01) |
| *A61K 39/12* | (2006.01) |
| *A61K 45/06* | (2006.01) |
| *C07K 14/005* | (2006.01) |
| *C12N 7/00* | (2006.01) |
| *A61K 39/00* | (2006.01) |

(52) U.S. Cl.
CPC ............ *A61K 39/292* (2013.01); *A61K 39/12* (2013.01); *A61K 45/06* (2013.01); *C07K 14/005* (2013.01); *C12N 7/00* (2013.01); *A61K 2039/55* (2013.01); *A61K 2039/572* (2013.01); *A61K 2039/58* (2013.01); *A61K 2039/60* (2013.01); *A61K 2039/70* (2013.01); *C12N 2730/10122* (2013.01); *C12N 2730/10134* (2013.01); *C12N 2730/10171* (2013.01)

(58) Field of Classification Search
None
See application file for complete search history.

(56) References Cited

U.S. PATENT DOCUMENTS

| | | | | |
|---|---|---|---|---|
| 6,607,727 | B1 * | 8/2003 | Chisari ................ | C07K 14/005 514/21.3 |
| 9,119,811 | B2 | 9/2015 | Brown et al. | |
| 10,300,132 | B2 * | 5/2019 | Georges ................ | A61P 31/14 |
| 11,382,969 | B2 * | 7/2022 | Georges ................ | A61P 1/16 |
| 2007/0059799 | A1 | 3/2007 | Sette et al. | |

| | | | |
|---|---|---|---|
| 2010/0183650 | A1 | 7/2010 | Bonnet et al. |
| 2012/0034259 | A1 | 2/2012 | Bonnet et al. |
| 2012/0251569 | A1 | 10/2012 | Martin et al. |
| 2012/0315293 | A1 | 12/2012 | Bonnet et al. |
| 2013/0330382 | A1 | 12/2013 | Brown et al. |
| 2015/0112042 | A1 | 4/2015 | Bonnet et al. |
| 2016/0051661 | A1 | 2/2016 | Brown et al. |

FOREIGN PATENT DOCUMENTS

| | | | |
|---|---|---|---|
| WO | 9303753 | A1 | 3/1993 |
| WO | 1993003753 | A1 | 3/1993 |
| WO | 9503777 | A1 | 2/1995 |
| WO | 1995003777 | A1 | 2/1995 |
| WO | WO 95/03777 | * | 2/1995 |
| WO | 0219986 | A1 | 3/2002 |
| WO | 2002019986 | A1 | 3/2002 |
| WO | 2005099752 | A2 | 10/2005 |
| WO | 2012090002 | A1 | 7/2012 |

OTHER PUBLICATIONS

Bijker, et al., "CD8+ CTL Priming by Exact Peptide Epitopes in Incomplete Freund's Adjuvant Induces a Vanishing CTL Response, whereas Long Peptides Induce Sustained CTL Reactivity" J. Immunol., Oct. 15, 2007;179 (8):5033-5040.

Cao, et al. "Characterization of HLA DR1 3-restricted CD4+ T cell epitopes of hepatitis B core antigen associated with self-limited, acute hepatitis B" Journal of General Virology, 2002, 83(Pt 12):3023-3033.

Castelli, F.A., et al., HLA-DP4, the most frequent HLA II molecule, defines a new supertype of peptide-binding specificity, J Immunology, 2002;169(12):6928-6934.

Database UniProt [Online], "Subname: Full=Precore/core protein;" retrieved from EBI accession No. Uniprot: Q9DH31, Mar. 2001.

Greenbaum, J., et al., Functional classification of class II human leukocyte antigen (HLA) molecules reveals seven different supertypes and a surprising degree of repertoire sharing across supertypes, Immunogenetics, 2011;63 (6):325-335.

Heiny, A.T., et al., Evolutionarily Conserved Protein Sequences of Influenza A Viruses, Avian and Human, as Vaccine Targets, Plos One, 2007; 2(11): p. e1190.

(Continued)

*Primary Examiner* — Shanon A. Foley
*Assistant Examiner* — Myron G Hill
(74) *Attorney, Agent, or Firm* — Koren Anderson; Duane Morris LLP

(57) ABSTRACT

A pharmaceutical composition comprising at least two peptides of from 15 to 60 amino acids in length, selected from peptides comprising a sequence of at least 15 contiguous amino acids of one of the sequences shown in SEQ ID NOs: 1 to 4 or of a sequence having at least 80% identity to one of the sequences shown in SEQ ID NOs: to 4, wherein each peptide comprises at least one CD8+ T-cell epitope and/or at least one CD4+ T-cell epitope and wherein each peptide elicits a response in peripheral blood mononuclear cells (PBMC) from at least one chronically infected HBV individual in an 10 in vitroassay.

18 Claims, 15 Drawing Sheets
Specification includes a Sequence Listing.

(56) References Cited

OTHER PUBLICATIONS

International Preliminary Report on Patentability and Written Opinion of the International Searching Authority dated Jun. 30, 2015, which issued during prosecution of International Application No. PCT/GB2013/053410.

International Search Report dated Jun. 3, 2014, which issued during prosecution of International Application No. PCT/GB2013/053410.

Khan, A.M., et al., Conservation and variability of dengue virus proteings: implications for vaccine design, PLOS Negl Trop Dis, 2008; 2(8): p. e272.

Krafft, MP., et al., Highly fluorinated amphiphiles and colloidal systems, and their applications in the biomedical field. A contribution, 1998, Biochimie vol. 80, pp. 489-514.

Lund, O., et al., Definition of supertypes for HLA molecules using clustering of specificity matrices, Immunogenetics, 2004;55(12):797-810.

Sette, A., et al., Nine major HLA class I supertypes account for the vast preponderance of HLA-A and -B polymorphism, Immunogenetics, 1999;50(3-4):201-212.

Texier, C., et al., Complementarity and redundancy of the binding specificity of HLA-DRB1, -DRB3, -DRB4 and -DRB5 molecules, European Journal of Immunology, 2001;31(6):1837-1846.

Texier, C., et al., HLA-DR restricted peptide candidates for bee venom immunotherapy, Journal of Immunology, 2000;164(6):3177-3184.

Wilson, C.C., et al., Identification and antigenicity of broadly cross-reactive and conserved human immunodeficiency virus type 1-derived helper T-lymphocyte epitopes, J Virology, 2001;75(9):4195-4207.

Zhang, G.L., et al., Hotspot Hunter: a computational system for large-scale screening and selection of candidate immunological hotspots in pathogen proteomes, BMC Bioinformatics, 2008; 9(Suppl 1):S19.

\* cited by examiner

```
                        SEQUENCE LISTING

Sequence total quantity: 222
SEQ ID NO: 1              moltype = AA  length = 94
FEATURE                   Location/Qualifiers
REGION                    1..94
                          note = HBV CONSENSUS SEQUENCE
source                    1..94
                          mol_type = protein
                          organism = synthetic construct
SEQUENCE: 1
QQFVGPLTVN EKRRLKLIMP ARFYPNVTKY LPLDKGIKPY YPEHVVNHYF QTRHYLHTLW   60
KAGILYKRET TRSASFCGSP YSWEQELQSC WWLQ                               94

SEQ ID NO: 2              moltype = AA  length = 216
FEATURE                   Location/Qualifiers
REGION                    1..216
                          note = HBV CONSENSUS SEQUENCE
SITE                      183
                          note = MISC_FEATURE - C OR S
source                    1..216
                          mol_type = protein
                          organism = synthetic construct
SEQUENCE: 2
CTEHGEHHIR IPRTPARVTG GVFLVDKNPH NTTESRLVVD FSQFSRGNTR VSWPKFAVPN   60
LQSLTNLLSS NLSWLSLDVS AAFYHIPLHP AAMPHLLVGS SGLSRYVARL SSNSRIINNQ  120
HGTMQNLHDS CSRNLYVSLM LLYKTYGRKL HLYSHPIILG FRKIPMGVGL SPFLLAQFTS  180
AIXSVVRRAF PHCLAFSYMD DVVLGAKSVQ HLESLY                            216

SEQ ID NO: 3              moltype = AA  length = 109
FEATURE                   Location/Qualifiers
REGION                    1..109
                          note = HBV CONSENSUS SEQUENCE
source                    1..109
                          mol_type = protein
                          organism = synthetic construct
SEQUENCE: 3
ACFARSRSGA KLIGTDNSVV LSRKYTSFPW LLGCAANWIL RGTSFVYVPS ALNPADDPSR   60
GRLGLYRPLL RLPFRPTTGR TSLYAVSPSV PSHLPDRVHF ASPLHVAWR              109

SEQ ID NO: 4              moltype = AA  length = 210
FEATURE                   Location/Qualifiers
REGION                    1..210
                          note = HBV CONSENSUS SEQUENCE
SITE                      41
                          note = MISC_FEATURE - S OR T
```

```
SITE                        90
                            note = MISC_FEATURE - C OR S
source                      1..210
                            mol_type = protein
                            organism = synthetic construct
SEQUENCE: 4
MQLFHLCLII SCSCPTVQAS KLCLGWLWGM DIDPYKEFGA XVELLSFLPS DFFPSVRDLL    60
DTASALYREA LESPEHCSPH HTALRQAILX WGELMTLATW VGSNLEDPAS RDLVVSYVNT   120
NMGLKIRQLL WFHISCLTFG RETVLEYLVS FGVWIRTPPA YRPPNAPILS TLPETTVVRR   180
RGRSPRRRTP SPRRRRSQSP RRRRSQSRES                                   210

SEQ ID NO: 5                moltype = AA   length = 53
FEATURE                     Location/Qualifiers
REGION                      1..53
                            note = HBV CONSENSUS SEQUENCE
source                      1..53
                            mol_type = protein
                            organism = synthetic construct
SEQUENCE: 5
QQFVGPLTVN EKRRLKLIMP ARFYPNVTKY LPLDKGIKPY YPEHVVNHYF QTR           53

SEQ ID NO: 6                moltype = AA   length = 54
FEATURE                     Location/Qualifiers
REGION                      1..54
                            note = HBV CONSENSUS SEQUENCE
source                      1..54
                            mol_type = protein
                            organism = synthetic construct
SEQUENCE: 6
YPEHVVNHYF QTRHYLHTLW KAGILYKRET TRSASFCGSP YSWEQELQSC WWLQ          54

SEQ ID NO: 7                moltype = AA   length = 67
FEATURE                     Location/Qualifiers
REGION                      1..67
                            note = HBV CONSENSUS SEQUENCE
source                      1..67
                            mol_type = protein
                            organism = synthetic construct
SEQUENCE: 7
RVSWPKFAVP NLQSLTNLLS SNLSWLSLDV SAAFYHIPLH PAAMPHLLVG SSGLSRYVAR    60
LSSNSRI                                                             67

SEQ ID NO: 8                moltype = AA   length = 53
FEATURE                     Location/Qualifiers
REGION                      1..53
                            note = HBV CONSENSUS SEQUENCE
source                      1..53
                            mol_type = protein
                            organism = synthetic construct
SEQUENCE: 8
GTMQNLHDSC SRNLYVSLML LYKTYGRKLH LYSHPIILGF RKIPMGVGLS PFL           53

SEQ ID NO: 9                moltype = AA   length = 95
FEATURE                     Location/Qualifiers
REGION                      1..95
                            note = HBV CONSENSUS SEQUENCE
SITE                        62
                            note = MISC_FEATURE - C OR S
source                      1..95
                            mol_type = protein
                            organism = synthetic construct
SEQUENCE: 9
GTMQNLHDSC SRNLYVSLML LYKTYGRKLH LYSHPIILGF RKIPMGVGLS PFLLAQFTSA    60
IXSVVRRAFP HCLAFSYMDD VVLGAKSVQH LESLY                               95

SEQ ID NO: 10               moltype = AA   length = 110
FEATURE                     Location/Qualifiers
REGION                      1..110
                            note = HBV CONSENSUS SEQUENCE
SITE                        41
                            note = MISC_FEATURE - S OR T
SITE                        90
                            note = MISC_FEATURE - C OR S
source                      1..110
                            mol_type = protein
                            organism = synthetic construct
SEQUENCE: 10
MQLFHLCLII SCSCPTVQAS KLCLGWLWGM DIDPYKEFGA XVELLSFLPS DFFPSVRDLL    60
DTASALYREA LESPEHCSPH HTALRQAILX WGELMTLATW VGSNLEDPAS              110
```

```
SEQ ID NO: 11            moltype = AA   length = 123
FEATURE                  Location/Qualifiers
REGION                   1..123
                         note = HBV CONSENSUS SEQUENCE
SITE                     44
                         note = MISC_FEATURE - C OR S
source                   1..123
                         mol_type = protein
                         organism = synthetic construct
SEQUENCE: 11
FLPSDFFPSV RDLLDTASAL YREALESPEH CSPHHTALRQ AILXWGELMT LATWVGSNLE   60
DPASRDLVVS YVNTNMGLKI RQLLWFHISC LTFGRETVLE YLVSFGVWIR TPPAYRPPNA  120
PIL                                                                123

SEQ ID NO: 12            moltype = AA   length = 102
FEATURE                  Location/Qualifiers
REGION                   1..102
                         note = HBV CONSENSUS SEQUENCE
source                   1..102
                         mol_type = protein
                         organism = synthetic construct
SEQUENCE: 12
ASRDLVVSYV NTNMGLKIRQ LLWFHISCLT FGRETVLEYL VSFGVWIRTP PAYRPPNAPI   60
LSTLPETTVV RRRGRSPRRR TPSPRRRRSQ SPRRRRSQSR ES                     102

SEQ ID NO: 13            moltype = AA   length = 54
FEATURE                  Location/Qualifiers
REGION                   1..54
                         note = HBV CONSENSUS SEQUENCE
source                   1..54
                         mol_type = protein
                         organism = synthetic construct
SEQUENCE: 13
TPPAYRPPNA PILSTLPETT VVRRRGRSPR RRTPSPRRRR SQSPRRRRSQ SRES          54

SEQ ID NO: 14            moltype = AA   length = 40
FEATURE                  Location/Qualifiers
REGION                   1..40
                         note = HBV CONSENSUS SEQUENCE
source                   1..40
                         mol_type = protein
                         organism = synthetic construct
SEQUENCE: 14
QQFVGPLTVN EKRRLKLIMP ARFYPNVTKY LPLDKGIKPY                          40

SEQ ID NO: 15            moltype = AA   length = 39
FEATURE                  Location/Qualifiers
REGION                   1..39
                         note = HBV CONSENSUS SEQUENCE
source                   1..39
                         mol_type = protein
                         organism = synthetic construct
SEQUENCE: 15
YPEHVVNHYF QTRHYLHTLW KAGILYKRET TRSASFCGS                           39

SEQ ID NO: 16            moltype = AA   length = 42
FEATURE                  Location/Qualifiers
REGION                   1..42
                         note = HBV CONSENSUS SEQUENCE
source                   1..42
                         mol_type = protein
                         organism = synthetic construct
SEQUENCE: 16
RVSWPKFAVP NLQSLTNLLS SNLSWLSLDV SAAFYHIPLH PA                       42

SEQ ID NO: 17            moltype = AA   length = 47
FEATURE                  Location/Qualifiers
REGION                   1..47
                         note = HBV CONSENSUS SEQUENCE
source                   1..47
                         mol_type = protein
                         organism = synthetic construct
SEQUENCE: 17
GTMQNLHDSC SRNLYVSLML LYKTYGRKLH LYSHPIILGF RKIPMGV                  47

SEQ ID NO: 18            moltype = AA   length = 40
FEATURE                  Location/Qualifiers
REGION                   1..40
```

```
                    note = HBV CONSENSUS SEQUENCE
SITE                35
                    note = MISC_FEATURE - C OR S
source              1..40
                    mol_type = protein
                    organism = synthetic construct
SEQUENCE: 18
KLHLYSHPII LGFRKIPMGV GLSPFLLAQF TSAIXSVVRR                          40

SEQ ID NO: 19       moltype = AA   length = 38
FEATURE             Location/Qualifiers
REGION              1..38
                    note = HBV CONSENSUS SEQUENCE
source              1..38
                    mol_type = protein
                    organism = synthetic construct
SEQUENCE: 19
AANWILRGTS FVYVPSALNP ADDPSRGRLG LYRPLLRL                            38

SEQ ID NO: 20       moltype = AA   length = 38
FEATURE             Location/Qualifiers
REGION              1..38
                    note = HBV CONSENSUS SEQUENCE
SITE                6
                    note = MISC_FEATURE - S OR T
source              1..38
                    mol_type = protein
                    organism = synthetic construct
SEQUENCE: 20
KEFGAXVELL SFLPSDFFPS VRDLLDTASA LYREALES                            38

SEQ ID NO: 21       moltype = AA   length = 60
FEATURE             Location/Qualifiers
REGION              1..60
                    note = HBV CONSENSUS SEQUENCE
SITE                15
                    note = MISC_FEATURE - C OR S
source              1..60
                    mol_type = protein
                    organism = synthetic construct
SEQUENCE: 21
HCSPHHTALR QAILXWGELM TLATWVGSNL EDPASRDLVV SYVNTNMGLK IRQLLWFHIS    60

SEQ ID NO: 22       moltype = AA   length = 41
FEATURE             Location/Qualifiers
REGION              1..41
                    note = HBV CONSENSUS SEQUENCE
source              1..41
                    mol_type = protein
                    organism = synthetic construct
SEQUENCE: 22
CLTFGRETVL EYLVSFGVWI RTPPAYRPPN APILSTLPET T                        41

SEQ ID NO: 23       moltype = AA   length = 33
FEATURE             Location/Qualifiers
REGION              1..33
                    note = HBV CONSENSUS SEQUENCE
source              1..33
                    mol_type = protein
                    organism = synthetic construct
SEQUENCE: 23
TPPAYRPPNA PILSTLPETT VVRRRGRSPR RRT                                 33

SEQ ID NO: 24       moltype = AA   length = 35
FEATURE             Location/Qualifiers
REGION              1..35
                    note = HBV CONSENSUS SEQUENCE
source              1..35
                    mol_type = protein
                    organism = synthetic construct
SEQUENCE: 24
VGPLTVNEKR RLKLIMPARF YPNVTKYLPL DKGIK                               35

SEQ ID NO: 25       moltype = AA   length = 35
FEATURE             Location/Qualifiers
REGION              1..35
                    note = HBV CONSENSUS SEQUENCE
source              1..35
                    mol_type = protein
```

```
                            organism = synthetic construct
SEQUENCE: 25
PEHVVNHYFQ TRHYLHTLWK AGILYKRETT RSASF                              35

SEQ ID NO: 26           moltype = AA   length = 36
FEATURE                 Location/Qualifiers
REGION                  1..36
                        note = HBV CONSENSUS SEQUENCE
source                  1..36
                        mol_type = protein
                        organism = synthetic construct
SEQUENCE: 26
RVSWPKFAVP NLQSLTNLLS SNLSWLSLDV SAAFYH                             36

SEQ ID NO: 27           moltype = AA   length = 37
FEATURE                 Location/Qualifiers
REGION                  1..37
                        note = HBV CONSENSUS SEQUENCE
source                  1..37
                        mol_type = protein
                        organism = synthetic construct
SEQUENCE: 27
SRNLYVSLML LYKTYGRKLH LYSHPIILGF RKIPMGV                            37

SEQ ID NO: 28           moltype = AA   length = 40
FEATURE                 Location/Qualifiers
REGION                  1..40
                        note = HBV CONSENSUS SEQUENCE
source                  1..40
                        mol_type = protein
                        organism = synthetic construct
SEQUENCE: 28
KLHLYSHPII LGFRKIPMGV GLSPFLLAQF TSAISSVVRR                         40

SEQ ID NO: 29           moltype = AA   length = 36
FEATURE                 Location/Qualifiers
REGION                  1..36
                        note = HBV CONSENSUS SEQUENCE
source                  1..36
                        mol_type = protein
                        organism = synthetic construct
SEQUENCE: 29
ANWILRGTSF VYVPSALNPA DDPSRGRLGL YRPLLR                             36

SEQ ID NO: 30           moltype = AA   length = 33
FEATURE                 Location/Qualifiers
REGION                  1..33
                        note = HBV CONSENSUS SEQUENCE
source                  1..33
                        mol_type = protein
                        organism = synthetic construct
SEQUENCE: 30
KEFGATVELL SFLPSDFFPS VRDLLDTASA LYR                                33

SEQ ID NO: 31           moltype = AA   length = 35
FEATURE                 Location/Qualifiers
REGION                  1..35
                        note = HBV CONSENSUS SEQUENCE
source                  1..35
                        mol_type = protein
                        organism = synthetic construct
SEQUENCE: 31
SPHHTALRQA ILSWGELMTL ATWVGSNLED PASRD                              35

SEQ ID NO: 32           moltype = AA   length = 35
FEATURE                 Location/Qualifiers
REGION                  1..35
                        note = HBV CONSENSUS SEQUENCE
source                  1..35
                        mol_type = protein
                        organism = synthetic construct
SEQUENCE: 32
LTFGRETVLE YLVSFGVWIR TPPAYRPPNA PILST                              35

SEQ ID NO: 33           moltype = AA   length = 31
FEATURE                 Location/Qualifiers
REGION                  1..31
                        note = HBV CONSENSUS SEQUENCE
source                  1..31
```

```
                            mol_type = protein
                            organism = synthetic construct
SEQUENCE: 33
PPAYRPPNAP ILSTLPETTV VRRRGRSPRR R                                    31

SEQ ID NO: 34               moltype = AA   length = 39
FEATURE                     Location/Qualifiers
REGION                      1..39
                            note = HBV CONSENSUS SEQUENCE
source                      1..39
                            mol_type = protein
                            organism = synthetic construct
SEQUENCE: 34
RVSWPKFAVP NLQSLTNLLS SNLSWLSLDV SAAFYHKKK                             39

SEQ ID NO: 35               moltype = AA   length = 39
FEATURE                     Location/Qualifiers
REGION                      1..39
                            note = HBV CONSENSUS SEQUENCE
source                      1..39
                            mol_type = protein
                            organism = synthetic construct
SEQUENCE: 35
KKKANWILRG TSFVYVPSAL NPADDPSRGR LGLYRPLLR                             39

SEQ ID NO: 36               moltype = AA   length = 38
FEATURE                     Location/Qualifiers
REGION                      1..38
                            note = HBV CONSENSUS SEQUENCE
source                      1..38
                            mol_type = protein
                            organism = synthetic construct
SEQUENCE: 36
KKKEFGATVE LLSFLPSDFF PSVRDLLDTA SALYRKKK                              38

SEQ ID NO: 37               moltype = AA   length = 38
FEATURE                     Location/Qualifiers
REGION                      1..38
                            note = HBV CONSENSUS SEQUENCE
source                      1..38
                            mol_type = protein
                            organism = synthetic construct
SEQUENCE: 37
SPHHTALRQA ILSWGELMTL ATWVGSNLED PASRDKKK                              38

SEQ ID NO: 38               moltype = AA   length = 38
FEATURE                     Location/Qualifiers
REGION                      1..38
                            note = HBV CONSENSUS SEQUENCE
source                      1..38
                            mol_type = protein
                            organism = synthetic construct
SEQUENCE: 38
LTFGRETVLE YLVSFGVWIR TPPAYRPPNA PILSTKKK                              38

SEQ ID NO: 39               moltype = AA   length = 1468
FEATURE                     Location/Qualifiers
REGION                      1..1468
                            note = HBV CONSENSUS SEQUENCE
source                      1..1468
                            mol_type = protein
                            organism = synthetic construct
SEQUENCE: 39
MPLSYQHFRK LLLLDDEAGP LEEELPRLAD EGLNRRVAED LNLGNLNVSI PWTHKVGNFT      60
GLYSSTVPVF NPEWQTPSFP HIHLQEDIIN RCQQFVGPLT VNEKRRLKLI MPARFYPNVT     120
KYLPLDKGIK PYYPEHVVNH YFQTRHYLHT LWKAGILYKR ETTRSASFCG SPYSWEQELQ     180
SCWWLQFRNS KPCSEYCLSH IVNLLEDWGP CTEHGEHHIR IPRTPARVTG GVFLVDKNPH     240
NTTESRLVVD FSQFSRGNTR VSWPKFAVPN LQSLTNLLSS NLSWLSLDVS AAFYHIPLHP     300
AAMPHLLVGS SGLSRYVARL SSNSRIINNQ HGTMQNLHDS CSRNLYVSLM LLYKTYGRKL     360
HLYSHPIILG FRKIPMGVGL SPFLLAQFTS AICSVVRRAF PHCLAFSYMD DVVLGAKSVQ     420
HLESLYTAVT NFLLSLGIHL NPNKTKRWGY SLNFMGYVIG SWGTLPQEHI VQKIKQCFRK     480
LPVNRPIDWK VCQRIVGLLG FAAPFTQCGY PALMPLYACI QAKQAFTFSP TYKAFLCKQY     540
LNLYPVARQR PGLCQVFADA TPTGWGLAIG HQRMRGTFVA PLPIHTAELL AACFARSRSG     600
AKLIGTDNSV VLSRKYTSFP WLLGCAANWI LRGTSFVYVP SALNPADDPS RGRLGLYRPL     660
LRLPFRPTTG RTSLYAVSPS VPSHLPDRVH FASPLHVAWR PPMQLFHCL IISCSCPTVQ      720
ASKLCLGWLW GMDIDPYKEF GASVELLSFL PSDFFPSVRD LLDTASALYR EALESPEHCS     780
PHHTALRQAI LCWGELMTLA TWVGSNLEDP ASRDLVVSYV NTNMGLKIRQ LLWFHISCLT     840
FGRETVLEYL VSFGVWIRTP PAYRPPNAPI LSTLPETTVV RRRGRSPRRR TPSPRRRRSQ     900
SPRRRRSQSR ESQCMAARLC CQLDPARDVL CLRPVGAESR GRPLSGPLGT LPSPSPSAVP     960
```

```
ADHGAHLSLR GLPVCAFSSA GPCALRFTSA RRMETTVNAH QILPKVLHKR TLGLSAMSTT   1020
DLEAYFKDCV FKDWEELGEE IRLKVFVLGG CRHKLVCSPA PCNFFTSAMG GWSSKPRKGM   1080
GTNLSVPNPL GFFPDHQLDP AFRANSNNPD WDFNPNKDQW PAANQVGVGA FGPGFTPPHG   1140
GLLGWSPQAQ GILTTVPADP PPASTNRQSG RQPTPISPPL RDSHPQAMQW NSTTFHQALQ   1200
DPRVRGLYFP AGGSSSGTVN PAPTTASLIS SIFSRTGDPA PNMENITSGF LGPLLVLQAG   1260
FFLLTKILTI PQSLDSWWTS LNFLGGTPVC LGQNSQSPTS NHSPTSCPPI CPGYRWMCLR   1320
RFIIFLFILL LCLIFLLVLL DYQGMLPVCP LIPGSSTTST GPCKTCTTPA QGTSMPSCC    1380
CTKPSDGNCT CIPIPSSWAF GKYLWEWASA RFSWLSLLVP FVQWFVGLSP TVWLSVIWMM   1440
WYWGPSLYNI LSPFIPLLPI FFCLWVYI                                     1468

SEQ ID NO: 40          moltype = AA   length = 55
FEATURE                Location/Qualifiers
REGION                 1..55
                       note = HBV CONSENSUS SEQUENCE
source                 1..55
                       mol_type = protein
                       organism = synthetic construct
SEQUENCE: 40
LPRLADEGLN RRVAEDLNLG NLNVSIPWTH KVGNFTGLYS STVPVFNPEW QTPSF        55

SEQ ID NO: 41          moltype = AA   length = 51
FEATURE                Location/Qualifiers
REGION                 1..51
                       note = HBV CONSENSUS SEQUENCE
source                 1..51
                       mol_type = protein
                       organism = synthetic construct
SEQUENCE: 41
CTEHGEHHIR IPRTPARVTG GVFLVDKNPH NTTESRLVVD FSQFSRGNTR V            51

SEQ ID NO: 42          moltype = AA   length = 55
FEATURE                Location/Qualifiers
REGION                 1..55
                       note = HBV CONSENSUS SEQUENCE
SITE                   22
                       note = MISC_FEATURE - C OR S
source                 1..55
                       mol_type = protein
                       organism = synthetic construct
SEQUENCE: 42
RKIPMGVGLS PFLLAQFTSA IXSVVRRAFP HCLAFSYMDD VVLGAKSVQH LESLY        55

SEQ ID NO: 43          moltype = AA   length = 52
FEATURE                Location/Qualifiers
REGION                 1..52
                       note = HBV CONSENSUS SEQUENCE
source                 1..52
                       mol_type = protein
                       organism = synthetic construct
SEQUENCE: 43
LGAKSVQHLE SLYTAVTNFL LSLGIHLNPN KTKRWGYSLN FMGYVIGSWG TL           52

SEQ ID NO: 44          moltype = AA   length = 59
FEATURE                Location/Qualifiers
REGION                 1..59
                       note = HBV CONSENSUS SEQUENCE
source                 1..59
                       mol_type = protein
                       organism = synthetic construct
SEQUENCE: 44
KIKQCFRKLP VNRPIDWKVC QRIVGLLGFA APFTQCGYPA LMPLYACIQA KQAFTFSPT    59

SEQ ID NO: 45          moltype = AA   length = 50
FEATURE                Location/Qualifiers
REGION                 1..50
                       note = HBV CONSENSUS SEQUENCE
source                 1..50
                       mol_type = protein
                       organism = synthetic construct
SEQUENCE: 45
IQAKQAFTFS PTYKAFLCKQ YLNLYPVARQ RPGLCQVFAD ATPTGWGLAI              50

SEQ ID NO: 46          moltype = AA   length = 48
FEATURE                Location/Qualifiers
REGION                 1..48
                       note = HBV CONSENSUS SEQUENCE
source                 1..48
                       mol_type = protein
                       organism = synthetic construct
```

```
SEQUENCE: 46
FADATPTGWG LAIGHQRMRG TFVAPLPIHT AELLAACFAR SRSGAKLI                48

SEQ ID NO: 47           moltype = AA  length = 59
FEATURE                 Location/Qualifiers
REGION                  1..59
                        note = HBV CONSENSUS SEQUENCE
source                  1..59
                        mol_type = protein
                        organism = synthetic construct
SEQUENCE: 47
ACFARSRSGA KLIGTDNSVV LSRKYTSFPW LLGCAANWIL RGTSFVYVPS ALNPADDPS    59

SEQ ID NO: 48           moltype = AA  length = 63
FEATURE                 Location/Qualifiers
REGION                  1..63
                        note = HBV CONSENSUS SEQUENCE
source                  1..63
                        mol_type = protein
                        organism = synthetic construct
SEQUENCE: 48
YVPSALNPAD DPSRGRLGLY RPLLRLPFRP TTGRTSLYAV SPSVPSHLPD RVHFASPLHV   60
AWR                                                                63

SEQ ID NO: 49           moltype = AA  length = 60
FEATURE                 Location/Qualifiers
REGION                  1..60
                        note = HBV CONSENSUS SEQUENCE
SITE                    41
                        note = MISC_FEATURE - S OR T
source                  1..60
                        mol_type = protein
                        organism = synthetic construct
SEQUENCE: 49
MQLFHLCLII SCSCPTVQAS KLCLGWLWGM DIDPYKEFGA XVELLSFLPS DFFPSVRDLL   60

SEQ ID NO: 50           moltype = AA  length = 64
FEATURE                 Location/Qualifiers
REGION                  1..64
                        note = HBV CONSENSUS SEQUENCE
SITE                    44
                        note = MISC_FEATURE - C OR S
source                  1..64
                        mol_type = protein
                        organism = synthetic construct
SEQUENCE: 50
FLPSDFFPSV RDLLDTASAL YREALESPEH CSPHHTALRQ AILXWGELMT LATWVGSNLE   60
DPAS                                                               64

SEQ ID NO: 51           moltype = AA  length = 61
FEATURE                 Location/Qualifiers
REGION                  1..61
                        note = HBV CONSENSUS SEQUENCE
source                  1..61
                        mol_type = protein
                        organism = synthetic construct
SEQUENCE: 51
ASRDLVVSYV NTNMGLKIRQ LLWFHISCLT FGRETVLEYL VSFGVWIRTP PAYRPPNAPI   60
L                                                                  61

SEQ ID NO: 52           moltype = AA  length = 52
FEATURE                 Location/Qualifiers
REGION                  1..52
                        note = HBV CONSENSUS SEQUENCE
source                  1..52
                        mol_type = protein
                        organism = synthetic construct
SEQUENCE: 52
HLSLRGLPVC AFSSAGPCAL RFTSARRMET TVNAHQILPK VLHKRTLGLS AM           52

SEQ ID NO: 53           moltype = AA  length = 58
FEATURE                 Location/Qualifiers
REGION                  1..58
                        note = HBV CONSENSUS SEQUENCE
source                  1..58
                        mol_type = protein
                        organism = synthetic construct
SEQUENCE: 53
KVLHKRTLGL SAMSTTDLEA YFKDCVFKDW EELGEEIRLK VFVLGGCRHK LVCSPAPC     58
```

```
SEQ ID NO: 54          moltype = AA  length = 54
FEATURE                Location/Qualifiers
REGION                 1..54
                       note = HBV CONSENSUS SEQUENCE
source                 1..54
                       mol_type = protein
                       organism = synthetic construct
SEQUENCE: 54
RQPTPISPPL RDSHPQAMQW NSTTFHQALQ DPRVRGLYFP AGGSSSGTVN PAPT          54

SEQ ID NO: 55          moltype = AA  length = 56
FEATURE                Location/Qualifiers
REGION                 1..56
                       note = HBV CONSENSUS SEQUENCE
source                 1..56
                       mol_type = protein
                       organism = synthetic construct
SEQUENCE: 55
PNMENITSGF LGPLLVLQAG FFLLTKILTI PQSLDSWWTS LNFLGGTPVC LGQNSQ        56

SEQ ID NO: 56          moltype = AA  length = 35
FEATURE                Location/Qualifiers
REGION                 1..35
                       note = HBV CONSENSUS SEQUENCE
source                 1..35
                       mol_type = protein
                       organism = synthetic construct
SEQUENCE: 56
PGYRWMCLRR FIIFLFILLL CLIFLLVLLD YQGML                               35

SEQ ID NO: 57          moltype = AA  length = 56
FEATURE                Location/Qualifiers
REGION                 1..56
                       note = HBV CONSENSUS SEQUENCE
source                 1..56
                       mol_type = protein
                       organism = synthetic construct
SEQUENCE: 57
IPIPSSWAFG KYLWEWASAR FSWLSLLVPF VQWFVGLSPT VWLSVIWMMW YWGPSL        56

SEQ ID NO: 58          moltype = AA  length = 49
FEATURE                Location/Qualifiers
REGION                 1..49
                       note = HBV CONSENSUS SEQUENCE
source                 1..49
                       mol_type = protein
                       organism = synthetic construct
SEQUENCE: 58
EGLNRRVAED LNLGNLNVSI PWTHKVGNFT GLYSSTVPVF NPEWQTPSF                49

SEQ ID NO: 59          moltype = AA  length = 39
FEATURE                Location/Qualifiers
REGION                 1..39
                       note = HBV CONSENSUS SEQUENCE
source                 1..39
                       mol_type = protein
                       organism = synthetic construct
SEQUENCE: 59
RTPARVTGGV FLVDKNPHNT TESRLVVDFS QFSRGNTRV                           39

SEQ ID NO: 60          moltype = AA  length = 37
FEATURE                Location/Qualifiers
REGION                 1..37
                       note = HBV CONSENSUS SEQUENCE
source                 1..37
                       mol_type = protein
                       organism = synthetic construct
SEQUENCE: 60
KFAVPNLQSL TNLLSSNLSW LSLDVSAAFY HIPLHPA                             37

SEQ ID NO: 61          moltype = AA  length = 38
FEATURE                Location/Qualifiers
REGION                 1..38
                       note = HBV CONSENSUS SEQUENCE
source                 1..38
                       mol_type = protein
                       organism = synthetic construct
SEQUENCE: 61
```

```
VSAAFYHIPL HPAAMPHLLV GSSGLSRYVA RLSSNSRI                                   38

SEQ ID NO: 62           moltype = AA   length = 37
FEATURE                 Location/Qualifiers
REGION                  1..37
                        note = HBV CONSENSUS SEQUENCE
source                  1..37
                        mol_type = protein
                        organism = synthetic construct
SEQUENCE: 62
LAFSYMDDVV LGAKSVQHLE SLYTAVTNFL LSLGIHL                                    37

SEQ ID NO: 63           moltype = AA   length = 38
FEATURE                 Location/Qualifiers
REGION                  1..38
                        note = HBV CONSENSUS SEQUENCE
source                  1..38
                        mol_type = protein
                        organism = synthetic construct
SEQUENCE: 63
AVTNFLLSLG IHLNPNKTKR WGYSLNFMGY VIGSWGTL                                   38

SEQ ID NO: 64           moltype = AA   length = 41
FEATURE                 Location/Qualifiers
REGION                  1..41
                        note = HBV CONSENSUS SEQUENCE
source                  1..41
                        mol_type = protein
                        organism = synthetic construct
SEQUENCE: 64
FADATPTGWG LAIGHQRMRG TFVAPLPIHT AELLAACFAR S                               41

SEQ ID NO: 65           moltype = AA   length = 41
FEATURE                 Location/Qualifiers
REGION                  1..41
                        note = HBV CONSENSUS SEQUENCE
source                  1..41
                        mol_type = protein
                        organism = synthetic construct
SEQUENCE: 65
PADDPSRGRL GLYRPLLRLP FRPTTGRTSL YAVSPSVPSH L                               41

SEQ ID NO: 66           moltype = AA   length = 42
FEATURE                 Location/Qualifiers
REGION                  1..42
                        note = HBV CONSENSUS SEQUENCE
source                  1..42
                        mol_type = protein
                        organism = synthetic construct
SEQUENCE: 66
PLLRLPFRPT TGRTSLYAVS PSVPSHLPDR VHFASPLHVA WR                              42

SEQ ID NO: 67           moltype = AA   length = 35
FEATURE                 Location/Qualifiers
REGION                  1..35
                        note = HBV CONSENSUS SEQUENCE
SITE                    15
                        note = MISC_FEATURE - C OR S
source                  1..35
                        mol_type = protein
                        organism = synthetic construct
SEQUENCE: 67
HCSPHHTALR QAILXWGELM TLATWVGSNL EDPAS                                      35

SEQ ID NO: 68           moltype = AA   length = 27
FEATURE                 Location/Qualifiers
REGION                  1..27
                        note = HBV CONSENSUS SEQUENCE
source                  1..27
                        mol_type = protein
                        organism = synthetic construct
SEQUENCE: 68
ASRDLVVSYV NTNMGLKIRQ LLWFHIS                                               27

SEQ ID NO: 69           moltype = AA   length = 40
FEATURE                 Location/Qualifiers
REGION                  1..40
                        note = HBV CONSENSUS SEQUENCE
source                  1..40
```

```
SEQUENCE: 69
ASRDLVVSYV NTNMGLKIRQ LLWFHISCLT FGRETVLEYL                              40

SEQ ID NO: 70           moltype = AA   length = 46
FEATURE                 Location/Qualifiers
REGION                  1..46
                        note = HBV CONSENSUS SEQUENCE
source                  1..46
                        mol_type = protein
                        organism = synthetic construct
SEQUENCE: 70
SAGPCALRFT SARRMETTVN AHQILPKVLH KRTLGLSAMS TTDLEA                       46

SEQ ID NO: 71           moltype = AA   length = 43
FEATURE                 Location/Qualifiers
REGION                  1..43
                        note = HBV CONSENSUS SEQUENCE
source                  1..43
                        mol_type = protein
                        organism = synthetic construct
SEQUENCE: 71
TSGFLGPLLV LQAGFFLLTR ILTIPQSLDS WWTSLNFLGG TPV                          43

SEQ ID NO: 72           moltype = AA   length = 41
FEATURE                 Location/Qualifiers
REGION                  1..41
                        note = HBV CONSENSUS SEQUENCE
source                  1..41
                        mol_type = protein
                        organism = synthetic construct
SEQUENCE: 72
AFGKYLWEWA SARFSWLSLL VPFVQWFVGL SPTVWLSVIW M                            41

SEQ ID NO: 73           moltype = AA   length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 73
LPRLADEGLN RRVAEDLNL                                                     19

SEQ ID NO: 74           moltype = AA   length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 74
EGLNRRVAED LNLGNLNVSI                                                    20

SEQ ID NO: 75           moltype = AA   length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 75
AEDLNLGNLN VSIPWTHKV                                                     19

SEQ ID NO: 76           moltype = AA   length = 18
FEATURE                 Location/Qualifiers
REGION                  1..18
                        note = HBV CONSENSUS SEQUENCE
source                  1..18
                        mol_type = protein
                        organism = synthetic construct
SEQUENCE: 76
NLGNLNVSIP WTHKVGNF                                                      18

SEQ ID NO: 77           moltype = AA   length = 20
FEATURE                 Location/Qualifiers
REGION                  1..20
                        note = HBV CONSENSUS SEQUENCE
```

-continued

```
source                   1..20
                         mol_type = protein
                         organism = synthetic construct
SEQUENCE: 77
LNVSIPWTHK VGNFTGLYSS                                                    20

SEQ ID NO: 78            moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 78
THKVGNFTGL YSSTVPVFNP                                                    20

SEQ ID NO: 79            moltype = AA   length = 19
FEATURE                  Location/Qualifiers
REGION                   1..19
                         note = HBV CONSENSUS SEQUENCE
source                   1..19
                         mol_type = protein
                         organism = synthetic construct
SEQUENCE: 79
GLYSSTVPVF NPEWQTPSF                                                     19

SEQ ID NO: 80            moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 80
KQQFVGPLTV NEKRRLKLIM                                                    20

SEQ ID NO: 81            moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 81
LTVNEKRRLK LIMPARFYPN                                                    20

SEQ ID NO: 82            moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 82
RLKLIMPARF YPNVTKYLPL                                                    20

SEQ ID NO: 83            moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 83
ARFYPNVTKY LPLDKGIKPY                                                    20

SEQ ID NO: 84            moltype = AA   length = 19
FEATURE                  Location/Qualifiers
REGION                   1..19
                         note = HBV CONSENSUS SEQUENCE
source                   1..19
                         mol_type = protein
                         organism = synthetic construct
SEQUENCE: 84
TKYLPLDKGI KPYYPEHVV                                                     19

SEQ ID NO: 85            moltype = AA   length = 20
FEATURE                  Location/Qualifiers
REGION                   1..20
```

```
                    note = HBV CONSENSUS SEQUENCE
source              1..20
                    mol_type = protein
                    organism = synthetic construct
SEQUENCE: 85
DKGIKPYYPE HVVNHYFQTR                                               20

SEQ ID NO: 86       moltype = AA  length = 19
FEATURE             Location/Qualifiers
REGION              1..19
                    note = HBV CONSENSUS SEQUENCE
source              1..19
                    mol_type = protein
                    organism = synthetic construct
SEQUENCE: 86
YPEHVVNHYF QTRHYLHTL                                                19

SEQ ID NO: 87       moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 87
NHYFQTRHYL HTLWKAGILY                                               20

SEQ ID NO: 88       moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 88
RHYLHTLWKA GILYKRETTR                                               20

SEQ ID NO: 89       moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 89
WKAGILYKRE TTRSASFCGS                                               20

SEQ ID NO: 90       moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 90
RETTRSASFC GSPYSWEQEL                                               20

SEQ ID NO: 91       moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 91
SFCGSPYSWE QELQSCWWLQ                                               20

SEQ ID NO: 92       moltype = AA  length = 18
FEATURE             Location/Qualifiers
REGION              1..18
                    note = HBV CONSENSUS SEQUENCE
source              1..18
                    mol_type = protein
                    organism = synthetic construct
SEQUENCE: 92
CTEHGEHHIR IPRTPARV                                                 18

SEQ ID NO: 93       moltype = AA  length = 19
FEATURE             Location/Qualifiers
```

```
REGION                    1..19
                          note = HBV CONSENSUS SEQUENCE
source                    1..19
                          mol_type = protein
                          organism = synthetic construct
SEQUENCE: 93
HHIRIPRTPA RVTGGVFLV                                                    19

SEQ ID NO: 94             moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 94
RTPARVTGGV FLVDKNPHN                                                    19

SEQ ID NO: 95             moltype = AA  length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 95
TGGVFLVDKN PHNTTESRLV                                                   20

SEQ ID NO: 96             moltype = AA  length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 96
DKNPHNTTES RLVVDFSQFS                                                   20

SEQ ID NO: 97             moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 97
TESRLVVDFS QFSRGNTRV                                                    19

SEQ ID NO: 98             moltype = AA  length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 98
KFAVPNLQSL TNLLSSNLSW                                                   20

SEQ ID NO: 99             moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 99
LQSLTNLLSS NLSWLSLDV                                                    19

SEQ ID NO: 100            moltype = AA  length = 18
FEATURE                   Location/Qualifiers
REGION                    1..18
                          note = HBV CONSENSUS SEQUENCE
source                    1..18
                          mol_type = protein
                          organism = synthetic construct
SEQUENCE: 100
LLSSNLSWLS LDVSAAFY                                                     18

SEQ ID NO: 101            moltype = AA  length = 20
```

```
FEATURE                  Location/Qualifiers
REGION                   1..20
                         note = HBV CONSENSUS SEQUENCE
source                   1..20
                         mol_type = protein
                         organism = synthetic construct
SEQUENCE: 101
LSWLSLDVSA AFYHIPLHPA                                                     20

SEQ ID NO: 102           moltype = AA  length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 102
VSAAFYHIPL HPAAMPHLLV                                                     20

SEQ ID NO: 103           moltype = AA  length = 19
FEATURE                  Location/Qualifiers
REGION                   1..19
                         note = HBV CONSENSUS SEQUENCE
source                   1..19
                         mol_type = protein
                         organism = synthetic construct
SEQUENCE: 103
LHPAAMPHLL VGSSGLSRY                                                      19

SEQ ID NO: 104           moltype = AA  length = 22
FEATURE                  Location/Qualifiers
REGION                   1..22
                         note = HBV CONSENSUS SEQUENCE
source                   1..22
                         mol_type = protein
                         organism = synthetic construct
SEQUENCE: 104
HLLVGSSGLS RYVARLSSNS RI                                                  22

SEQ ID NO: 105           moltype = AA  length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 105
GTMQNLHDSC SRNLYVSLML                                                     20

SEQ ID NO: 106           moltype = AA  length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 106
DSCSRNLYVS LMLLYKTYGR                                                     20

SEQ ID NO: 107           moltype = AA  length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 107
YVSLMLLYKT YGRKLHLYSH                                                     20

SEQ ID NO: 108           moltype = AA  length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 108
YKTYGRKLHL YSHPIILGFR                                                     20
```

```
SEQ ID NO: 109               moltype = AA   length = 20
FEATURE                      Location/Qualifiers
REGION                       1..20
                             note = HBV CONSENSUS SEQUENCE
source                       1..20
                             mol_type = protein
                             organism = synthetic construct
SEQUENCE: 109
KLHLYSHPII LGFRKIPMGV                                                    20

SEQ ID NO: 110               moltype = AA   length = 19
FEATURE                      Location/Qualifiers
REGION                       1..19
                             note = HBV CONSENSUS SEQUENCE
source                       1..19
                             mol_type = protein
                             organism = synthetic construct
SEQUENCE: 110
PIILGFRKIP MGVGLSPFL                                                     19

SEQ ID NO: 111               moltype = AA   length = 20
FEATURE                      Location/Qualifiers
REGION                       1..20
                             note = HBV CONSENSUS SEQUENCE
source                       1..20
                             mol_type = protein
                             organism = synthetic construct
SEQUENCE: 111
RKIPMGVGLS PFLLAQFTSA                                                    20

SEQ ID NO: 112               moltype = AA   length = 20
FEATURE                      Location/Qualifiers
REGION                       1..20
                             note = HBV CONSENSUS SEQUENCE
SITE                         15
                             note = MISC_FEATURE - C OR S
source                       1..20
                             mol_type = protein
                             organism = synthetic construct
SEQUENCE: 112
GLSPFLLAQF TSAIXSVVRR                                                    20

SEQ ID NO: 113               moltype = AA   length = 19
FEATURE                      Location/Qualifiers
REGION                       1..19
                             note = HBV CONSENSUS SEQUENCE
source                       1..19
                             mol_type = protein
                             organism = synthetic construct
SEQUENCE: 113
LLAQFTSAIC SVVRRAFPH                                                     19

SEQ ID NO: 114               moltype = AA   length = 20
FEATURE                      Location/Qualifiers
REGION                       1..20
                             note = HBV CONSENSUS SEQUENCE
source                       1..20
                             mol_type = protein
                             organism = synthetic construct
SEQUENCE: 114
SAICSVVRRA FPHCLAFSYM                                                    20

SEQ ID NO: 115               moltype = AA   length = 19
FEATURE                      Location/Qualifiers
REGION                       1..19
                             note = HBV CONSENSUS SEQUENCE
source                       1..19
                             mol_type = protein
                             organism = synthetic construct
SEQUENCE: 115
RAFPHCLAFS YMDDVVLGA                                                     19

SEQ ID NO: 116               moltype = AA   length = 19
FEATURE                      Location/Qualifiers
REGION                       1..19
                             note = HBV CONSENSUS SEQUENCE
source                       1..19
                             mol_type = protein
                             organism = synthetic construct
```

```
SEQUENCE: 116
LAFSYMDDVV LGAKSVQHL                                                    19

SEQ ID NO: 117          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 117
YMDDVVLGAK SVQHLESLY                                                    19

SEQ ID NO: 118          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 118
LGAKSVQHLE SLYTAVTNFL                                                   20

SEQ ID NO: 119          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 119
HLESLYTAVT NFLLSLGIHL                                                   20

SEQ ID NO: 120          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 120
AVTNFLLSLG IHLNPNKTKR                                                   20

SEQ ID NO: 121          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 121
SLGIHLNPNK TKRWGYSLNF                                                   20

SEQ ID NO: 122          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 122
HLNPNKTKRW GYSLNFMGYV                                                   20

SEQ ID NO: 123          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 123
KRWGYSLNFM GYVIGSWGTL                                                   20

SEQ ID NO: 124          moltype = AA  length = 18
FEATURE                 Location/Qualifiers
REGION                  1..18
                        note = HBV CONSENSUS SEQUENCE
source                  1..18
                        mol_type = protein
```

```
                        organism = synthetic construct
SEQUENCE: 124
KIKQCFRKLP VNRPIDWK                                                    18

SEQ ID NO: 125          moltype = AA   length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 125
FRKLPVNRPI DWKVCQRIVG                                                  20

SEQ ID NO: 126          moltype = AA   length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 126
RPIDWKVCQR IVGLLGFAA                                                   19

SEQ ID NO: 127          moltype = AA   length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 127
VCQRIVGLLG FAAPFTQCGY                                                  20

SEQ ID NO: 128          moltype = AA   length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 128
GLLGFAAPFT QCGYPALMPL                                                  20

SEQ ID NO: 129          moltype = AA   length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 129
FTQCGYPALM PLYACIQAK                                                   19

SEQ ID NO: 130          moltype = AA   length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 130
ALMPLYACIQ AKQAFTFSPT                                                  20

SEQ ID NO: 131          moltype = AA   length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 131
IQAKQAFTFS PTYKAFLCK                                                   19

SEQ ID NO: 132          moltype = AA   length = 19
FEATURE                 Location/Qualifiers
REGION                  1..19
                        note = HBV CONSENSUS SEQUENCE
source                  1..19
```

```
                              -continued mol_type = protein
                           organism = synthetic construct
SEQUENCE: 132
FTFSPTYKAF LCKQYLNLY                                             19

SEQ ID NO: 133             moltype = AA  length = 19
FEATURE                    Location/Qualifiers
REGION                     1..19
                           note = HBV CONSENSUS SEQUENCE
source                     1..19
                           mol_type = protein
                           organism = synthetic construct
SEQUENCE: 133
YKAFLCKQYL NLYPVARQR                                             19

SEQ ID NO: 134             moltype = AA  length = 19
FEATURE                    Location/Qualifiers
REGION                     1..19
                           note = HBV CONSENSUS SEQUENCE
source                     1..19
                           mol_type = protein
                           organism = synthetic construct
SEQUENCE: 134
KQYLNLYPVA RQRPGLCQV                                             19

SEQ ID NO: 135             moltype = AA  length = 20
FEATURE                    Location/Qualifiers
REGION                     1..20
                           note = HBV CONSENSUS SEQUENCE
source                     1..20
                           mol_type = protein
                           organism = synthetic construct
SEQUENCE: 135
YPVARQRPGL CQVFADATPT                                            20

SEQ ID NO: 136             moltype = AA  length = 18
FEATURE                    Location/Qualifiers
REGION                     1..18
                           note = HBV CONSENSUS SEQUENCE
source                     1..18
                           mol_type = protein
                           organism = synthetic construct
SEQUENCE: 136
GLCQVFADAT PTGWGLAI                                              18

SEQ ID NO: 137             moltype = AA  length = 19
FEATURE                    Location/Qualifiers
REGION                     1..19
                           note = HBV CONSENSUS SEQUENCE
source                     1..19
                           mol_type = protein
                           organism = synthetic construct
SEQUENCE: 137
FADATPTGWG LAIGHQRMR                                             19

SEQ ID NO: 138             moltype = AA  length = 19
FEATURE                    Location/Qualifiers
REGION                     1..19
                           note = HBV CONSENSUS SEQUENCE
source                     1..19
                           mol_type = protein
                           organism = synthetic construct
SEQUENCE: 138
GWGLAIGHQR MRGTFVAPL                                             19

SEQ ID NO: 139             moltype = AA  length = 20
FEATURE                    Location/Qualifiers
REGION                     1..20
                           note = HBV CONSENSUS SEQUENCE
source                     1..20
                           mol_type = protein
                           organism = synthetic construct
SEQUENCE: 139
GHQRMRGTFV APLPIHTAEL                                            20

SEQ ID NO: 140             moltype = AA  length = 20
FEATURE                    Location/Qualifiers
REGION                     1..20
                           note = HBV CONSENSUS SEQUENCE
```

```
                             -continued source              1..20
                    mol_type = protein
                    organism = synthetic construct
SEQUENCE: 140
FVAPLPIHTA ELLAACFARS                                              20

SEQ ID NO: 141      moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 141
HTAELLAACF ARSRSGAKLI                                              20

SEQ ID NO: 142      moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 142
ACFARSRSGA KLIGTDNSVV                                              20

SEQ ID NO: 143      moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 143
GAKLIGTDNS VVLSRKYTSF                                              20

SEQ ID NO: 144      moltype = AA  length = 20
FEATURE             Location/Qualifiers
REGION              1..20
                    note = HBV CONSENSUS SEQUENCE
source              1..20
                    mol_type = protein
                    organism = synthetic construct
SEQUENCE: 144
DNSVVLSRKY TSFPWLLGCA                                              20

SEQ ID NO: 145      moltype = AA  length = 18
FEATURE             Location/Qualifiers
REGION              1..18
                    note = HBV CONSENSUS SEQUENCE
source              1..18
                    mol_type = protein
                    organism = synthetic construct
SEQUENCE: 145
RKYTSFPWLL GCAANWIL                                                18

SEQ ID NO: 146      moltype = AA  length = 19
FEATURE             Location/Qualifiers
REGION              1..19
                    note = HBV CONSENSUS SEQUENCE
source              1..19
                    mol_type = protein
                    organism = synthetic construct
SEQUENCE: 146
FPWLLGCAAN WILRGTSFV                                               19

SEQ ID NO: 147      moltype = AA  length = 19
FEATURE             Location/Qualifiers
REGION              1..19
                    note = HBV CONSENSUS SEQUENCE
source              1..19
                    mol_type = protein
                    organism = synthetic construct
SEQUENCE: 147
AANWILRGTS FVYVPSALN                                               19

SEQ ID NO: 148      moltype = AA  length = 21
FEATURE             Location/Qualifiers
REGION              1..21
```

```
                        note = HBV CONSENSUS SEQUENCE
source                  1..21
                        mol_type = protein
                        organism = synthetic construct
SEQUENCE: 148
ILRGTSFVYV PSALNPADDP S                                              21

SEQ ID NO: 149          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 149
YVPSALNPAD DPSRGRLGLY                                                20

SEQ ID NO: 150          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 150
PADDPSRGRL GLYRPLLRL                                                 19

SEQ ID NO: 151          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 151
RLGLYRPLLR LPFRPTTGR                                                 19

SEQ ID NO: 152          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 152
PLLRLPFRPT TGRTSLYAV                                                 19

SEQ ID NO: 153          moltype = AA  length = 17
FEATURE                 Location/Qualifiers
REGION                  1..17
                        note = HBV CONSENSUS SEQUENCE
source                  1..17
                        mol_type = protein
                        organism = synthetic construct
SEQUENCE: 153
FRPTTGRTSL YAVSPSV                                                   17

SEQ ID NO: 154          moltype = AA  length = 18
FEATURE                 Location/Qualifiers
REGION                  1..18
                        note = HBV CONSENSUS SEQUENCE
source                  1..18
                        mol_type = protein
                        organism = synthetic construct
SEQUENCE: 154
TTGRTSLYAV SPSVPSHL                                                  18

SEQ ID NO: 155          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 155
SLYAVSPSVP SHLPDRVHFA                                                20

SEQ ID NO: 156          moltype = AA  length = 21
FEATURE                 Location/Qualifiers
```

```
REGION                    1..21
                          note = HBV CONSENSUS SEQUENCE
source                    1..21
                          mol_type = protein
                          organism = synthetic construct
SEQUENCE: 156
SVPSHLPDRV HFASPLHVAW R                                                    21

SEQ ID NO: 157            moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 157
MQLFHLCLII SCSCPTVQA                                                       19

SEQ ID NO: 158            moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 158
LIISCSCPTV QASKLCLGW                                                       19

SEQ ID NO: 159            moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 159
CPTVQASKLC LGWLWGMDI                                                       19

SEQ ID NO: 160            moltype = AA  length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 160
SKLCLGWLWG MDIDPYKEF                                                       19

SEQ ID NO: 161            moltype = AA  length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 161
WLWGMDIDPY KEFGASVELL                                                      20

SEQ ID NO: 162            moltype = AA  length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 162
IDPYKEFGAS VELLSFLPSD                                                      20

SEQ ID NO: 163            moltype = AA  length = 21
FEATURE                   Location/Qualifiers
REGION                    1..21
                          note = HBV CONSENSUS SEQUENCE
source                    1..21
                          mol_type = protein
                          organism = synthetic construct
SEQUENCE: 163
KEFGASVELL SFLPSDFFPS V                                                    21

SEQ ID NO: 164            moltype = AA  length = 18
```

```
FEATURE                 Location/Qualifiers
REGION                  1..18
                        note = HBV CONSENSUS SEQUENCE
source                  1..18
                        mol_type = protein
                        organism = synthetic construct
SEQUENCE: 164
ELLSFLPSDF FPSVRDLL                                                       18

SEQ ID NO: 165          moltype = AA  length = 21
FEATURE                 Location/Qualifiers
REGION                  1..21
                        note = HBV CONSENSUS SEQUENCE
source                  1..21
                        mol_type = protein
                        organism = synthetic construct
SEQUENCE: 165
FLPSDFFPSV RDLLDTASAL Y                                                   21

SEQ ID NO: 166          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 166
SVRDLLDTAS ALYREALES                                                      19

SEQ ID NO: 167          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 167
DTASALYREA LESPEHCSPH                                                     20

SEQ ID NO: 168          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 168
REALESPEHC SPHHTALRQA                                                     20

SEQ ID NO: 169          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 169
HCSPHHTALR QAILCWGELM                                                     20

SEQ ID NO: 170          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 170
ALRQAILCWG ELMTLATWV                                                      19

SEQ ID NO: 171          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 171
WGELMTLATW VGSNLEDPAS                                                     20
```

-continued

```
SEQ ID NO: 172            moltype = AA   length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 172
ASRDLVVSYV NTNMGLKIR                                                    19

SEQ ID NO: 173            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 173
SYVNTNMGLK IRQLLWFHIS                                                   20

SEQ ID NO: 174            moltype = AA   length = 19
FEATURE                   Location/Qualifiers
REGION                    1..19
                          note = HBV CONSENSUS SEQUENCE
source                    1..19
                          mol_type = protein
                          organism = synthetic construct
SEQUENCE: 174
GLKIRQLLWF HISCLTFGR                                                    19

SEQ ID NO: 175            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 175
LLWFHISCLT FGRETVLEYL                                                   20

SEQ ID NO: 176            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 176
CLTFGRETVL EYLVSFGVWI                                                   20

SEQ ID NO: 177            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 177
TVLEYLVSFG VWIRTPPAYR                                                   20

SEQ ID NO: 178            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 178
SFGVWIRTPP AYRPPNAPIL                                                   20

SEQ ID NO: 179            moltype = AA   length = 20
FEATURE                   Location/Qualifiers
REGION                    1..20
                          note = HBV CONSENSUS SEQUENCE
source                    1..20
                          mol_type = protein
                          organism = synthetic construct
SEQUENCE: 179
TPPAYRPPNA PILSTLPETT                                                   20
```

```
SEQ ID NO: 180          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 180
PNAPILSTLP ETTVVRRRGR                                                    20

SEQ ID NO: 181          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 181
TLPETTVVRR RGRSPRRRT                                                     19

SEQ ID NO: 182          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 182
VVRRRGRSPR RRTPSPRRRR                                                    20

SEQ ID NO: 183          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 183
SPRRRTPSPR RRRSQSPRRR                                                    20

SEQ ID NO: 184          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 184
SPRRRSQSP RRRRSQSRES                                                     20

SEQ ID NO: 185          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 185
HLSLRGLPVC AFSSAGPCAL                                                    20

SEQ ID NO: 186          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 186
LPVCAFSSAG PCALRFTSAR                                                    20

SEQ ID NO: 187          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 187
```

```
SAGPCALRFT SARRMETTV                                              19

SEQ ID NO: 188          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 188
LRFTSARRME TTVNAHQIL                                              19

SEQ ID NO: 189          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 189
RRMETTVNAH QILPKVLHKR                                             20

SEQ ID NO: 190          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 190
NAHQILPKVL HKRTLGLSAM                                             20

SEQ ID NO: 191          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 191
KVLHKRTLGL SAMSTTDLEA                                             20

SEQ ID NO: 192          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 192
LGLSAMSTTD LEAYFKDCVF                                             20

SEQ ID NO: 193          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 193
TTDLEAYFKD CVFKDWEEL                                              19

SEQ ID NO: 194          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 194
YFKDCVFKDW EELGEEIRL                                              19

SEQ ID NO: 195          moltype = AA  length = 18
FEATURE                 Location/Qualifiers
REGION                  1..18
                        note = HBV CONSENSUS SEQUENCE
source                  1..18
                        mol_type = protein
                        organism = synthetic construct
```

-continued

```
SEQUENCE: 195
FKDWEELGEE IRLKVFVL                                                  18

SEQ ID NO: 196          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 196
ELGEEIRLKV FVLGGCRHKL                                                20

SEQ ID NO: 197          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 197
LKVFVLGGCR HKLVCSPAPC                                                20

SEQ ID NO: 198          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 198
RQPTPISPPL RDSHPQAMQW                                                20

SEQ ID NO: 199          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 199
PPLRDSHPQA MQWNSTTFH                                                 19

SEQ ID NO: 200          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 200
HPQAMQWNST TFHQALQDPR                                                20

SEQ ID NO: 201          moltype = AA  length = 20
FEATURE                 Location/Qualifiers
REGION                  1..20
                        note = HBV CONSENSUS SEQUENCE
source                  1..20
                        mol_type = protein
                        organism = synthetic construct
SEQUENCE: 201
STTFHQALQD PRVRGLYFPA                                                20

SEQ ID NO: 202          moltype = AA  length = 19
FEATURE                 Location/Qualifiers
REGION                  1..19
                        note = HBV CONSENSUS SEQUENCE
source                  1..19
                        mol_type = protein
                        organism = synthetic construct
SEQUENCE: 202
LQDPRVRGLY FPAGGSSSG                                                 19

SEQ ID NO: 203          moltype = AA  length = 20
FEATURE                 Location/Qualifiers
REGION                  1..20
                        note = HBV CONSENSUS SEQUENCE
source                  1..20
                        mol_type = protein
```

```
                              organism = synthetic construct
SEQUENCE: 203
RGLYFPAGGS SSGTVNPAPT                                                      20

SEQ ID NO: 204         moltype = AA   length = 19
FEATURE                Location/Qualifiers
REGION                 1..19
                       note = HBV CONSENSUS SEQUENCE
source                 1..19
                       mol_type = protein
                       organism = synthetic construct
SEQUENCE: 204
PNMENITSGF LGPLLVLQA                                                       19

SEQ ID NO: 205         moltype = AA   length = 20
FEATURE                Location/Qualifiers
REGION                 1..20
                       note = HBV CONSENSUS SEQUENCE
source                 1..20
                       mol_type = protein
                       organism = synthetic construct
SEQUENCE: 205
TSGFLGPLLV LQAGFFLLTK                                                      20

SEQ ID NO: 206         moltype = AA   length = 17
FEATURE                Location/Qualifiers
REGION                 1..17
                       note = HBV CONSENSUS SEQUENCE
source                 1..17
                       mol_type = protein
                       organism = synthetic construct
SEQUENCE: 206
LLVLQAGFFL LTKILTI                                                         17

SEQ ID NO: 207         moltype = AA   length = 19
FEATURE                Location/Qualifiers
REGION                 1..19
                       note = HBV CONSENSUS SEQUENCE
source                 1..19
                       mol_type = protein
                       organism = synthetic construct
SEQUENCE: 207
VLQAGFFLLT KILTIPQSL                                                       19

SEQ ID NO: 208         moltype = AA   length = 20
FEATURE                Location/Qualifiers
REGION                 1..20
                       note = HBV CONSENSUS SEQUENCE
source                 1..20
                       mol_type = protein
                       organism = synthetic construct
SEQUENCE: 208
FLLTKILTIP QSLDSWWTSL                                                      20

SEQ ID NO: 209         moltype = AA   length = 21
FEATURE                Location/Qualifiers
REGION                 1..21
                       note = HBV CONSENSUS SEQUENCE
source                 1..21
                       mol_type = protein
                       organism = synthetic construct
SEQUENCE: 209
TIPQSLDSWW TSLNFLGGTP V                                                    21

SEQ ID NO: 210         moltype = AA   length = 20
FEATURE                Location/Qualifiers
REGION                 1..20
                       note = HBV CONSENSUS SEQUENCE
source                 1..20
                       mol_type = protein
                       organism = synthetic construct
SEQUENCE: 210
WWTSLNFLGG TPVCLGQNSQ                                                      20

SEQ ID NO: 211         moltype = AA   length = 20
FEATURE                Location/Qualifiers
REGION                 1..20
                       note = HBV CONSENSUS SEQUENCE
source                 1..20
```

```
                         mol_type = protein
                         organism = synthetic construct
SEQUENCE: 211
PGYRWMCLRR FIIFLFILLL                                                        20

SEQ ID NO: 212           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 212
LRRFIIFLFI LLLCLIFLLV                                                        20

SEQ ID NO: 213           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 213
FILLLCLIFL LVLLDYQGML                                                        20

SEQ ID NO: 214           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 214
IPIPSSWAFG KYLWEWASAR                                                        20

SEQ ID NO: 215           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 215
AFGKYLWEWA SARFSWLSLL                                                        20

SEQ ID NO: 216           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 216
EWASARFSWL SLLVPFVQWF                                                        20

SEQ ID NO: 217           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 217
SWLSLLVPFV QWFVGLSPTV                                                        20

SEQ ID NO: 218           moltype = AA   length = 20
FEATURE                  Location/Qualifiers
REGION                   1..20
                         note = HBV CONSENSUS SEQUENCE
source                   1..20
                         mol_type = protein
                         organism = synthetic construct
SEQUENCE: 218
PFVQWFVGLS PTVWLSVIWM                                                        20

SEQ ID NO: 219           moltype = AA   length = 21
FEATURE                  Location/Qualifiers
REGION                   1..21
                         note = HBV CONSENSUS SEQUENCE
```

-continued

```
source                  1..21
                        mol_type = protein
                        organism = synthetic construct
SEQUENCE: 219
GLSPTVWLSV IWMMWYWGPS L                                             21

SEQ ID NO: 220          moltype = AA  length = 62
FEATURE                 Location/Qualifiers
REGION                  1..62
                        note = HBV CONSENSUS SEQUENCE
source                  1..62
                        mol_type = protein
                        organism = synthetic construct
SEQUENCE: 220
KFAVPNLQSL TNLLSSNLSW LSLDVSAAFY HIPLHPAAMP HLLVGSSGLS RYVARLSSNS   60
RI                                                                  62

SEQ ID NO: 221          moltype = AA  length = 33
FEATURE                 Location/Qualifiers
REGION                  1..33
                        note = HBV CONSENSUS SEQUENCE
source                  1..33
                        mol_type = protein
                        organism = synthetic construct
SEQUENCE: 221
GPLLVLQAGF FLLTRILTIP QSLDSWWTSL NFL                                33

SEQ ID NO: 222          moltype = AA  length = 39
FEATURE                 Location/Qualifiers
REGION                  1..39
                        note = HBV CONSENSUS SEQUENCE
source                  1..39
                        mol_type = protein
                        organism = synthetic construct
SEQUENCE: 222
KKKGPLLVLQ AGFFLLTRIL TIPQSLDSWW TSLNFLKKK                          39
```

US 11,918,645 B2

VACCINES AGAINST HEPATITIS B VIRUS

CROSS-REFERENCE TO RELATED APPLICATIONS

This application is a Continuation application of U.S. Ser. No. 16/423,149 filed 27 May 2019, which is a Divisional application of U.S. Ser. No. 14/655,041, which was filed 7 Jan. 2016, which is a U.S. National stage application filed under 35 USC § 371 of International Application No. PCT/GB2013/053410, filed 20 Dec. 2013, which claims priority to and the benefit of Great Britain Patent Application No. GB 1223386.2 filed 24 Dec. 2012, the entire contents of which are incorporated herein by reference.

REFERENCE TO AN ELECTRONIC SEQUENCE LISTING

This application hereby incorporates by reference in its entirety the material of the electronic Sequencing Listing XML (IPF05US3_SeqList.xml" created on 12/12/2022, which has a file size of 290,190 bytes) filed concurrently herewith.

FIELD OF THE INVENTION

The present invention relates to an immunogenic HBV peptide composition and to the treatment of HBV using the composition.

BACKGROUND OF THE INVENTION

Hepatitis B virus (HBV) infection is a major cause of liver-related morbidity and mortality in Europe and worldwide. An estimated 650,000 individuals die each year from liver failure or hepatocellular carcinoma. Even though vaccination programs have led to declines in de novo HBV infections in many countries, chronic hepatitis B (CHB) is a rapidly growing problem in Europe due to immigration of HBV carriers from endemic areas.

From a conceptual standpoint, chronic HBV infection can be classified into three phases (or types of immune responses): immune tolerant, immune active and inactive chronic carrier. These distinct phases of chronic infection correspond with characteristic serologic patterns and correlate with the patient's immune response to HBV. In general, patients with persistent immune active chronic HBV infection receive HBV therapy.

Limited treatment options are available for chronic hepatitis B (CHB). Suppression of viral replication with antivirals such as interferon-alpha and nucleoside/nucleotide analogues (NICs) is the only way to reduce morbidity and mortality from chronic HBV infection with the ultimate aim of improving survival. Nevertheless, the loss of serum HBsAg and development of anti-HBs antibodies (seroconversion) is the hallmark of a successful immunological response to HBV infection and the closest outcome to clinical cure. Only interferon-alpha has been able to induce significant HBsAg loss but in a relatively low proportion of patients (10%). Interferons have a high cost, a poor tolerability and some HBV genotypes remain poorly responsive to treatment.

Consequently, NUCs remain the main treatment strategies with five NUCs being approved in Europe to treat CHB. The most potent and preferred drugs, tenofovir and entecavir, have a very favorable side-effect profile and are able to induce HBV DNA suppression in almost all patients. However, life-long therapy is required for the majority of patients under most national and international guidelines. Only very few HBeAg-positive patients, and no HBeAg-negative patients, are able to clear HBsAg even after several years of NUC therapy. The long-term safety of NUC therapy is currently unknown. Therefore, concepts to enable a timely cessation of NUC therapy are urgently needed.

Therapeutic vaccination is a promising intervention for hepatitis B as a way to induce immune control over the disease. T-cell responses have been shown to be critical for clearance of acute HBV infection. However, therapeutic HBV vaccines based on HBsAg have failed to show benefit due to induced immune tolerance from high levels of circulating HBsAg, even under effective antiviral treatment.

SUMMARY OF THE INVENTION

The present inventors have identified regions of the HBV proteome that have a high degree of conservation between different HBV genotypes and that have unexpectedly better immunogenic properties compared to other similarly conserved regions of HBV proteins. In particular, the inventors have unexpectedly shown using an in vitro assay that peptide sequences within particular domains of HBV polymerase and HBV core protein are able to elicit a response in PBMC from chronically infected HBV patients infected with different HBV genotypes and/or from chronically infected HBV patients of different ethnicities. In particular, the inventors have surprisingly identified an immunodominant region in the terminal domain of HBV polymerase.

Accordingly, the present invention provides a pharmaceutical composition comprising at least two peptides of from 15 to 60 amino acids in length, selected from peptides comprising a sequence of at least 15 contiguous amino acids of one of the sequences shown in SEQ ID NOs: 1 to 4 or of a sequence having at least 80% identity to one of the sequences shown in SEQ ID NOs: 1 to 4, wherein each peptide comprises at least one CD8+ T-cell epitope and/or at least one CD4+ T-cell epitope and wherein each peptide elicits a response in peripheral blood mononuclear cells (PBMC) from at least one chronically infected HBV individual in an in vitro assay.

The composition may comprise at least one peptide comprising at least 15 amino acids of one of the sequences shown in SEQ ID NOs: 1 to 3 and at least one peptide comprising at least 15 amino acids of the sequence shown in SEQ ID NO: 4.

At least one of the peptides may comprise a sequence shown in one of SEQ ID NOs: 24 to 33, or a sequence having at least 80% identity to one of the sequences shown in SEQ ID NOs: 24 to 33. One or more of the peptides may comprise one or more amino acid(s) at the N-terminus and/or C-terminus to increase the net positive charge and/or to reduce hydrophobicity of the peptide. The composition may therefore comprise a peptide comprising a sequence shown in one of SEQ ID NOs: 34 to 38.

The composition may further comprise at least one peptide derived from HBV surface protein. The peptides derived from HBV surface protein may be of from 15 to 60 amino acids in length and comprise a sequence of at least 15 contiguous amino acids of the sequence shown in SEQ ID NO: 55 or of a sequence having at least 80% identity to at least 15 contiguous amino acids of the sequence shown in SEQ ID NO: 55, wherein the peptide comprises at least one CD8+ T-cell epitope and/or at least one CD4+ T-cell epitope and elicits a response in peripheral blood mononuclear cells (PBMC) from at least one chronically infected HBV individual in an in vitro assay.

The composition, wherein said composition is capable of eliciting an immune response in PBMC from at least two individuals of different ethnicities and from two individuals infected with different HBV genotypes.

The composition may be capable of eliciting an immune response: (a) in PBMC from two, three or all of: an individual infected with HBV genotype A, an individual infected with HBV genotype B, an individual infected with HBV genotype C and an individual infected with HBV genotype D; and/or in PBMC from two, three or all of: an Oriental or Indian individual infected with HBV, a Caucasian individual infected with HBV and an African or Arabic individual infected with HBV.

The peptides in a composition of the invention may be linked to a fluorocarbon vector. The composition may further comprise HBc, HBe, or HBs antigen and/or an adjuvant.

The invention provides the composition of the invention for use in the treatment or prevention of HBV infection, particularly for the treatment of HBeAg-negative patients or HBeAg-positive patients. The composition of the invention may be used in combination with: (i) interferon-alpha and/or nucleoside/nucleotide analogues (NUCs); and/or (ii) anti-PD1 blocking antibodies, anti-CTLA4 blocking antibodies, anti-PD1L blocking antibodies, anti-LAG3 blocking antibodies, anti-TIM3 blocking antibodies and/or cyclophosphamide. Treatment with the composition may result in HBsAg loss or HBsAg seroconversion.

The invention also provides the composition of the invention for use in the treatment or prevention of end-stage liver disease or hepatocellular carcinoma or for use in the treatment or prevention of hepatitis D virus (HDV) infection.

A method of treating or preventing HBV infection, the method comprising administering to a subject in need thereof a therapeutically effective amount of a composition according to the invention, and the use of a composition according to the invention in the manufacture of a medicament for the treatment or prevention of HBV are also provided.

In addition, the invention provides a peptide of from 15 to 60 amino acids in length comprising at least 15 contiguous amino acids of the sequence shown in anyone of SEQ ID NOs: 1 to 4 or of a sequence having at least 80% identity to one of the sequences shown in SEQ ID NOs: 1 to 4, which peptide comprises at least one CD8+ T-cell epitope and/or at least one CD4+ T-cell epitope and is capable of eliciting a response in peripheral blood mononuclear cells (PBMC) from at least one chronically infected HBV individual in an in vitro assay. The peptide of may comprise at least 15 contiguous amino acids of the sequence shown in SEQ ID NO: 5, 6, 14 or 15.

The invention also provides a peptide comprising one of the sequences shown in SEQ ID NOs: 24 to 38, or a sequence having at least 80% identity to one of the sequences shown in SEQ ID NOs: 24 to 38.

The peptide of the invention may be covalently linked to a fluorocarbon vector.

BRIEF DESCRIPTION OF THE FIGURES

FIGS. 13A, 13B, 13C, 13D and 13E correspond to results obtained for groups of individuals infected by HBV genotypes A, B, C, D and non-A/B/C/D respectively. Following a 10 day culture with the nine unconjugated HBV peptides (NP113, NP151, NP277(K), NP376, NP753(K), NP797(K), NP856(K), NP877 and NP1266(K)) (0. 1 µg/peptide/mL), PBMC were restimulated in an 18 h IFNγ ELISpot assay with individual peptides at a concentration of 5 µg/ml. Results are expressed as cytokine-producing cells, as a percentage of parent CD3/CD4 or CD3/CD8 T cell populations. Stimulation in culture medium or PMA/ionomycin were used as negative and positive controls respectively and the gating strategy was based on negative control IFNγ production.

BRIEF DESCRIPTION OF THE SEQUENCE LISTING

Figure 1:
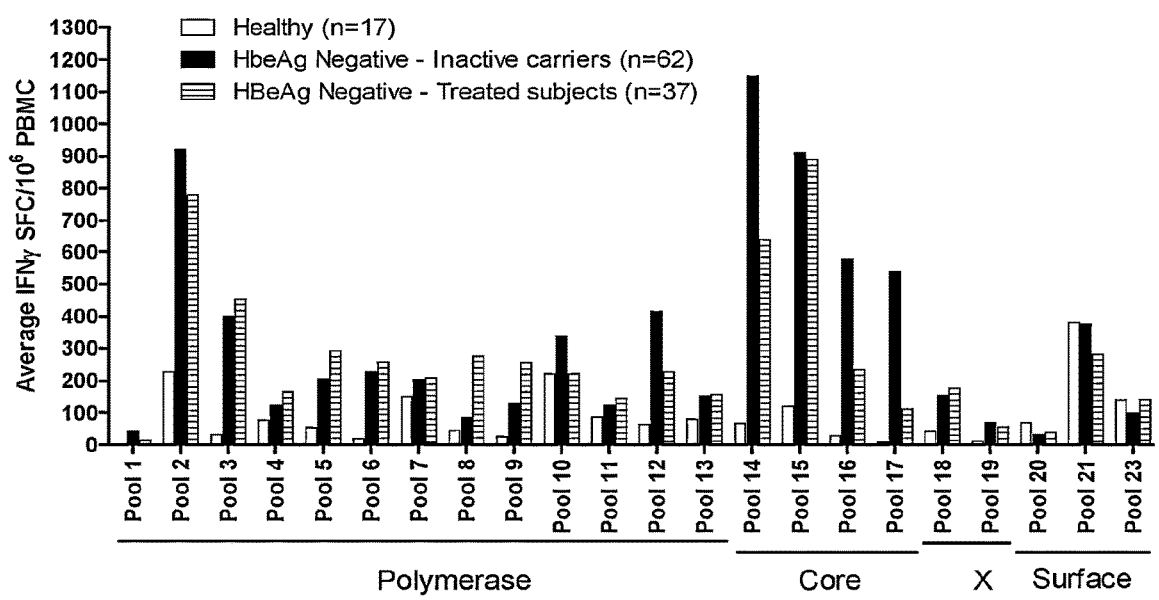
FIG. 1 is a comparison of IFNγ responses in chronic HBV-infected subjects in immune control phase or undergoing active treatment. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

SEQ ID NOs: 1 to 38 and 40 to 72 are the amino acid sequences of regions of the reference HBV sequence shown in SEQ ID NO: 39 of HBV polymerase as shown in Table 1 below.

| SEQ ID NO: | Reference in Examples | Region of virtual HBV proteome sequence | HBV protein |
|---|---|---|---|
| 1 | Pools 2/3 | 93-186 | polymerase |
| 2 | Pools 4 to 7 | 211-426 | polymerase |
| 3 | Pools 12 and 13 | 592-700 | polymerase |
| 4 | Pools 14 to 17 | 703-912 | core |
| 5 | Pool 2 | 93-145 | polymerase |
| 6 | Pool 3 | 133-186 | polymerase |
| 7 | Pool 5 + additional N-terminal residues | 260-326 | polymerase |
| 8 | Pool 6 | 332-384 | polymerase |
| 9 | Pools 6/7 | 332-426 | polymerase |
| 10 | Pools 14/15 | 703-812 | core |
| 11 | Pools 15/16 | 749-871 | core |
| 12 | Pools 16/17 | 811-912 | core |
| 13 | Pool 17 | 859-912 | core |
| 14 | Pool 25 | 93-132 | polymerase |
| 15 | Pool 26 | 133-171 | polymerase |
| 16 | Pool 28 + additional N-terminal residues | 260-301 | polymerase |
| 17 | Pool 30 | 332-378 | polymerase |
| 18 | Pool 31 | 359-398 | polymerase |
| 19 | Pool 35 | 626-663 | polymerase |
| 20 | Pool 38 | 738-775 | core |
| 21 | Pool 39/40 | 778-837 | core |
| 22 | Pool 42 | 838-878 | core |
| 23 | Pool 43 | 859-891 | core |
| 24 | P113 | 96-130 | polymerase |
| 25 | P151 | 134-168 | polymerase |
| 26 | P277 | 260-295 | polymerase |
| 27 | P360 | 342-378 | polymerase |
| 28 | P376 | 359-398 (C to S substitution at 393) | polymerase |
| 29 | P645 | 627-662 | polymerase |
| 30 | P753 | 738-770 (S to T substitution at 743) | core |
| 31 | P797 | 780-814 (C to S substitution at 793) | core |
| 32 | P856 | 839-873 | core |
| 33 | P877 | 860-890 | core |
| 34 | P277(K) | 260-293 + KKK | polymerase |
| 35 | P645(K) | KKK + 627-662 | core |
| 36 | P753(K) | KK + 738-770 (S to T at 743) + KKK | core |
| 37 | P797(K) | 780-814 (C to S at 792) + KKK | core |
| 38 | P856(K) | 839-873 + KKK | core |
| 40 | Pool 1 | 25-79 | polymerase |
| 41 | Pool 4 | 211-261 | polymerase |
| 42 | Pool 7 | 372-426 | polymerase |
| 43 | Pool 8 | 414-465 | polymerase |
| 44 | Pool 9 | 473-531 | polymerase |

-continued

| SEQ ID NO: | Reference in Examples | Region of virtual HBV proteome sequence | HBV protein |
|---|---|---|---|
| 45 | Pool 10 | 520-569 | polymerase |
| 46 | Pool 11 | 557-604 | polymerase |
| 47 | Pool 12 | 592-650 | polymerase |
| 48 | Pool 13 | 638-700 | polymerase |
| 49 | Pool 14 | 703-762 | core |
| 50 | Pool 15 | 749-812 | core |
| 51 | Pool 16 | 811-871 | core |
| 52 | Pool 18 | 966-1017 | X |
| 53 | Pool 19 | 1005-1062 | X |
| 54 | Pool 20 | 1171-1224 | surface |
| 55 | Pool 21 | 1241-1296 | surface |
| 56 | Pool 22 | 1312-1346 | surface |
| 57 | Pool 23 | 1392-1447 | surface |
| 58 | Pool 24 | 31-79 | polymerase |
| 59 | Pool 27 | 223-261 | polymerase |
| 60 | Pool 28 | 265-301 | polymerase |
| 61 | Pool 29 | 289-326 | polymerase |
| 62 | Pool 32 | 404-440 | polymerase |
| 63 | Pool 33 | 428-465 | polymerase |
| 64 | Pool 34 | 557-597 | polymerase |
| 65 | Pool 36 | 645-685 | polymerase |
| 66 | Pool 37 | 659-700 | polymerase |
| 67 | Pool 39 | 778-812 | core |
| 68 | Pool 40 | 811-837 | core |
| 69 | Pool 41 | 811-850 | core |
| 70 | Pool 44 | 979-1024 | X |
| 71 | Pool 45 | 1247-1289 | surface |
| 72 | Pool 46 | 1399-1439 | surface |
| 220 | Pool 5 | 265-326 | polymerase |
| 221 | P1266 | 1252-1284 (K to R at 1266) | surface |
| 222 | P1266 | (K) KKK + 1252-1284 (K to R at 1266) + KKK | surface |

SEQ ID NO: 39 is a virtual HBV protein sequence built by linear coassembly of the terminal domain of polymerase (positions 1 to 181), the reverse transcriptase domain of polymerase (position 182 to 549) the RNase domain H of polymerase (position 550 to 702), the core protein (position 703 to 914), the X protein (position 915 to 1068) and the surface protein (positions 1069 to 1468). The proteome sequence was obtained from consensus of consensus sequences generated from genotype A, B, C and D consensus sequences. SEQ ID NOs: 73 to 219 are the amino acid sequences of short peptides within each of pools 1 to 46. SEQ ID NO: 220 is the amino acid sequence of pool 5.

DETAILED DESCRIPTION OF THE INVENTION

Peptide Composition

The present invention provides a composition comprising broadly immunogenic peptide sequences capable of eliciting multiepitopic CD4+ and CD8+ T-cell immune responses with broad applicability in terms of population coverage and HBV genotype coverage. The present invention provides a pharmaceutical composition comprising at least one peptide from 15 to 60 amino acids in length, wherein said peptide comprises a fragment of at least 15 contiguous amino acids of the terminal domain of HBV polymerase, reverse transcriptase domain of HBV polymerase, RNase H domain sequence of HBV polymerase or HBV core protein. The peptide is of from 15 to 60 amino acids in length and is selected from peptides comprising a sequence of at least 15 contiguous amino acids of one of the sequences shown in SEQ ID NOs: 1 to 4. The peptide comprises at least one CD8+ T-cell epitope and/or at least one CD4+ T-cell epitope. The peptide elicits a response in peripheral blood mononuclear cells (PBMC) from at least one chronically infected HBV individual in an in vitro assay.

The composition may comprise multiple peptides having the properties defined above. The composition may be capable of eliciting an immune response in peripheral blood mononuclear cells (PBMC) from at least two individuals of different ethnicities and/or from two individuals infected with different HBV genotypes.

Peptide Sequences

The composition of the invention may comprise one or more peptides comprising at least 15 contiguous amino acids, such as at least 20, 25, 29, 30, 31, 32, 33, 34 or 35 amino acids from one of SEQ ID NOs: 1 to 4. SEQ ID NOs: 1, 2 and 3 are HBV polymerase sequences. SEQ ID NO: 4 is an HBV core protein sequence.

These regions may be further subdivided so that a peptide present in the composition of the invention may comprise at least 15, 20, 25, 30, 32, 33, 34 or 35 amino acids from one of SEQ ID NOs: 5 to 13. Preferably, peptides from within these subregions contain sequences within one of SEQ ID NOs: 14 to 23.

Exemplary short peptides within SEQ ID NOs: 1 to 4 are shown in SEQ ID NOs: 80 to 117 and 142 to 184. Preferred exemplary short peptides are shown in SEQ ID NOs: 80 to 83, 86 to 89, 98 to 101, 105 to 112, 146 to 150, 163 to 166 and 169 to 181. A composition of the invention may comprise a peptide comprising one or more of these short sequences.

Particularly preferred peptides from these HBV polymerase sequences comprise one of the sequences shown in SEQ ID NOs: 24 to 29. SEQ ID NO: 24 is a preferred region of SEQ ID NOs: 1, 5 and 14. SEQ ID NO: 25 is a preferred region of SEQ ID NOs: 1, 6 and 15. SEQ ID NO: 26 is a preferred region of SEQ ID NOs: 2, 7 and 16. SEQ ID NOs: 27 is a preferred region of SEQ ID NOs: 2, 8 and 17. SEQ ID NO: 28 is a preferred region of SEQ ID NOs: 2, 9 and 18. SEQ ID NO: 29 is a preferred region of SEQ ID NOs: 3 and 19.

Particularly preferred peptides from the above HBV core protein sequence (SEQ ID NO: 4) comprise one of the sequences shown in SEQ ID NOs: 30 to 33. SEQ ID NO: 30 is a preferred region of SEQ ID NOs: 10 and 20. SEQ ID NO: 31 is a preferred region of SEQ ID NOs: 11 and 21. SEQ ID NO: 32 is a preferred region of SEQ ID Nos: 12 and 22. SEQ ID NO: 33 is a preferred region of SEQ ID NOs: 13 and 23.

Other preferred peptides are comprised within the sequences shown in SEQ ID NOs: 24 to 33 and include peptides comprising at least 20, such as 25, 29, 30, 31, 32, 33 or 34 contiguous amino acids from within one of these sequences.

The composition may further comprise at least one peptide of from 15 to 60 amino acids in length, wherein said peptide comprises a fragment of at least 15 contiguous amino acids of HBV surface protein. The HBV surface protein peptide is typically of from 15 to 60 amino acids in length and is selected from peptides comprising a sequence of at least 15 contiguous amino acids of the sequence shown in SEQ ID NO: 55.

The HBV surface protein peptide may comprise at least 15, 20, 25, 30, 32, 33, 34 or 35 amino acids from one of SEQ ID NOs: 55, and preferably from SEQ ID NO: 71.

Exemplary short peptides within SEQ ID NOs: 55 and 71 are shown in SEQ ID NOs: 204 to 210 and 205 to 209, respectively. A composition of the invention may comprise a peptide comprising one or more of these short sequences.

Particularly preferred peptides from these HBV surface protein sequences comprise one of the sequences shown in SEQ ID NOs: 221. SEQ ID NO: 221 is a preferred region of SEQ ID NOs: 55 and 71.

Still further peptides that may be included in compositions of the invention are peptides that comprise a sequence that comprises one or more, such as two, three or four, amino acid substitutions, additions or deletions, preferably substitutions, within one of the sequences shown in one of SEQ ID NOs: 1 to 33, 55, 71 and 221. One, two, three or more amino acids within the contiguous sequence may be substituted. Substitutions within the specified sequences include mutations to remove cysteine residues. For example, cysteine residues may be substituted by serine residues.

Typically such peptides will have a sequence identity of at least 80%, such as at least 85%, 90%, 95% or 98% to at least 15 or 20, such as 25, 29, 30, 31, 32, 33, 34, 35, 36, 37, 38, 39 or 40, contiguous amino acids within one of SEQ ID NOs: 1 to 33, 55, 71 and 221, or to the entire length of one of the sequences shown in SEQ ID NOs: 24 to 33 and 221 (for example, as determined using the BLAST program available at the National Center for Biotechnology Information (blast.ncbi.nlm.nih.gov/Blast.cgi)). Such peptides include sequences that match the amino acid sequence of HBV genotype A, B, C, D, E or F in the equivalent region of the HBV polymerase or core protein.

The peptides may comprise additional sequences, provided that their overall length does not exceed 60 amino acids. For example, the peptide may comprise at least 20, such as 25, 29, 30, 31, 32, 33, 34 or 35 contiguous amino acids from within one of the sequences shown in one of SEQ ID NOs: 1 to 33, 55, 71 and 221, preferably SEQ ID NOs: 24 to 33 and 221 and may have a length of from 15, 20 or 25 amino acids up to 30, 31, 32, 33, 34, 35, 36, 37, 38, 39, 40, 45, 50, 55 or 60 amino acids.

Thus, the peptide typically has a length of from 15 or 20 to 60 amino acids, such as from 25 to 50 amino acids, preferably from 30 to 40 amino acids, for example, 31, 32, 33, 34, 35, 36, 37, 38 or 39 amino acids.

The peptide may include additional sequences. The additional sequences may facilitate manufacture or formulation of the peptide or enhance stability of the peptide. For example, the peptide may comprise one or more additional amino acids, typically at the N-terminus and/or the C-terminus to enhance the net positive charge of the peptide and/or to reduce the hydrophobicity of the peptide. The net positive charge may be increased so that the peptide has an isoelectric point greater than or equal to 7.

In one aspect of the invention, one or more, such as two or three positively charged amino acids (arginine and/or lysine) are added to the N- and/or C-terminus of one or more of the peptides in the composition. For example, three lysine residues may be added to the N- and/or C-terminus of one or more of the peptides. Positive amino acids are typically added at the end(s) of peptides that have an overall hydrophobicity of more than 65%, a net charge of less than zero and/or include cluster of hydrophobic amino acids.

Particular examples of peptides that include N- and/or C-terminal lysine residues are shown in SEQ ID NOs: 34 to 38 and 222.

The peptide may comprise one or more epitope that is not present in a consensus HBV sequence. One such example is the use of fusion peptides where a promiscuous T helper epitope is covalently linked (optionally via a polypeptide linker or spacer) to the consensus sequence. As an example, the promiscuous T helper epitope can be the PADRE peptide, tetanus toxoid peptide (830-843) or influenza haemagglutinin, HA(307-319).

Where the peptide is linked to a fluorocarbon, the terminus of the peptide, such as the terminus that is not conjugated to the fluorocarbon, or other attachment, can be altered, for example to promote solubility of the fluorocarbon-peptide construct via the formation of micelles. To facilitate large-scale synthesis of the construct, the N- or C-terminal amino acid residues of the peptide can be modified. When the desired peptide is particularly sensitive to cleavage by peptidases, the normal peptide bond can be replaced by a non-cleavable peptide mimetic. Such bonds and methods of synthesis are well known in the art.

The peptide may be a native peptide. The peptide may be modified to increase longevity, such as half-life or persistence at the site of administration, of the peptide in vivo or to direct the peptide to antigen-presenting cells. For example, the immunogenic peptide can contain one or more non-naturally occurring amino acids and/or non-naturally occurring covalent bonds for covalently connecting adjacent amino acids. In certain embodiments, the non-standard, non-naturally occurring amino acids can also be incorporated into the immunogenic peptides provided that they do not interfere with the ability of the peptide to interact with MHC molecules and remain cross-reactive with T-cells recognising the natural sequences. Non-natural amino acids can be used to improve peptide resistance to protease or chemical stability. Examples of non-natural amino acids include D-amino acids and cysteine modifications.

The peptide may be coupled to a carrier, such as a protein carrier or a delivery vector. Suitable delivery vectors include lipopeptides, for example fatty acyl chains such as a monopalmitoyl chain, virosomes, liposomes and cell penetrating peptides, such as penetrating and transactivator of transcription (TAT).

One or more, and preferably all, of the HBV peptides in the composition of the invention are preferably covalently linked to a fluorocarbon vector.

Combinations of Peptides

A composition of the invention may comprise multiple peptides. Accordingly, the composition may comprise at least two, such as at least three, four, five, six, seven, eight, nine, ten or more peptides, each comprising a sequence of at least 15 contiguous amino acids of one of SEQ ID NOs: 1 to 4 as described above. The composition may additionally comprise a peptide comprising a sequence of at least 15 contiguous amino acids of SEQ ID NO: 55 as described above.

In one aspect, the composition may comprise at least one peptide comprising at least 15 amino acids of one of the sequences shown in SEQ ID NOs: 1 to 3 and at least 15 amino acids of the sequence shown in SEQ ID NO: 4, and optionally at least one peptide comprising at least 15 amino acids of one of the sequences shown in SEQ ID NO: 55. For example, the composition may comprise at least one peptide comprising at least 15 amino acids of one of the sequences shown in SEQ ID NOs: 24, 25, 26, 27, 28, 29 and 34 and at least 15 amino acids of one of the sequences shown in SEQ ID NOs: 30 to 33 and 35 to 38.

In another aspect, the composition may comprise at least one peptide comprising a sequence of at least 15 contiguous amino acids of one of SEQ ID NOs: 1 and/or 2 as described above and at least one peptide comprising a sequence of at least 15 contiguous amino acids of SEQ ID NO: 3 or 4 as described above. For example, the composition may comprise a peptide comprising a sequence of at least 15 contiguous amino acids of SEQ ID NO: 1 or 2 (or peptides comprising sequences of both SEQ ID NOs: 5 and 6) as described above and a peptide comprising at least 15 contiguous amino acids of anyone of SEQ ID NOs: 10 to 13 as described above. The invention may comprise peptides comprising a sequence of at least 15 contiguous amino acids of any two, three, four, five or all of SEQ ID NOs: 5, 6, 7, 8 and 9 as described above and/or may comprise peptides comprising a sequence of at least 15 contiguous amino acids of any two, three or all of SEQ ID NOs: 10 to 13 as described above.

A peptide present in a composition of the invention may consist of, or consist essentially of, one of the sequences shown in SEQ ID NOs: 24 to 38. A HBV surface protein peptide present in a composition of the invention may consist of, or consist essentially of, one of the sequences shown in SEQ ID NOs: 221 and 222. The invention thus provides a pharmaceutical composition comprising at least one peptide, such as two or more peptides that consist of, consist essentially of or comprise the amino acid sequence shown in one of SEQ ID NOs: 24 to 38, and optionally at least one peptide that consists of, consists essentially of or comprises the amino acid sequence shown in SEQ ID NOs: 221 or 222. The composition may comprise at least two, such as three, four, five, six, seven, eight, nine or ten peptides comprising the sequences shown in SEQ ID NOs: 24 to 33 and 221. In one embodiment, one or more of the peptides comprising one of SEQ ID NOs: 24 to 33 and 221 may comprise N- or C-terminal lysine residues. More particularly the peptides comprising SEQ ID NOs: 26, 29, 30, 31, 32 and 221 may have the sequences shown in SEQ ID NOs: 34 to 38 and 222, respectively.

For example, the composition may comprise at least two, such as three, four, five, six, seven, eight, nine or ten of the peptides comprising, consisting of, or consisting essentially of the sequences shown in SEQ ID NOs: 24, 25, 27, 28, 33, 34, 35, 36, 37 and 38, or at least two, such as three, four, five, six, seven or eight of the peptides comprising, consisting of, or consisting essentially of SEQ ID NOs: 24, 25, 28, 33, 34, 36, 37 and 38. Any possible combination of these peptides may be present in a composition of the invention. Preferred combinations include one or more, such as any two, any three, any four or all, of SEQ ID NOs: 24, 25, 28, 33 and 31/37, preferably SEQ ID NO: 24 and/or 25. For example, a combination of SEQ ID NO: 24 and 33 results in a composition containing epitopes that bind to seven class I alleles and seven class II alleles. The composition may further comprise a peptide comprising, consisting of, or consisting essentially of SEQ ID NO: 221 or 222.

For example, the composition may comprise eight peptides comprising the following sequences: SEQ ID NOs: 24, 25, 26, 28, 30, 31, 32 and 33, and optionally a ninth peptide comprising SEQ ID NO: 222.

One of the peptides, such as the peptide comprising SEQ ID NO: 28, may be substituted by a peptide comprising SEQ ID NO: 27 and/or one peptide may be substituted by a peptide comprising SEQ ID NO: 29. One or more of the peptides may be substituted with a shorter peptide as described above, for example a peptide having at least 20 contiguous amino acids of the substituted peptide or with a peptide having at least 80% identity to the amino acid sequence of the substituted peptide across its entire length.

Preferably, the composition comprises at least one peptide from HBV polymerase as described above, more preferably from the terminal domain of HBV polymerase. In a particularly preferred embodiment, the HBV polymerase peptide comprises at least one amino acid sequence within SEQ ID NO: 1, such as at least one sequence within SEQ ID NO: 5, 6, 14, 15, 24 or 25. For example, such peptides may comprise the amino acid sequence shown in one of SEQ ID NOs: 80, 81, 82, 83, 86, 87, 88, 89, 24 or 25.

HBV Genotypes

The combination of peptide sequences in the composition provides epitopes, preferably both CD8+ and CD4+ epitopes, present in multiple HBV genotypes. HBV genotypes include genotypes A, B, C, D, E and F. For example, the long peptides may comprise epitopes from at least two HBV genotypes, such as A and D (the most highly prevalent genotypes in Europe) or B and C (the most highly prevalent genotypes in Asia). More preferably, the composition comprises epitopes from at least three HBV genotypes, such as for example, A, B and C, A, B and D, A, C and D or B, C and D. Most preferably, the composition comprises epitopes from at least HBV genotypes A, B, C and D. In addition to including any combination of epitopes from any combination of one or more of genotypes A, B, C and D, the composition may comprise epitopes to genotypes E, F and/or G. This may be determined by any suitable means, for example by using an in vitro PBMC assay as described herein.

Thus, the present invention provides a composition capable of eliciting an immune response in PBMC from two, three, four or all of: an individual infected with HBV genotype A, an individual infected with HBV genotype B, an individual infected with HBV genotype C, an individual infected with HBV genotype D and an individual infected with another HBV genotype.

A composition of the invention that is capable of eliciting an immune response in two, three or all of: an individual infected with HBV genotype A, an individual infected with HBV genotype B, an individual infected with HBV genotype C and an individual infected with HBV genotype D may comprise at least one peptide selected from at least two, preferably three or all of the following groups:
  (i) a peptide comprising at least 15 contiguous amino acids of SEQ ID NO: 14, 15, 20, 21, 67, 22 or 23;
  (ii) a peptide comprising at least 15 contiguous amino acids of SEQ ID NO: 14, 17, 18, 21 or 67;
  (iii) a peptide comprising at least 15 contiguous amino acids of SEQ ID NO: 14, 16, 60, 19, 20 or 22; and
  (iv) a peptide comprising at least 15 contiguous amino acids of SEQ ID NO: 14, 15, 20, 21, 67, 22 or 23.

The composition may further comprise a peptide comprising at least 15 contiguous amino acids of SEQ ID NO: 55 or SEQ ID NO: 71.

For example, such a composition may comprise a peptide selected from at least two, preferably three or all of the following groups:
  (i) a peptide comprising at least 15 contiguous amino acids of SEQ ID NO: 20, 21, 67, 22 or 23;
  (ii) a peptide comprising at least 15 contiguous amino acids of SEQ ID NO: 17 or 18;
  (iii) a peptide comprising at least 15 contiguous amino acids of SEQ ID NO: 16, 60 or 19; and
  (iv) a peptide comprising at least 15 contiguous amino acids of SEQ ID NO: 14 or 15.

The composition may further comprise a peptide comprising at least 15 contiguous amino acids of SEQ ID NO: 55 or SEQ ID NO: 71.

Suitable peptides comprising at least 15 amino acids of the specified sequences are described in more detail herein and include, in particular, the peptides of SEQ ID NOs: 24 to 38 mentioned in Table 4 and the peptides of SEQ ID NOs: 221 and 222.

In one aspect, the composition of the invention elicits an in vitro response in peripheral blood mononuclear cells (PBMC) from at least one individual chronically infected with HBV genotype A, one individual chronically infected with HBV genotype B, one individual chronically infected with HBV genotype C and one individual chronically infected with HBV genotype D. This may be determined by any suitable method, such as a method described in the Examples herein. The individuals may be of the same or different ethnicities, preferably from at least two different ethnicities. The individuals may be of the same or different HLA subtypes, preferably at least two different HLA subtypes.

Ethnicities

The invention provides a composition capable of eliciting an immune response in individuals of at least two, such as three or more different ethnicities. This can be assessed using an in vitro PBMC assay as described in the Examples. The composition of the invention may be capable of eliciting an immune response in PBMC from two, three or all of: an Oriental or Indian individual infected with HBV, a Caucasian individual infected with HBV and an African or Arabic individual infected with HBV.

A composition of the invention that is capable of eliciting an immune response in two, three or all of: an Oriental or Indian individual infected with HBV, a Caucasian individual infected with HBV and an African or Arabic individual infected with HBV may comprise at least one peptide selected from at least two, preferably three or all of the following groups:
  (i) a peptide comprising at least 15 contiguous amino acids of SEQ ID NO: 14, 16, 60, 17, 18, 20, 21, 67 or 22;
  (ii) a peptide comprising at least 15 contiguous amino acids of SEQ ID NO: 14, 15, 19, 20, 22 or 23; and
  (iii) a peptide comprising at least 15 contiguous amino acids of SEQ ID NO: 14, 15, 20, 21, 67, 22 or 23.

The composition may further comprise a peptide comprising at least 15 contiguous amino acids of SEQ ID NO: 55 or SEQ ID NO: 71.

For example, such a composition may comprise a peptide selected from at least two, preferably three or all of the following groups:
  (i) a peptide comprising at least 15 contiguous amino acids of SEQ ID NO: 16, 60, 17, 18;
  (ii) a peptide comprising at least 15 contiguous amino acids of SEQ ID NO: 14, 15 or 19; and
  (iii) a peptide comprising at least 15 contiguous amino acids of SEQ ID NO: 14, 15, 20, 21, 22 or 23.

The composition may further comprise a peptide comprising at least 15 contiguous amino acids of SEQ ID NO: 55 or SEQ ID NO: 71.

Suitable peptides comprising at least 15 amino acids of the specified sequences are described in more detail herein and include, in particular, the peptides of SEQ ID NOs: 24 to 38 mentioned in Table 4 and the peptides of SEQ ID NOs: 221 and 222.

Epitopes

HLA class I and class II molecules are polymorphic and their frequency varies between ethnic groups. Most of the polymorphism is located in the peptide-binding region, and as a result each variant is believed to bind a unique repertoire of peptide ligands. HLA polymorphism represents a major challenge for vaccine designers since HLA polymorphism is the basis for differential peptide binding. Moreover, specific HLA alleles are expressed at dramatically different frequencies in different ethnicities.

Despite such polymorphisms, HLA molecules bind overlapping set of peptides, and therefore, may be grouped accordingly into supertypes (Lund et al (2004) Immunogenetics 55(12):797-810, Sette et al (1999) Immunogenetics 50(3-4):201-212). A supertype is defined as a family of different HLA molecules having similar peptide binding repertoire and consequently sharing overlapping sets of peptides. In other words, a peptide that binds to an HLA allele belonging to a given supertype is likely to present a binding activity to the other supertype members.

Binding capacity of the peptides for different HLA class II alleles can be determined using a heterologous competitive assay using a specific biotinylated tracer peptide for each HLA class II allele as described in Texier et al (2000) J Immunol 164:3177-3184, Texier et al (2001) Eur J Immunol 31: 1837-1846 and Castelli et al (2002) J Immunol 169:6928-6934.

The following nine HLA class II alleles represent major supertypes or HLA clusters based on sequences analysis and binding-motif specificities as described in Lund et al (2004) Immunogenetics 55(12):797-810 and Greenbaum et al (2011) Immunogenetics 63(6):325-35: HLA-DR1 ($\alpha1*01$: $01;\beta1*01:01$), HLA-DR3 ($\alpha1*01:01;\beta1*03:01$), HLA-DR4 ($\alpha1*01:01;\beta1*04:01$), HLA-DR7 ($\alpha1*01:01;\beta1*07:01$), HLA-DR11 ($\alpha1*01:01;\beta1*11:01$), HLA-DR13 ($\alpha1*01:01;\beta1*13:01$), HLA-DR15 ($\alpha1*01:01;\beta1*15:01$), HLA-DR51 ($\alpha1*01:01;\beta5*01:01$) and HLA-DP4 ($\alpha1*01:03;\beta1*04:01$). These alleles have a high prevalence across different ethnicities (see Wilson et al (2001) J Virol. 75(9):4195¬4207).

A peptide present in a composition of the invention typically binds to at least two, preferably at least three, of the nine major HLA class II alleles, such as to at least two, preferably at least three, of the seven HLA class II alleles described in Example 10. One or more of the peptides present in the composition may bind to at least four, five, six, seven, eight or all of the nine major HLA class II alleles or to at least four, five, six or all of the seven HLA class II alleles described in Example 10. The composition of the invention preferably comprises peptides that can bind to at least seven, at least eight or all nine of the major HLA class II alleles described above, such as to all of the seven HLA class II alleles described in Example 10.

The number of HLA class I binding registers contained in each peptide may be determined by determining the ability of the peptide to bind to a range of frequently occurring HLA class I molecules. HLA class I binding may be measured using the ProImmune REVEAL® MHC-peptide Binding Assay (ProImmune Ltd, Oxford, UK). The REVEAL™ MHC peptide-binding assay measures the ability of each peptide to stabilize the ternary MHC-peptide complex for HLA-A*0101, HLA-A*0201, HLA¬A*0301, HLA-A*2402, HLA-B*0702, HLA-B*0801, HLA-B*3501 representative of main HLA class I supertypes. Each tested peptide is given a score relative to a pass/fail control peptide and also compared to a positive control peptide.

HLA class I molecules bind short peptides having length varying from 8 to 11 amino acids. In theory, 102 short peptides (27×8-mers, 26×9-mers, 25×10-mers & 24×11-mers) could be derived from a 35-mer peptide sequences. In order to limit the number of peptides to be tested, binding assays can be conducted using only nonamer peptides (the most frequent length for HLA class I binding peptides) with a good prediction score based on publically available algorithms.

The following HLA class I alleles are highly represented in human populations and (2) they belong to well-defined HLA supertypes (http://bioinformatics.nmdp.org/): HLA- A*0101, HLA-A*0201, HLA-A*0301, HLA-A*2402, HLA-B*0702, HLA¬B*0801, HLA-B*3501 and HLA-A*1101.

A peptide present in the composition of the invention typically comprises shorter peptides that bind to at least one, preferably at least two or at least three of these HLA class I alleles, such as to the first seven class I alleles listed above and preferably to the seven HLA class I alleles mentioned in Example 9. One or more of the peptides present in the composition may comprise shorter peptides that bind to at least four, five, six or all of the seven HLA class I alleles. The composition of the invention preferably comprises peptides that comprise shorter peptides that can bind to at least five, at least six or all seven of the HLA class I alleles described above.

A pharmaceutical composition of the invention typically comprises one or more peptides comprising one or more T-cell epitopes that bind to different MHC alleles to give broad population coverage. The composition may comprise peptides known or predicted to contain one or more MHC binding motif related to highly frequent MHC alleles in a specific ethnic group or across multiple ethnic groups. The composition may comprise one or more promiscuous CD4+ and CD8+ T-cell epitopes that bind to more than one allelic variant. The combination of peptide sequences in the composition provides T-cell epitopes that bind to different HLA subtypes.

In one aspect, the composition of the invention elicits a response in vitro in peripheral blood mononuclear cells (PBMC) from at least two individuals with different HLA subtypes. The composition may elicit an immune response in at least three, four, five, six or seven individuals each having a different HLA genotype, who may be Individuals of different ethnicities.

Fluorocarbon

The fluorocarbon can comprise one or more chains derived from perfluorocarbon or mixed fluorocarbon/hydrocarbon radicals, and may be saturated or unsaturated, each chain having from 3 to 30 carbon atoms. Thus, the chains in the fluorocarbon attachment are typically saturated or unsaturated, preferably saturated. The chains in the fluorocarbon attachment may be linear or branched, but preferably are linear. Each chain typically has from 3 to 30 carbon atoms, from 5 to 25 carbon atoms, or from 8 to 20 carbon atoms. In order to covalently link the fluorocarbon vector to the peptide, a reactive group, or ligand, for example —CO—, —NH—, S, O or any other suitable group is included in the vector. The use of such ligands for achieving covalent linkages is well known in the art. The reactive group may be located at any position on the fluorocarbon vector.

Coupling of the fluorocarbon vector to the peptide may be achieved through functional groups such as —OH, —SH, —COOH and —NH$_2$, naturally present or introduced onto any site of the peptide. Examples of such linkages include amide, hydrazone, disulphide, thioether and oxime bonds.

Optionally, a spacer element (peptidic or non-peptidic) can be incorporated to permit cleavage of the peptide from the fluorocarbon element for processing within an antigen-presenting cell and to optimize steric presentation of the peptide. The spacer can also be incorporated to assist in the synthesis of the molecule and to improve its stability and/or solubility. Examples of spacers include polyethylene glycol (PEG) or amino acids such as lysine or arginine that may be cleaved by proteolytic enzymes.

In one embodiment, the fluorocarbon-linked peptide can have the chemical structure $C_mF_n$—$C_yH_x$-(Sp)-R or derivatives thereof, where m=3 to 30, n≤2m+1, y=0 to 15, x≤2y, (m+y)=3 to 30 and Sp is an optional chemical spacer moiety and R is an immunogenic peptide. Typically m and n satisfy the relationship 2m−1≤n≤2m+1, and preferably n=2m+1. Typically x and y satisfy the relationship 2y−2≤x≤2y, and preferably x=2y. Preferably the $C_mF_n$—$C_yH_x$ moiety is linear.

It is preferred that m is from 5 to 15, more preferably from 8 to 12. It is also preferred that y is from 0 to 8, more preferably from 0 to 6 or 0 to 4. It is preferred that the $C_mF_n$—$C_yH_x$ moiety is saturated (i.e., n=2m+1 and x=2y) and linear, and that m=8 to 12 and y=0 to 6 or 0 to 4.

In a particular example, the fluorocarbon vector is derived from 2H, 2H, 3H, 3H-perfluoroundecanoic acid of the following formula:

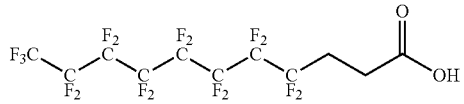

Thus, a preferred fluorocarbon attachment is the linear saturated moiety $C_8F_{17}(CH_2)_2$— which is derived from $C_8F_{17}(CH_2)_2COOH$.

Further examples of fluorocarbon attachments have the following formulae: $C_6F_{13}(CH_2)_2$—, $C_7F_{15}(CH_2)_2$—, $C_9F_{19}(CH_2)_2$—, $C_{10}F_{21}(CH_2)_2$—, $C_5F_{11}(CH_2)_3$—, $C_6F_{13}(CH_2)_3$—, $C_7F_{15}(CH_2)_3$—, $C_8F_{17}(CH_2)_3$— and $C_9F_{19}(CH_2)_3$— which are derived from $C_6F_{13}(CH_2)_2COOH$, $C_7F_{15}(CH_2)_2COOH$, $C_9F_{19}(CH_2)_2COOH$, $C_{10}F_{21}(CH_2)_2COOH$, $C_5F_{11}(CH_2)_3COOH$, $C_6F_{13}(CH_2)_3COOH$, $C_7F_{15}(CH_2)_3COOH$, $C_8F_{17}(CH_2)_3COOH$ and $C_9F_{19}(CH_2)_3COOH$ respectively. Preferred examples of suitable structures for the fluorocarbon vector-antigen constructs have the formula:

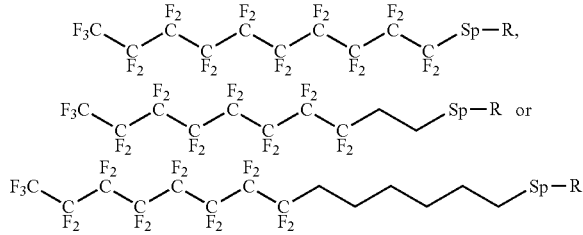

in which Sp and R are as defined above. In certain embodiments Sp is derived from a lysine residue and has the formula —CONH—$(CH_2)_4$—$CH(NH_2)$—CO—. Preferably R is any one of SEQ ID NOs: 1 to 14, preferably R is anyone of SEQ ID NOs: 1 to 6. The amino group of the N-terminal amino acid of each peptide, for example, SEQ ID NO: 1, 2, 3, 4, 5 or 6, forms an amide linkage with the C-terminal carboxy group of the spacer of formula —CONH—$(CH_2)_4$—$CH(NH_2)$—CO—.

In the context of the current invention, the fluorocarbon attachment may be modified such that the resulting compound is still capable of delivering the peptide to antigen presenting cells. Thus, for example, a number of the fluorine atoms may be replaced with other halogen atoms such as chlorine, bromine or iodine. In addition, it is possible to replace a number of the fluorine atoms with methyl groups and still retain the properties of the molecule described herein.

The peptides may be linked to the fluorocarbon vector via a spacer moiety. The spacer moiety is preferably a lysine residue. This spacer residue may be present in addition to any terminal lysine residues as described above, so that the peptide may, for example, have a total of four N-terminal lysine residues. Accordingly, the preferred formulation of the invention may comprise fluorocarbon-linked peptides in which the peptides have a C-terminal or N-terminal lysine residue, preferably an N-terminal lysine residue. The terminal lysine in the peptides is preferably linked to a fluorocarbon having the formula $C_8F_{17}(CH_2)_3COOH$. The fluorocarbon is preferably coupled to the epsilon chain of the N-terminal lysine residue.

It is contemplated that the pharmaceutical compositions described herein comprise at least 1, 2, 3, 4, 5, 6, 7, 8, 9 or 10 or more immunogenic peptides optionally each covalently linked to its own fluorocarbon vector.

Peptides

The present invention also provides a peptide that is useful in a composition of the invention. The peptide may be anyone of the peptides described above. In particular, the invention provides a peptide of up to 40, 50 or 60 amino acids in length comprising one of the sequences shown in SEQ ID NOs: 24 to 33 and 221 or a sequence that is at least 80% identical, such as at least 85%, 90%, 95% or 98% identical, to one of the sequences shown in SEQ ID NOs: 24 to 33 and 221. The peptide may include additional amino acids as described above. In one particular embodiment, the invention provides a peptide having the sequence shown in one of SEQ ID NOs: 34 to 38 and 222. Particularly preferred peptides of the invention comprise, consist essentially of, or consist of the sequences shown in SEQ ID NOs: 24, 25, 28, 30, 31, 32, 33, 34, 36, 37 and 38.

The invention also provides highly conserved immunogenic peptides from the terminal domain of HBV polymerase. These peptides may be any of the HBV polymerase peptides described above with reference to the compositions of the invention. Such peptides are typically from 15 to 60 amino acids in length comprise at least 15 contiguous amino acids of SEQ ID NO: 1 or 2 and elicit an immune response in vitro in PBMC from at least one individual chronically infected with HBV.

The peptide may be coupled to a carrier as described above. In one preferred aspect, the peptide of the invention is covalently linked to a fluorocarbon vector. The fluorocarbon vector may be as described above.

Other Components

The composition of the invention may comprise an additional immunogen. The immunogen may be a B-cell antigen. The B-cell antigen can serve to stimulate an antibody response to HBV. A pharmaceutical composition of the invention can, for example, comprise one or more fluorocarbon-linked peptides, which can stimulate a T-cell response, and a B-cell antigen.

Suitable immunogens that act as B-cell antigens include protein antigens such as hepatitis B surface antigen (HBsAg) or hepatitis B core antigen (HBcAg or HBeAg)

In one aspect, the present invention provides a composition comprising two or more peptides, such as fluorocarbon-linked peptides, further comprising an adjuvant and/or optionally a pharmaceutically acceptable carrier or excipient. The excipient may be a stabilizer or bulking agent necessary for efficient lyophilisation. Examples include sorbitol, mannitol, polyvinylpyrrolidone and mixtures thereof, preferably mannitol. Other excipients that may be present include preservatives such as antioxidants, lubricants, cryopreservatives and binders well known in the art.

An adjuvant is an agent that is able to modulate the immune response directed to a co-administered antigen while having few if any direct effects when given on its own. Such adjuvants may be capable of potentiating the immune response in terms of magnitude and/or cytokine profile. Examples of adjuvants include: natural or synthetically derived refinements of natural components of bacteria such as Freund's adjuvant & its derivatives, muramyldipeptide (MDP) derivatives, CpG, monophosphoryllipid A; other known adjuvant or potentiating agents such as saponins, aluminium salts and cytokines; oil in water adjuvants, water-in-oil adjuvants, immunostimulating complex (ISCOMs), liposomes, formulated nano and microparticles; bacterial toxins and toxoids; inulin, particularly gamma inulin; and TLR agonists.

Preferably, the adjuvant may be selected from the group consisting of: Peptidoglycan (such as TDM, MDP, muramyl dipeptide, Murabutide); alum solution (such as aluminium hydroxide, ADJUMER™ (polyphosphazene) or aluminium phosphate gel); glucans; algammulin; surfactants (such as squalane, Tween 80, Pluronic or squalene); calcium phosphate gel; bacterial toxins or toxoids (such as cholera holotoxin, cholera-toxin-Al-protein-A-D-fragment fusion protein, sub-unit B of the cholera toxin, or block copolymers); cytokine-containing liposomes; water-in-oil adjuvants (such as Freund's complete adjuvant, Freund's incomplete adjuvant or Montanide such as ISA 51 or ISA 720); oil-in-water adjuvants (such as MF-59); inulin-based adjuvants; cytokines (such as interferon-gamma; interleukin-lbeta; interleukin-2; interleukin-7 or interleukin-12); ISCOMs (such as iscomatrix); microspheres and microparticles of any composition; and Toll-like receptor agonists (such as CpG, ligands of human TLR 1-10, ligands of murine TLR 1-13, ISS-1018, IC31, Imidazoquinolines, Poly (I:C), Monophosphoryllipid A, Ribi529, cholera toxin, heat-labile toxin, Pam3Cys or Flagellin).

Preparation of Pharmaceutical Compositions

The pharmaceutical compositions of the invention can be prepared by solubilising at least one peptide, such as a fluorocarbon-linked peptide, in acetic acid or in other solvents as a first step in formulating a pharmaceutical product. Examples of other solvents that may be used to disperse one or more of the fluorocarbon-linked peptides in the blend include phosphate buffered saline (PBS), propan-2-01, tert-butanol, acetone and other organic solvents. Approaches for solubilising fluorocarbon vector-peptide conjugates are described in WO2012/090002.

The peptide or fluorocarbon-linked peptide used as a starting material is typically desiccated. Peptides and fluorocarbon-linked peptides that comprise peptides shorter than 20 amino acids and/or that have fewer than 50% hydrophobic residues can be solubilised in a solvent other than acetic acid. Acetic acid is typically used where the peptide has more than 20 amino acids and/or has more than 50% hydrophobic residues.

The concentration of fluorocarbon-linked peptide in the solution typically is from about 0.1 mM to about 10 mM, such as about 0.5 mM, 1 mM, 2 mM, 2.5 mM or 5 mM. An example of a suitable concentration is about 10 mg/mL.

The input components may be blended homogenously together to the desired ratios with any aggregates dispersed, rendered sterile and presented in a suitable format for administration. Such examples could include the introduction of a vortexing and/or sonication post-blending or post-dilution stage to facilitate solubilisation. Other permutations of the manufacturing process flow could include sterile filtration being performed at an earlier stage of the process or the omission of lyophilisation to permit a liquid final presentation.

Where the different peptides or fluorocarbon-linked peptides are solubilised separately, for example in different solvents or in different concentrations of acetic acid, the solubilised peptides or fluorocarbon-linked peptides are blended to create a mixture of peptides or fluorocarbon-linked peptides.

The optional adjuvant and/or one or more pharmaceutically acceptable excipients can also be added to the solubilised peptide/fluorocarbon-linked peptide or mixture of peptides/fluorocarbon-linked peptides. Typically, the solubilised fluorocarbon-linked peptides are mixed with the excipient and/or adjuvant.

After solubilisation and blending the solution of fluorocarbon-linked peptide(s) may be diluted. For example, the blend may be diluted in water.

The solution containing the peptides or fluorocarbon-linked peptides is preferably sterilised. Sterilisation is particularly preferred where the formulation is intended for systemic use. Any suitable means of sterilisation may be used, such as UV sterilisation or filter sterilisation. Preferably, filter sterilisation is used. Sterile filtration may include a 0.45 µm filter followed by a 0.22 µm sterilizing grade filter train.

Sterilisation may be carried out before or after addition of any excipients and/or adjuvants.

The composition of the invention may be in dried, such as lyophilized, form. The composition of the invention may be an aqueous solution, for example an aqueous solution formed by dissolving a lyophilisate or other dried formulation in an aqueous medium. The aqueous solution is typically pH neutral.

Drying the formulation facilitates long-term storage. Any suitable drying method may be used. Lyophilisation is preferred but other suitable drying methods may be used, such as vacuum drying, spray-drying, spray freeze-drying or fluid bed drying. The drying procedure can result in the formation of an amorphous cake within which the peptides or fluorocarbon-linked peptides are incorporated.

For long-term storage, the sterile composition may be lyophilized. Lyophilisation can be achieved by freeze-drying. Freeze-drying typically includes freezing and then drying. For example, the fluorocarbon-linked peptide mixture may be frozen for 2 hours at −80° C. and freeze-dried in a freeze drying machine for 24 hours.

Pharmaceutically acceptable compositions of the invention may be solid compositions. The fluorocarbon-linked peptide composition may be obtained in a dry powder form. A cake resulting from lyophilisation can be milled into powder form. A solid composition according to the invention thus may take the form of free-flowing particles. The solid composition typically is provided as a powder in a sealed vial, ampoule or syringe. If for inhalation, the powder can be provided in a dry powder inhaler. The solid matrix can alternatively be provided as a patch. A powder may be compressed into tablet form.

The dried, for example, lyophilized, peptide or fluorocarbon-linked peptide composition may be reconstituted prior to administration. As used herein, the term "reconstitution" is understood to mean dissolution of the dried vaccine product prior to use. Following drying, such as lyophilisation, the immunogenic peptide, for example, the fluorocarbon-linked peptide product, preferably is reconstituted to form an isotonic, pH neutral, homogeneous suspension. The formulation is typically reconstituted in the aqueous phase, for example by adding Water for Injection, histidine buffer solution (such as 28 mM L-histidine buffer), sodium bicarbonate, Tris-HCl or phosphate buffered saline (PBS). The reconstituted formulation is typically dispensed into sterile containers, such as vials, syringes or any other suitable format for storage or administration.

The composition may be stored in a container, such as a sterile vial or syringe, prior to use.

Medical Uses

The invention provides the composition of the invention for use in the treatment of the human or animal body by therapy. In particular, the composition of the invention is provided for use in a method of treating or preventing HBV infection. The composition of the invention elicits an immune response that may also be useful in HBV prophylaxis. The composition of the invention is preferably for use as a therapeutic vaccine to treat individuals infected with HBV. The composition of the invention is particularly useful in the treatment of patients with persistent chronic HBV infection, but may also be used to treat immune tolerant patients or inactive chronic carriers.

The present invention provides a therapeutic vaccine as a disruptive technology for the treatment of chronic HBV (CHB). The compositions of the invention enhance antiviral T-cell responses leading to spontaneous immune control of HBV infection. This allows cessation of antiviral NUC therapy and could potentially also lead to serological cure of HBV infection. HBsAg decline is used as a predictor of long term improved clinical outcome. HBsAg levels can be linked to the number of HBV infected hepatocytes and are determined by transcriptional activity of intrahepatic cccDNA controlled by various cytokines. Treatment using a composition of the invention may lead to HBsAg loss or HBsAg seroconversion.

The peptides and compositions of the invention are particularly useful in treating NUC-treated CHB patients. The peptides also represent an affordable treatment for HBeAg-positive patients in developing countries who may not be able to afford long-term NUC treatment. Vaccination of NUC-treated, HBV-DNA suppressed, HBeAg-negative patients in particular with the peptide compositions of the invention facilitates and accelerates HBsAg clearance. HBeAg-positive patients may also be treated. The compositions of the invention may also be used to treat inactive carriers of HBV.

Hepatitis B virus (HBV) infection is a major cause of liver-related morbidity and mortality. The compositions of the invention are provided for use in the treatment of liver failure, end-stage liver disease and hepatocellular carcinoma.

The compositions of the invention are useful in the vaccination of patients with hepatitis delta (HDV), the most severe form of viral hepatitis, for whom no approved therapy is available and which only occurs as a co-infection in HBsAg-positive individuals.

The invention also provides the use of the pharmaceutical composition of the invention in the manufacture of a medicament for treating or preventing HBV infection, particularly CHB, for treating or preventing liver failure, end-stage liver disease or hepatocellular carcinoma, or for treating or preventing HDV.

Similarly, the invention provides a method of treating or preventing HBV infection in a subject in need thereof, said method comprising administering to said subject a prophylactic or therapeutic amount of a composition of the present invention.

The composition of the invention may be administered in combination with a second therapeutic or prophylactic agent. For example, the second agent may comprise a further immunogen (such as a globular antigen or a recombinant or naturally occurring antigen), to further stimulate an immune response, for example to stimulate a humoral immune response where the fluorocarbon-linked peptide stimulates a cellular immune response, to HBV. It is understood that the second agent can be a B-cell antigen. Suitable B-cell antigens include HBsAg, HBcAg and HBeAg.

In a preferred embodiment, the second agent is an agent known for use in an existing HBV therapeutic treatment. The existing HBV therapeutic agent may be an interferon, such as interferon-alpha, or NUC, such as entecavir and tenofovir. The HBV therapeutic treatment may be a treatment that blocks suppressive cell types. Agents useful in such blocking treatments include anti-PD1 blocking antibodies, anti-PD1L blocking antibodies, anti-LAG3 blocking antibodies, anti-TIM3 blocking antibodies, anti-CTLA4 blocking antibodies and cyclophosphamide.

Where a second therapeutic agent or prophylactic agent is used in conjunction with a composition of the invention, administration may be contemporaneous or separated by time. The composition of the invention may be administered before, together with or after the second therapeutic agent.

Compositions of the invention can be administered to a human or animal subject in vivo using a variety of known routes and techniques. For example, the composition may be provided as an injectable solution, suspension or emulsion and administered via parenteral, subcutaneous, oral, epidermal, intradermal, intramuscular, interarterial, intraperitoneal, intravenous injection using a conventional needle and syringe, or using a liquid jet injection system. The composition may be administered topically to skin or mucosal tissue, such as nasally, intratrachealy, intestinally, sublingually, rectally or vaginally, or provided as a finely divided spray suitable for respiratory or pulmonary administration. In a preferred embodiment, the compositions are administered intramuscularly.

The composition can be administered to a subject in an amount that is compatible with the dosage composition and that will be prophylactically and/or therapeutically effective. The administration of the composition of the invention may be for either "prophylactic" or "therapeutic" purpose. As used herein, the term "therapeutic" or "treatment" includes anyone or more of the following: the prevention of infection or reinfection; the reduction or elimination of symptoms; and the reduction or complete elimination of a pathogen. Treatment may be effected prophylactically (prior to infection) or therapeutically (following infection).

The choice of carrier, if required, is frequently a function of the route of delivery of the composition. Within this invention, compositions may be formulated for any suitable route and means of administration. Pharmaceutically acceptable carriers or diluents include those used in compositions suitable for oral, ocular, rectal, nasal, topical (including buccal and sublingual), vaginal or parenteral (including subcutaneous, intramuscular, intravenous, intradermal, transdermal) administration.

The composition may be administered in any suitable form, for example as a liquid, solid or aerosol. For example, oral formulations may take the form of emulsions, syrups or solutions or tablets or capsules, which may be enterically coated to protect the active component from degradation in the stomach. Nasal formulations may be sprays or solutions. Transdermal formulations can be adapted for their particular delivery system and may comprise patches. Formulations for injection may be solutions or suspensions in distilled water or another pharmaceutically acceptable solvent or suspending agent.

The appropriate dosage of the prophylactic or therapeutic vaccine to be administered to a patient will be determined in the clinic. However, as a guide, a suitable human dose, which may be dependent upon the preferred route of administration, may be from 1 to 1000 µg, such as about 100 µg, 200 µg or 500 µg. Multiple doses may be required to achieve an immunological or clinical effect, which, if required, will be typically administered between 2 to 12 weeks apart. Where boosting of the immune response over longer periods is required, repeat doses 1 month to 5 years apart may be applied.

The following Examples illustrate the invention.

Example 1: Assessment of Ex Vivo Immunogenicity of HBV-Derived Short Peptide Pools in Human PBMC Methods and Materials
Populations
HBV-Infected Subjects Ninety-nine subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria:

Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Healthy Control Subjects

Cryopreserved PBMC from 17 subjects were obtained from CTL Technologies. These subjects conformed to the following criteria: Good general health, Unvaccinated to HBV, HBV surface antigen-negative, HBV core antibody-negative, HIV-negative and HCV-negative Short-Term Culture of PBMC One vial of PBMC from each subject (containing $1\times10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1\times10^6$ cells/mL for a total of 11 days. Cells were stimulated with a peptide pool containing 144 overlapping HBV-derived short peptides (SEQ ID NOs: 73 to 210 and SEQ ID NOs: 214 to 219), ranging in length from 15-20 amino acids and in overlap from 10 to 13 amino acids, at a final concentration of 0.1 µg/peptide/mL On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ ELISpot assay or intracellular cytokine staining.

Human IFNγ ELISpot Assay

Ninety-six well multiscreen PVDF filter plates (Millipore) were coated overnight at 4° C. with 100 µl (1:80) of anti-human IFNγ capture mAb (R&D Systems). Plates were then blocked with PBS supplemented with 1% BSA and 5% sucrose for 2 h at 4° C. Cells were plated in triplicate wells at 5×10$^4$ PBMC/well. Final antigen concentrations used were: 22 HBV-derived short peptide pools (see below; note pool 22 could not be prepared as peptides with SEQ ID NOs: 212 and 213 could not be dispersed due to insolubility) and HIV-3 35-mer negative peptide control: 5 µg/peptide/mL; PHA positive control: 1 µg/mL. ELISpot plates were incubated for 18 h at 37° C., 5% CO$_2$ in a humidified environment. Plates were then washed and incubated with 100 µl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

TABLE 2

Identification of peptides in pools 1 to 23

| Pool | SEQ ID NOs. of short peptides in pool |
|---|---|
| 1 | 73, 74, 75, 76, 77, 78, 79 |
| 2 | 80, 81, 82, 83, 84, 85 |
| 3 | 86, 87, 88, 89, 90, 91 |
| 4 | 92, 93, 94, 95, 96, 97 |
| 5 | 98, 99, 100, 101, 102, 103, 104 |
| 6 | 105, 106, 107, 108, 109, 110 |
| 7 | 111, 112, 113, 114, 115, 116, 117 |
| 8 | 118, 119, 120, 121, 122, 123 |
| 9 | 124, 125, 126, 127, 128, 129, 130 |
| 10 | 131, 132, 133, 134, 135, 136 |
| 11 | 137, 138, 139, 140, 141 |
| 12 | 142, 143, 144, 145, 146, 147, 148 |
| 13 | 149, 150, 151, 152, 153, 154, 155, 156 |
| 14 | 157, 158, 159, 160, 161, 162, 163, 164 |
| 15 | 165, 166, 167, 168, 169, 170, 171 |
| 16 | 172, 173, 174, 175, 176, 177, 178 |
| 17 | 179, 180, 181, 182, 183, 184 |
| 18 | 185, 186, 187, 188, 189, 190 |
| 19 | 191, 192, 193, 194, 195, 196, 197 |
| 20 | 198, 199, 200, 201, 202, 203 |
| 21 | 204, 205, 206, 207, 208, 209, 210 |
| 22 | 211, 212, 213 |
| 23 | 214, 215, 216, 217, 218, 219 |

Intracellular cytokine staining assay Cells were plated in a 96 well round bottom plate at 5×10$^5$ PBMC/well with stimulation from HBV-derived peptide pools at final concentrations of 5 µg/peptide/mL. The plate was incubated at 37° C. in a 5% CO$_2$ incubator for 20 h. For the final 3 h of the assay, PMA/Ionomycin was added to respective wells and Golgi plug was added to all wells. The cells were harvested and washed with PBS+0.1% BSA (wash buffer) and stained with anti-CD3, anti-CD4 and anti-CD8 (BD Biosciences) for 30 minutes at 4° C. After another wash, the cells were fixed and permeabilised with 100 µL of BD Cytofix/Cytoperm solution for 20 minutes at 4° C., followed by two washes with 1×BD Perm/Wash solution. Finally, cells were stained with anti-IL-2-FITC, anti-IFNγ-PE and anti-TNFα PerCP-Cy5.5 (BD Biosciences) for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

The initial step in identifying regions of interest in the HBV proteome was the comparison of IFNγ ELISpot responses of PBMC from HBV-uninfected, unvaccinated healthy subjects with those from chronic HBV-infected HBeAg negative-inactive carrier subjects in sustained control phase of the disease and chronic HBV-infected HBeAg negative subjects under treatment. Following short-term culture with a library of overlapping short peptides (15-20mers overlapping by 10-13 amino acids), representing approximately 70% of the HBV proteome, PBMC were restimulated overnight with pools of these short peptides representing specific regions of interest within the HBV polymerase, core, X and surface antigens respectively. IFNγ responses to these peptide pools were then assessed using a human IFNγ ELISpot assay.

Pools representing a number of antigenic regions were found to stimulate IFNγ responses which were specific to the chronic HBV subjects. Specifically, stimulation with pools representing terminal regions of the HBV polymerase (pool 2 & pool 3) and regions of the HBV core (pools 14-17) resulted in the greatest magnitude and population coverage of IFNγ responses in the HBV-infected subjects (FIG. 1). To a lesser extent, pools 4 to 9 and pools 11 to 13 also tend to promote HBV-specific T-cell responses.

Figure 2:
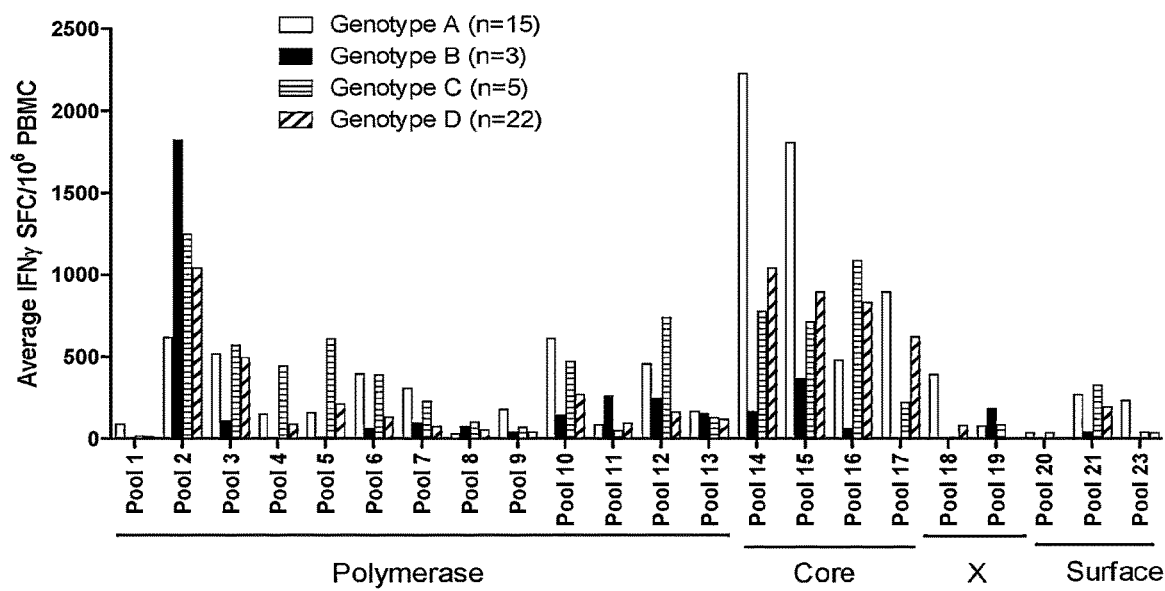
FIG. 2 shows the specificity of IFNγ responses to HBV-derived short peptide pools in HBV-infected subjects grouped by infecting HBV genotypes. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

In order to establish the role of the infecting HBV genotype on the nature of HBV-specific responses to short peptide pools, infecting HBV genotype was determined for each subject. This was determined by means of HBV surface antigen epitope assessment in plasma samples. IFNγ responses of PBMC from both immune control and treated HBV-infected subjects were subsequently grouped according to HBV genotypes A, B, C and D. Some subjects were not classified into these genotypes due to the sensitivity limitations of the assay and possible rare sera being assessed. These subjects were therefore not included in this assessment. Response profiles between the four genotypes showed similarities in that the regions showing the greatest magnitude of IFNγ responses were generally in the terminal polymerase and core regions of the HBV proteome (FIG. 2). Pools 2, 3, 10, 12, 14, 15, 16 and 17 appear to provide responses against multiple genotypes.

Figure 3:
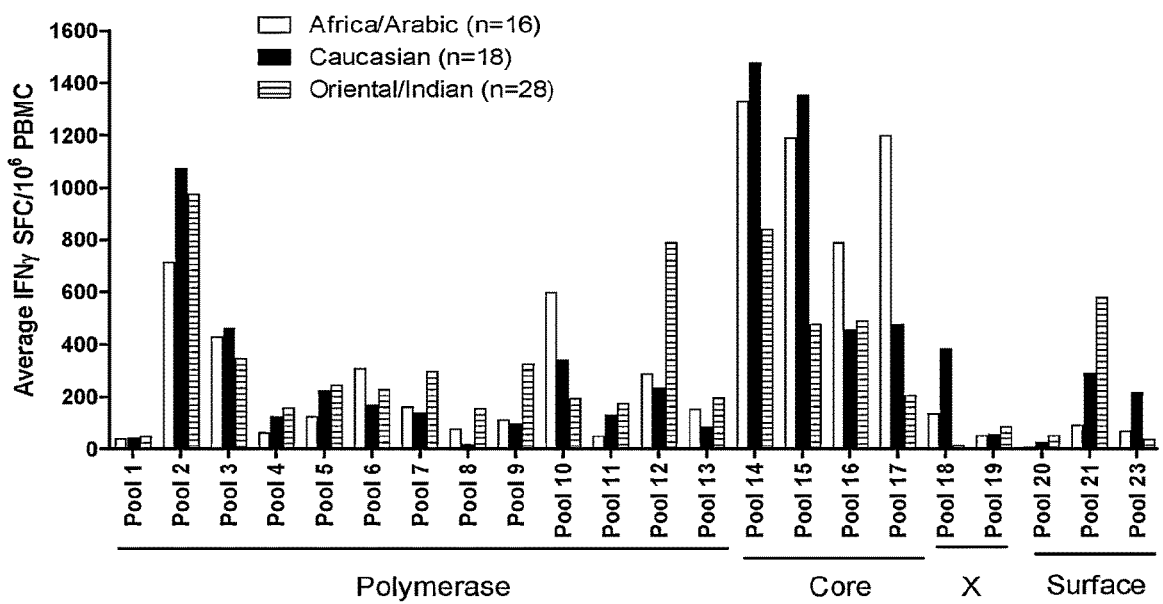
FIG. 3 shows IFNγ responses to HBV-derived short peptide pools in chronic HBV-infected subjects grouped by ethnic background. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 1 to 23 of the overlapping peptides representing specific regions of the HBV proteome.

In order to establish the role of the genetic background of the host subject on the nature of HBV-specific responses to short peptide pools, subjects in the study were grouped according their ethnicity. IFNγ responses of PBMC from both immune control and treated HBV-infected subjects were subsequently compared in three broad ethnic groups, namely African/Arabic, Caucasian and Oriental/Indian. Responses profiles between the ethnic groups showed similarities again through the greatest magnitude of IFNγ response, with associated high population coverage, being found against pools from the terminal polymerase and core regions of the HBV proteome (FIG. 3). The Caucasian group appeared to differ slightly from the other two ethnic groups in that the average magnitude of responses to a number of pools were found to be highest in the treated group of subjects, when compared to those under immune control. Pools 2, 3, 10, 14, 15, 16, 17 and 21 tend to promote responses in multiple ethnic groups.

Figure 4:
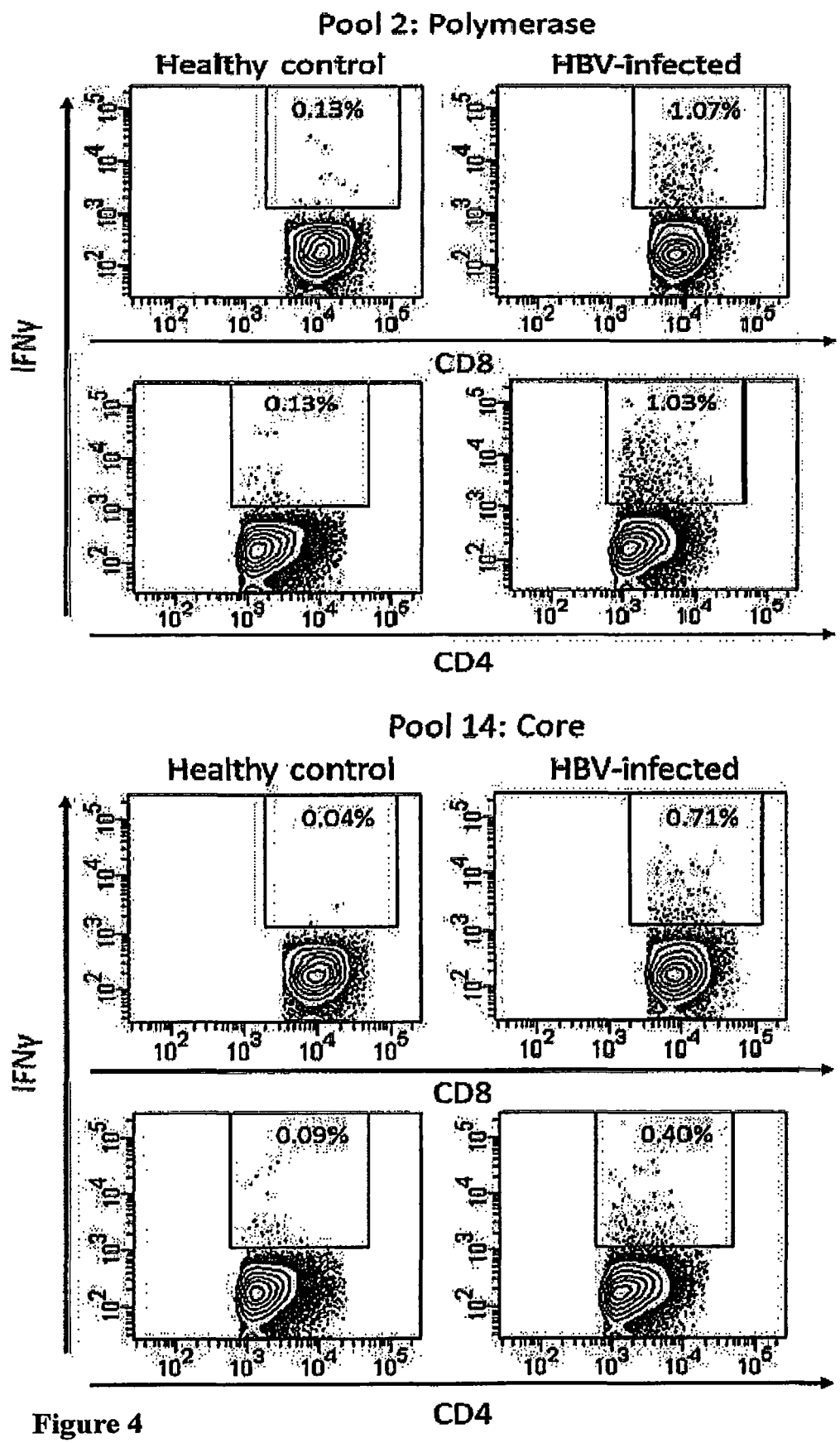
FIG. 4 shows representative dot plots of CD4 and CD8 T-cell IFNγ production in PBMC from chronic HBV and healthy control subjects following stimulation with HBV polymerase- and core-derived short peptide pools. PBMC from subjects were stimulated for 10 days with a short peptide pool library (0.1 μg/peptide/mL), followed by overnight stimulation (5 μg/peptide/mL) with HBV derived short peptide pool 2 or 14, representing regions of the HBV polymerase and core respectively. Results are expressed as IFNγ-producing cells, as a percentage of parent CD3/CD4 or CD3/CD8 T-cell populations. Stimulation in culture medium or PMA/ionomycin were used as negative and positive controls respectively and the gating strategy was based on negative control IFNγ production.

Finally, in order to further describe the type of IFNγ responses by PBMC to the short peptide pools, short-term cultured cells were restimulated overnight for intracellular cytokine staining. Cells were then assessed for CD3, CD4, CD8 and IFNγ expression by flow cytometry. A comparison was made of IFNγ responses to the short peptide pools 2 and 14 in PBMC from healthy and chronic HBV-infected subjects (FIG. 4). These were two of the peptide pools which elicited the strongest HBV-specific responses in the IFNγ ELISpot assay. Consistent with the IFNγ ELISpot assay, increased IFNγ expression was found specifically in PBMC from chronic HBV-infected subjects. Moreover, this was found to be a dual CD4 and CD8 T-cell response.

Example 2: Assessment of Ex Vivo Immunogenicity of HBV-Derived Desigen-Associated Short Peptide Pools in Human PBMC Methods and Materials
Populations
HBV-Infected Subjects 104 subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria: Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Healthy Control Subjects

Cryopreserved PBMC from 17 subjects were obtained from CTL Technologies. These subjects conformed to the following criteria: Good general health, Unvaccinated to HBV, HBV surface antigen-negative, HBV core antibody-negative, HIV-negative and HCV-negative Short-Term Culture of PBMC One vial of PBMC from each subject (containing $1 \times 10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1 \times 10^6$ cells/mL for a total of 11 days. Cells were stimulated with a peptide pool containing 144 overlapping HBV-derived short peptides (SEQ ID NO: 73 to 210 and SEQ ID NO: 142 to 147), ranging in length from 15-20 amino acids and in overlap from 10 to 13 amino acids, at a final concentration of 0.1 μg/peptide/mL. On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ ELISpot assay or intracellular cytokine staining.

Human IFNγ ELISpot Assay 96 well multiscreen PVDF filter plates (Millipore) were coated overnight at 4° C. with 100 μl (1:80) of anti-human IFNγ capture mAb (R&D Systems). Plates were then blocked with PBS supplemented with 1% BSA and 5% sucrose for 2 h at 4° C. Cells were plated in triplicate wells at $5 \times 10^4$ PBMC/well. Final antigen concentrations used were: 23 HBV-derived Densigen-associated short peptide pools (see below): 5 μg/peptide/mL; CEF peptide pool positive control: 1 μg/peptide/mL; PHA positive control: 1 μg/mL. ELISpot plates were incubated for 18 h at 37° C., 5% $CO_2$ in a humidified environment. Plates were then washed and incubated with 100 μl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

TABLE 3

Identification of peptides in pools 24 to 46

| Pool | SEQ ID NOs. of short peptides in pool |
|---|---|
| 24 | 74, 75, 76, 77, 78, 79 |
| 25 | 80, 81, 82, 83 |
| 26 | 86, 87, 88, 89 |
| 27 | 94, 95, 96, 97 |
| 28 | 98, 99, 100, 101 |
| 29 | 102, 103, 104 |
| 30 | 105, 106, 107, 108, 109 |
| 31 | 109, 110, 111, 112 |
| 32 | 116, 117, 118, 119 |
| 33 | 120, 121, 122, 123 |
| 34 | 137, 138, 139, 140, |
| 35 | 146, 147, 148, 149, 150 |
| 36 | 150, 151, 152, 153, 154 |
| 37 | 152, 153, 154, 155, 156 |
| 38 | 163, 164, 165, 166 |
| 39 | 169, 170, 171 |
| 40 | 172, 173 |
| 41 | 172, 173, 174, 175 |
| 42 | 176, 177, 178, 179 |
| 43 | 179, 180, 181 |
| 44 | 187, 188, 189, 190, 191 |
| 45 | 204, 205, 206, 207, 208, 209 |
| 46 | 215, 216, 217, 218 |

Intracellular Cytokine Staining (ICS) Assay

Cells were plated in a 96 well round bottom plate at $5 \times 10^5$ PBMC/well with stimulation from HBV-derived peptide pools at final concentrations of 5 μg/peptide/mL. The plate was incubated at 37° C. in a 5% $CO_2$ incubator for 20 h. For the final 3 h of the assay, PMA/Ionomycin was added to respective wells and Golgi plug was added to all wells. The cells were harvested and washed with PBS+0.1% BSA (wash buffer) and stained with anti-CD3, anti-CD4 and anti-CD8 (BD Biosciences) for 30 minutes at 4° C. After another wash, the cells were fixed and permeabilised with 100 μL of BD Cytofix/Cytoperm solution for 20 minutes at 4° C., followed by two washes with 1×BD Perm/Wash solution. Finally, cells were stained with anti-IL-2-FITC, anti-IFNγ-PE and anti-TNFα PerCP-Cy5.5 (BD Biosciences) for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

Subsequent to screening of responses to HBV-derived short peptide pools, 35-40mer regions of interest were identified. These regions were further assessed with a view to using 35-40mer peptides in a vaccine. Further assessment involved redesign of short peptide pools previously used for restimulation following short-term culture. Terminal short peptides extending beyond the 35-40mer regions of interest were removed from pools in order to more accurately reflect the peptides that would be used in a vaccine. Following short-term culture with the peptide library, as before, these short peptide pools were then used for restimulation in human IFNγ ELISpot and ICS assays.

Figure 5:
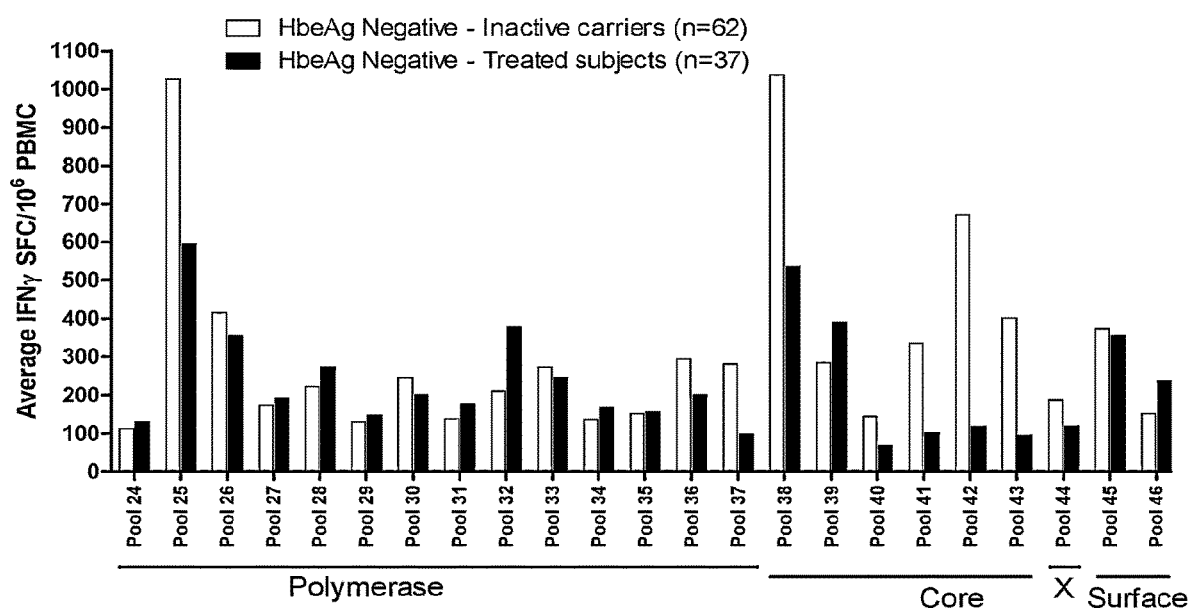
FIG. 5 is a comparison of IFNγ responses to HBV-derived short peptide pools representing 35-40mer peptides in PBMC from healthy subjects and chronic HBV-infected HBeAg-negative subjects in immune control phase or undergoing active treatment. Following a 10 day culture with an HBV-derived overlapping short peptide pool library (0.1 μg/peptide/mL), PBMC were restimulated (5 Ilg/peptide/mL) in an 18 h IFNγ ELISpot assay with one of pools 24 to 46 of the overlapping peptides, each representing 35-40mer regions of the HBV proteome.

Restimulation with pools 24 to 46 indicated dominant HBV-specific T-cell responses to regions from terminal polymerase (pool 25 and pool 26) and core (pools 38 and 39 and pool 41 to 43) regions of the HBV proteome (FIG. 5). An HBV-specific response was also found following stimulation with the surface region pool 45. Regions of polymerase corresponding to pool 28, pool 32, pool 33, pool 36 and pool 37 also gave a significant T-cell response.

Figure 6:
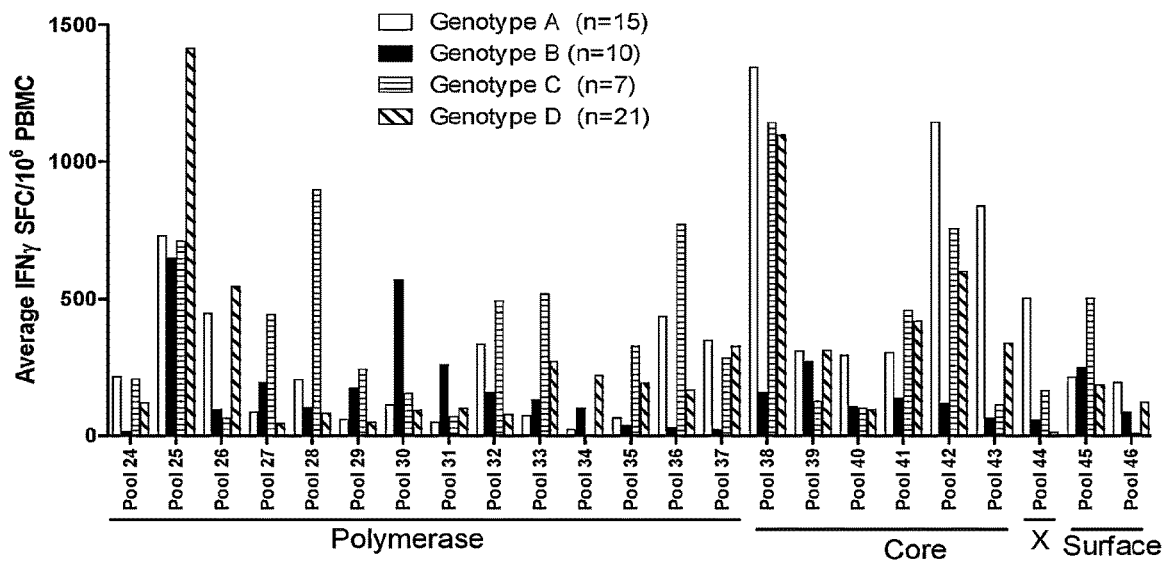
FIG. 6 shows the specificity of IFNγ responses to HBV-derived short peptide pools representing 35-40mer peptides in HBV-infected subjects grouped by infecting HBV genotype. Following a 10 day culture with an HBV-derived overlapping short peptide pool library (0.1 μg/peptide/mL), PBMC were restimulated in an 18 h IFNγ ELISpot assay with one of pools 24 to 46 of the overlapping peptides, each representing specific regions of the HBV proteome.

IFNγ ELISpot responses to pools 24 to 46 were grouped according to infecting HBV genotype (FIG. 6). Pool 27, 28, 29, 32, 35, 36 each give a predominant responses against genotype C. Pools 25 and 26 give a predominant response against genotype D. Pools 30 and 31 give a predominant response against genotype B. Pools 38, 42, 43 and 44 give a predominant response against genotype A. Some pools tend to promote responses against more than one genotype: two genotypes for pools 26, 32, 33, 36 and 43, three genotypes for pools 37, 38, 41 and 42 or even four genotypes for pool 25.

Figure 7:
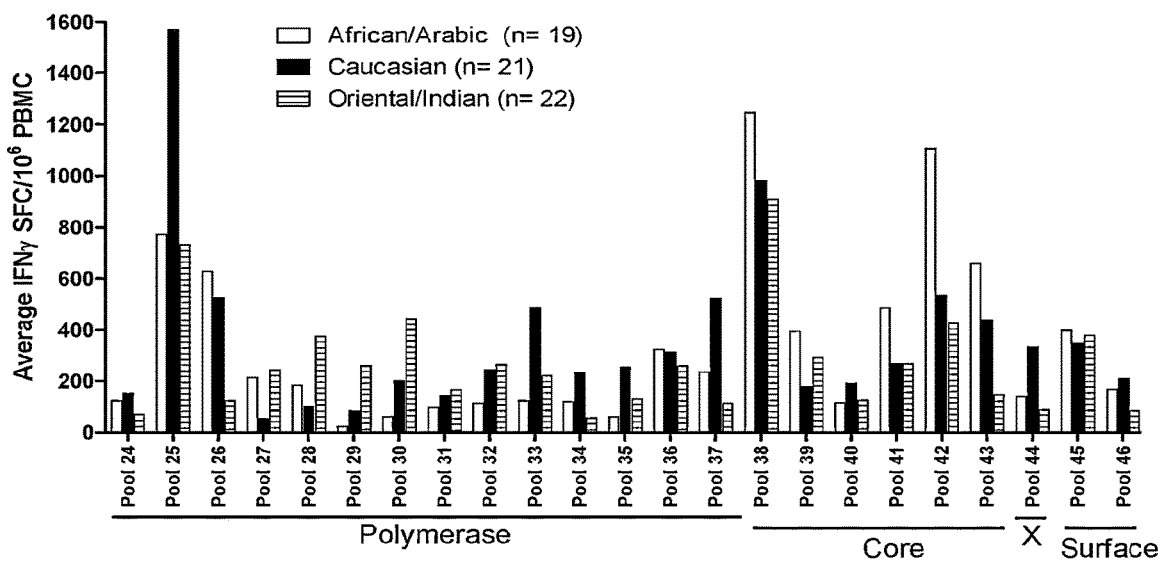
FIG. 7 shows IFNγ responses to HBV-derived short peptide pools representing 35-40mer peptides in chronic HBeAg-negative HBV-infected subjects grouped by ethnic background. Following a 10 day culture with an HBV-derived overlapping short peptide pool library (0.1 μg/peptide/mL), PBMC were restimulated (5 μg/peptide/mL) in an 18 h IFNγ ELISpot assay with one of pools 24 to 46 of the overlapping peptides, each representing 35-40mer regions of the HBV proteome.

IFNγ ELISpot responses to pools 24 to 46 were grouped according to infecting HBV genotype (FIG. 7). Pools 28, 29 and 30 give a predominant response in Oriental/Indian ethnicities. Pools 25, 33, 34, 35 and 37 give a predominant responses in Caucasian. Pools 38, 39, 41, 42 and 43 give a predominant response in African/Arabic ethnicities. Some pools tend to promote responses in more than one ethnic group: two ethnic groups for each of pools 26, 39 and 43 or three ethnic groups for each of pools 25, 38 and 42. The results are summarised in Table 4 below.

Figure 8:
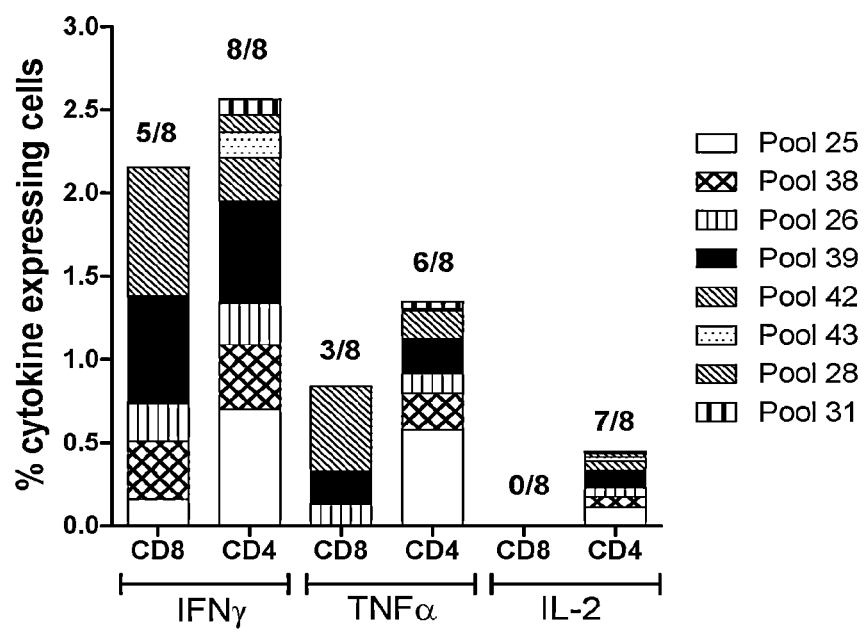
FIG. 8 is a summary of cytokine responses by PBMC from HBV-infected subjects to individual short peptide pools representing 35-40mer peptides. Following a 10 day short-term culture with an HBV-derived short peptide pool library, PBMC from chronic HBeAg-negative HBV-infected subjects (n=7-14) were cultured overnight with one of HBV peptide pools 25, 38, 26, 39, 42, 43, 28 and 31 (representing peptides P113, P753, P151, P797, P856, P877, P277 and P376) at a final concentration of 5 µg/peptide/mL. Cells were stained for extracellular expression of CD3, CD4 and CD8, followed by intracellular expression of IFNγ, IL-2 and TNFα. Cells were assessed by flow cytometry. Cytokine expression was normalized to media negative controls for each subject. Data represents mean expression for each cytokine assessed. Breadth of responses are shown above each stacked bar.

Eight pools were selected for further analysis of T-cell responses by intracellular cytokine staining. PBMC from between 7 and 14 subjects (depending on the number of cells available following the IFNγ ELISpot assay) were stimulated overnight with the one of the eight pools and cells were stained for surface CD3, CD4 and CD8 expression, together with intracellular IFNγ, TNFα and IL-2 expression (FIG. 8). IFNγ expression was found in both CD8 and CD4 T-cell populations, with a respective breadth of response to 5/8 and 8/8 of the peptide pools assessed. Similarly, TNFα expression was found in both CD8 and CD4 T-cells populations with a breadth of peptide pool response of 3/8 and 6/8 respectively. CD8 T-cells were found to express no IL-2 following peptide pool stimulation, yet CD4 T-cells expressed IL-2 following stimulation with 7 of the 8 pools.

Example 3: Construction of Fluorocarbon-Linked HBV Peptides

Peptides having the amino acid sequences shown in SEQ ID NOs: 24, 25, 28, 33, 34, 36, 37 and 38 and 222 were synthesised by FMOC (fluorenylmethyloxycarbonyl chloride) solid-phase synthesis. The fluorocarbon chain ($C_8F_{17}$ $(CH_2)_2COOH$) was then incorporated on the epsilon-chain of an additional N-terminal lysine of each peptide to derive the fluorocarbon-linked peptide. Purified fluorocarbon-linked peptides or unmodified peptides were obtained through cleavage in the presence of trifluoroacetic acid (TFA) and a final purification by reverse phase-high performance liquid chromatography (RP-HPLC). All preparations had a purity of 90% or greater.

FA-P113:
(SEQ ID NO: 24)
K(FA)-VGPLTVNEKRRLKLIMPAR

FYPNVTKYLPLDKGIK-NH2;

FA-P151:
(SEQ ID NO: 25)
K(FA)-PEHVVNHYFQTRHYLHTLW

KAGILYKRETTRSASF-NH2;

TABLE 4

Summary of predominant responses of peptides from selected regions of the HBV proteome against different HBV genotypes (A, B, C and D) and in patients of different ethnicities (OI = Oriental/Indian, C = Caucasian, AA = African/Arabic). Where a region elicits an immune response against multiple HBV genotypes or multiple ethnicities, the predominant response is indicated in bold.

| HBV proteome region | Terminal domain of polymerase | | Reverse transcriptase domain of polymerase | | | RNaseH domain of polymerase | Core protein | | | |
|---|---|---|---|---|---|---|---|---|---|---|
| Pool No. | 25 | 26 | 28 | 30 | 31 | 35 | 38 | 39 | 42 | 43 |
| Peptide | P113 | P151 | P277 | P360 | P376 | P645 | P753 | P797 | P856 | P877 |
| SEQ ID | 14 | 15 | 16 | 17 | 18 | 19 | 20 | 21 | 22 | 23 |
|  | 24 | 25 | 60 | 27 | 28 | 29 | 30 | 67 | 32 | 33 |
|  |  |  | 26 |  |  | 35 | 36 | 31 | 38 |  |
|  |  |  | 34 |  |  |  |  | 37 |  |  |
| Genotype | A B C D | A D | C | B | B | C | A C D | A B D | A C D | A D |
| Ethnicity | OI C AA | C AA | OI | OI | OI | C | OI C AA | OI AA | OI C AA | C AA |

-continued

FA-P376:
(SEQ ID NO: 28)
K(FA)-KLHLYSHPIILGFRKIPMG

VGLSPFLLAQFTSAISSVVRR-NH2;

FA-753(K):
(SEQ ID NO: 36)
K(FA)-KKKEFGATVELLSFLPSDF

FPSVRDLLDTASALYRKKK-NH2;

FA-P856(K):
(SEQ ID NO: 38)
K(FA)-LTFGRETVLEYLVSFGVWI

RTPPAYRPPNAPILSTKKK-NH2;

FA-P877:
(SEQ ID NO: 33)
K(FA)-PPAYRPPNAPILSTLPETT

VVRRRGRSPRRR-NH2;

FA-P277(K):
(SEQ ID NO: 34)
K(FA)-RVSWPKFAVPNLQSLTNLL

SSNLSWLSLDVSAAFYHKKK¬NH2;

FA-P797(K):
(SEQ ID NO: 37)
K(FA)-SPHHTALRQAILSWGELMT

LATWVGSNLEDPASRDKKK¬NH2;

FA-P1266(K):
(SEQ ID NO: 222)
K(FA)-KKKGPLLVLQAGFFLLTRI

LTIPQSLDSW WTSLNFLKKK¬NH2.

Example 4: Long HBV Peptide Formulation

A vaccine candidate, FP02.1, composed of the nine fluorocarbon-conjugated HBV-derived peptides prepared as described in Example 3 were formulated as described below. Conditions for peptide solubilization are described in Table 5. Briefly, each of the nine fluorocarbon-conjugated peptides was weighed in a 5 ml glass vial. Each peptide was then solubilised with 2 to 12% acetic acid in water solutions to achieve a peptide concentration of 10 mg. Peptide solutions (3.9 ml for each peptide) were blended in a 150 ml sterile container before 3.9 ml of 10% acetic acid solution in water was added. After stirring with a magnetic stirrer for 2 minutes, 39 mL of 9.0% mannitol in water solution was added. After stirring with a magnetic stirrer for a further 2 minutes, the solution was filtered using a 0.22 μm 33 mm Millex filter. 1.2 mL of the filtered solution was dispatched into autoclaved 2 ml glass vials. Filtration recovery measured by RP-HPLC was >95%. The vials were frozen at −80° C. for one hour. The samples were then freeze-dried for 36 hours. Freeze drying ventilation was performed under nitrogen and vial stoppering was carried out at a pressure between 400 and 600 mbar. The amount of peptide was 600 μg per peptide per vial; upon reconstitution with 1.2 mL, the final concentration was 500 μg/peptide/ml.

TABLE 5

Solubilisation conditions for preparation of FP02.1

| Peptide | Gross mass (mg) | Peptide content (%) | Net Mass (mg) | Targeted Concentration (mg/ml) | Acetic acid (%) | Volume added |
|---|---|---|---|---|---|---|
| FA-P113 | 46.54 | 86.8 | 40.40 | 20 | 2 | 4.040 |
| FA-P151 | 45.87 | 88.0 | 40.37 | 20 | 12 | 4.036 |
| FA-P277(K) | 49.76 | 81.8 | 40.70 | 20 | 4 | 4.170 |
| FA-P376 | 47.62 | 85.3 | 40.62 | 20 | 2 | 4.062 |
| FA-P797(K) | 44.69 | 92.0 | 41.11 | 20 | 2 | 4.112 |
| FA-P877 | 49.25 | 81.9 | 40.34 | 20 | 2 | 4.034 |
| FA-P753(K) | 47.47 | 85.1 | 40.40 | 20 | 2 | 4.040 |
| FA-P1266(K) | 45.82 | 86.4 | 40.45 | 20 | 2 | 4.046 |
| FA-P856(K) | 47.02 | 86.8 | 40.81 | 20 | 2 | 4.082 |

Example 5: Preferred HBV Peptides and Mixtures are Immunogenic in Chronic HBV Carriers Irrespective of the Disease Stage, the Genotype of the HBV Virus and 5 the Ethnicity of the Subjects Methods and Materials Populations 40 subjects, clinically defined as chronically HBV-infected, were enrolled into a REC-approved protocol in the Imperial Healthcare NHS Trust, the Chelsea and Westminster Hospital NHS Foundation Trust, and Barts and the London NHS Trust in London. Following written informed consent from all subjects, fresh venous blood was collected and PBMC and plasma were isolated and cryopreserved within 18 hours of blood collection. These subjects conformed to the following criteria: Good general health, HBV specific treatment: antiviral nucleos(t)ide analogue inhibitors and/or interferon therapy where clinically indicated, Clinical status (Chronic HBV infection, HBeAg-negative, and ALT normal, persistent or intermittent elevation), HIV-negative, HCV-negative and HDV-negative.

Short-Term Culture of PBMC

One vial of PBMC from each subject (containing $1 \times 10^7$ cells) was thawed and lymphocyte numbers were determined using a Scepter™ automated handheld cell counter. PBMC were cultured in 2 mL culture medium (CM: RPMI-1640 Glutamax supplemented with 5% human AB serum) in 24 well cell culture plates at a concentration of $1 \times 10^6$ cells/mL for a total of 11 days. Cells were stimulated with a mixture of the nine HBV-derived long peptides described in Example 3.

Each peptide was used at a final concentration of 1 μg/peptide/mL. On Day 4, IL-2 and IL-15 were added to the cultures to final concentrations of 10 IU/mL and 10 ng/mL respectively. On Day 10, cells were washed twice in CM and cultured with 10 IU/mL IL-2 for 1 additional day. On Day 11, cells were washed twice in CM, counted and incorporated in a human IFNγ (interferon-gamma) ELISpot assay or intracellular cytokine staining.

Human IFNγ ELISpot Assay 96 well multiscreen PVDF filter plates (Millipore) were coated overnight at 4° C. with 100 μl (1:80) of anti-human IFNγ capture mAb (R&D Systems). Plates were then blocked with PBS supplemented with 1% BSA and 5% sucrose for 2 h at 4° C. Cells from short term cultures were plated in triplicate wells at $5 \times 10^4$ PBMC/well. Final antigen concentrations used were: 5 μg/mL for each individual peptides; PHA positive control: 1 μg/mL. ELISpot plates were incubated for 18 h at 37° C., 5% $CO_2$ in a humidified environment. Plates were then washed and incubated with 100 µl (1:80) of biotinylated anti-human IFNγ detection mAb (R&D Systems) for 2 h at room temperature. Following washing, plates were incubated with a streptavidin-conjugated alkaline phosphatase (1:80) for 1 h followed by a substrate (30 min) according to the manufacturer's instructions (R&D Systems). The developed spots were counted using an automated plate counting system (CTL Europe).

Intracellular Cytokine Staining Assay (i) Cells from short-term culture were plated in a 96 well round bottom plate at 5×105 PBMC/well with stimulation from 9 HBV-derived long peptides (NP113, NP151, NP277 (K), NP376, NP753(K), NP797(K), NP856(K), NP877 and NP1266(K)) at final concentrations of 5 µg/mL. The plate was incubated at 37° C. in a 5% $CO_2$ incubator for 20 h. For the final 3 h of the assay, PMA/Ionomycin was added to respective wells and Golgi plug was added to all wells. The cells were harvested and washed with PBS+% BSA (wash buffer) and stained with anti-CD3, anti-CD4 and anti-CD8 (BD Biosciences) for 30 minutes at 4° C. After another wash, the cells were fixed and permeabilised with 100 µL of BD Cytofix/Cytoperm solution for 20 minutes at 4° C., followed by two washes with 1×BD Perm/Wash solution. Finally, cells were stained with anti-IL-2-FITC, anti-IFNγ-PE and anti-TNFα PerCP-Cy5.5 (BD Biosciences for 30 minutes at 4° C. Samples were acquired on a FACSCanto II flow cytometer (BD Biosciences). Gating was based on media stimulated samples for each subject.

Infecting HBV Genotype Determination

A nested PCR method followed by direct nucleotide sequencing was initially employed for HBV genotyping. However, due to the low viral load in plasma from the majority of samples, HBV genotype could not be determined using this method. The IMMUNIS® HBV genotype enzyme immunoassay (EIA) kit was subsequently employed. This assay used four genotype-dependent epitopes in the PreS2 region of the HBsAg, with genotypes being determined serologically by positive/negative combinations of four EIA that were specific for each of the epitopes.

Results

Figure 9:
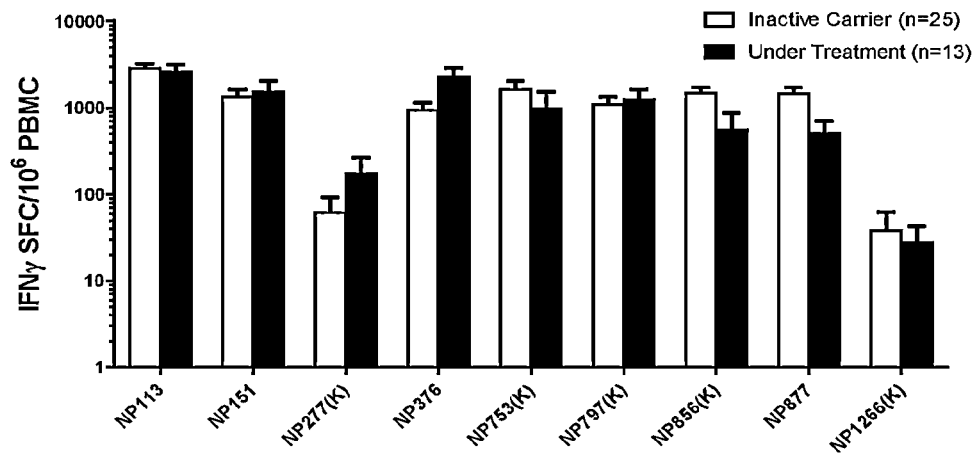
FIG. 9 shows the number of IFNγ spot forming cells (mean values) measured in PBMCs from chronic HBV-infected (either HBeAg-negative inactive carriers or HBeAg-negative treated subjects). Following a 10 day culture with the nine unconjugated HBV peptides (NP113, NP151, NP277(K), NP376, NP753(K), NP797(K), NP856 (K), NP877 and NP1266(K)) (0.1 µg/peptide/mL), PBMC were restimulated in an 18 h IFNγ ELISpot assay with individual peptides at a concentration of 5 Ilg/ml.
Figure 10:
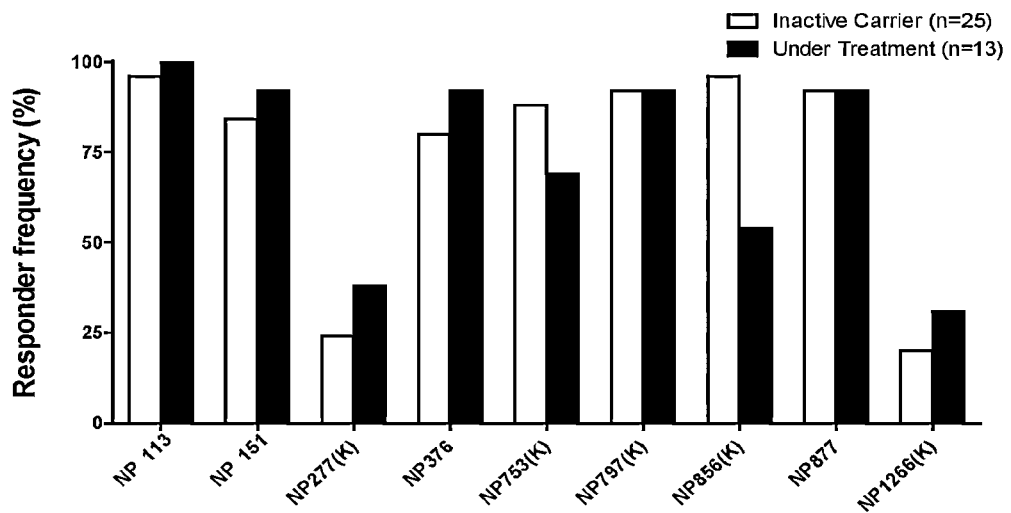
FIG. 10 shows the frequency of responders to the IFNγ ELISpot assay in response to HBV peptides measured in PBMCs from chronic HBV-infected (either HBeAg-negative inactive carriers or HBeAg-negative treated subjects). Following a 10 day culture with the nine unconjugated HBV peptides (NP113, NP151, NP277(K), NP376, NP753(K), NP797(K), NP856(K), NP877 and NP1266(K)) (0.1 µg/peptide/mL), PBMC were restimulated in an 18 h IFNγ ELISpot assay with individual peptides at a concentration of 5 µg/ml.
Figure 11:
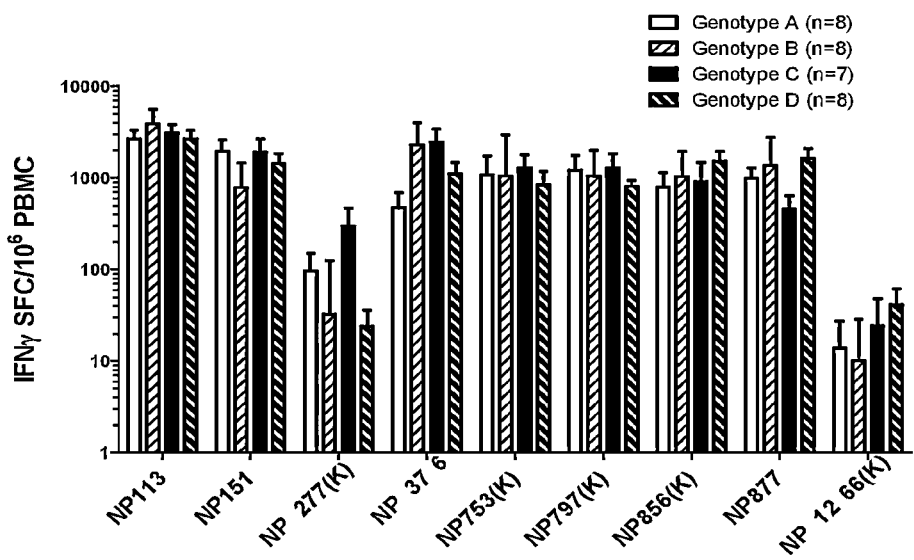
FIG. 11 shows the number of IFNγ spot forming cells (mean values) measured in PBMCs from chronic HBV-infected subjects grouped by infecting HBV genotypes. Following a 10 day culture with the nine unconjugated HBV peptides (NP113, NP151, NP277(K), NP376, NP753(K), NP797(K), NP856(K), NP877 and NP1266(K)) (0.1 µg/peptide/mL), PBMC were restimulated in an 18 h IFNγ ELISpot assay with individual peptides at a concentration of 5 µg/ml.

All peptide promoted detectable T cell responses in HBV carriers either HBeAg-negative inactive carriers and HBeAg-negative treated subjects (see FIGS. 9 and 10). Among the different peptides tested, NP113, NP151, NP376, NP753(K), NP797(K), NP856(K) and NP877 promote the highest level of responses in both patient populations and in the highest proportion of subjects. Surprisingly, the cumulative response to NP113 and NP151 is higher in both populations compared than any other combination of two peptides tested. Moreover, the cumulative response to NP113, NP151 and NP376 induces the highest level of response in both populations compared to any other combinations of three peptides tested. As shown in FIG. 11, all tested peptides promote cross-reactive T cell responses across all four HBV genotypes. Peptides NP113, NP151, NP376, NP753(K), NP797(K), NP856(K) and NP877 promote the highest responses across all four genotypes A, B, C & D compared to peptides NP2777(K) and NP1226(K). Surprisingly, NP113 promotes the highest T cell response across all four genotypes compared to all other peptides.

Figure 12:
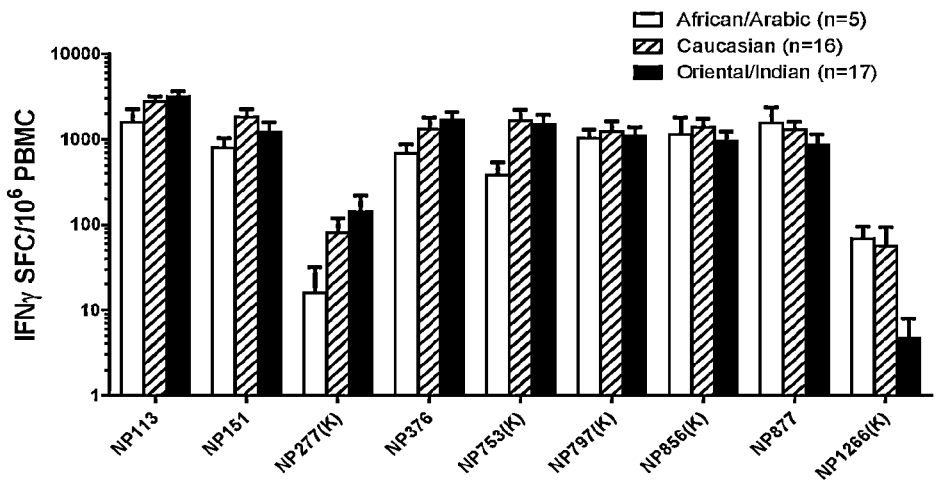
FIG. 12 shows the number of IFNγ spot forming cells measured (mean values) in PBMCs from chronic HBV-infected subjects grouped by ethnic background. Following a 10 day culture with the nine unconjugated HBV peptides (NP113, NP151, NP277(K), NP376, NP753(K), NP797(K), NP856(K), NP877 and NP1266(K)) (0.1 µg/peptide/mL), PBMC were restimulated in an 18 h IFNγ ELISpot assay with individual peptides at a concentration of 5 µg/ml.
Figure 13A:
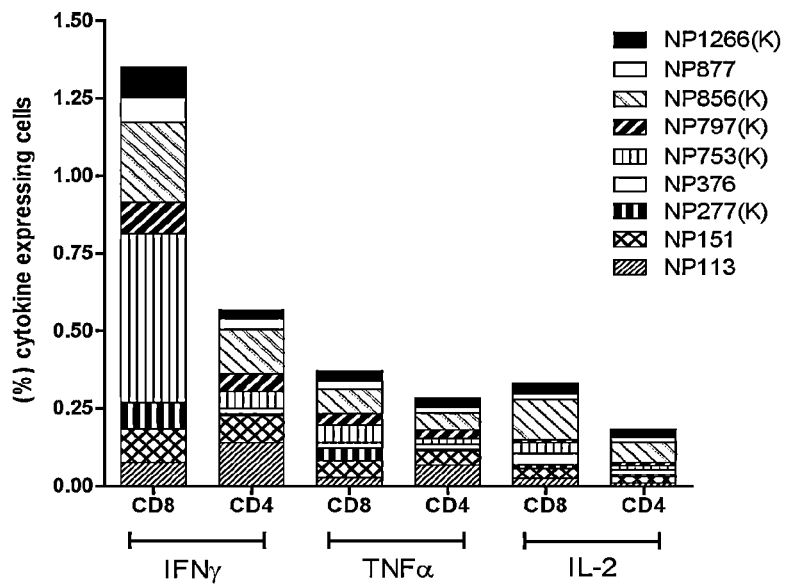
FIGS. 13A-13E show the frequency of cytokine-producing CD4+ and CD8+ T cell in PBMC from chronic HBV following stimulation with HBV derived peptides.
Figure 13B:
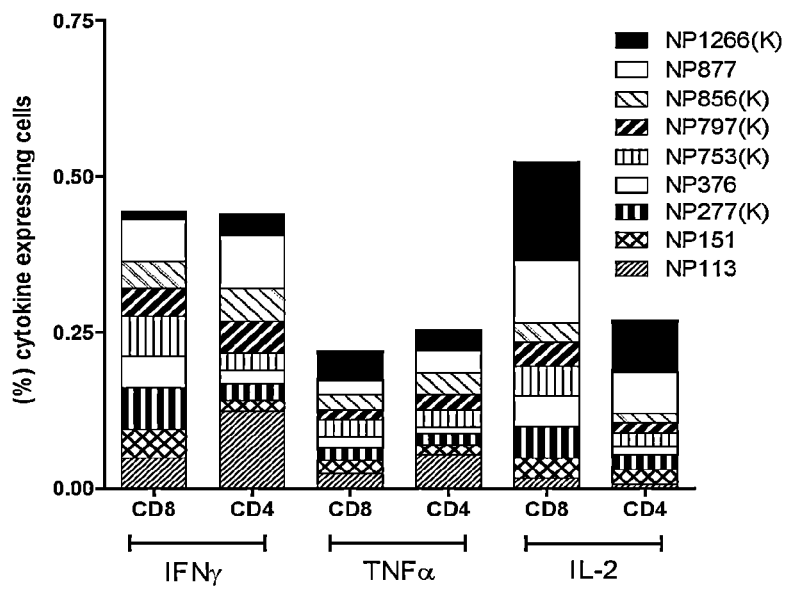
Figure 13C:
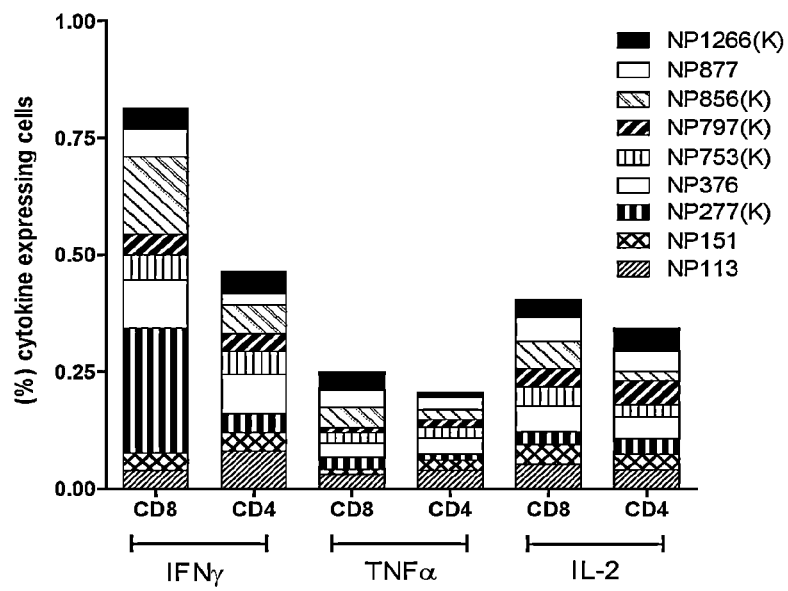
Figure 13D:
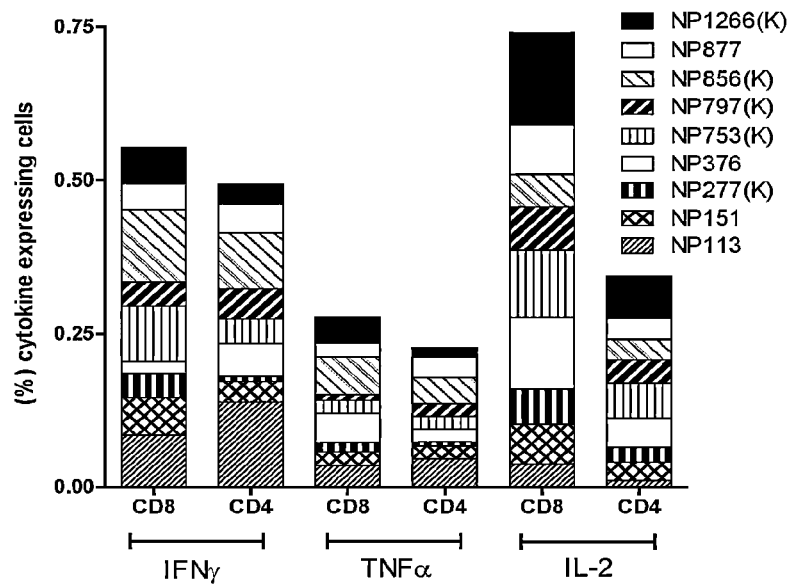
Figure 13E:
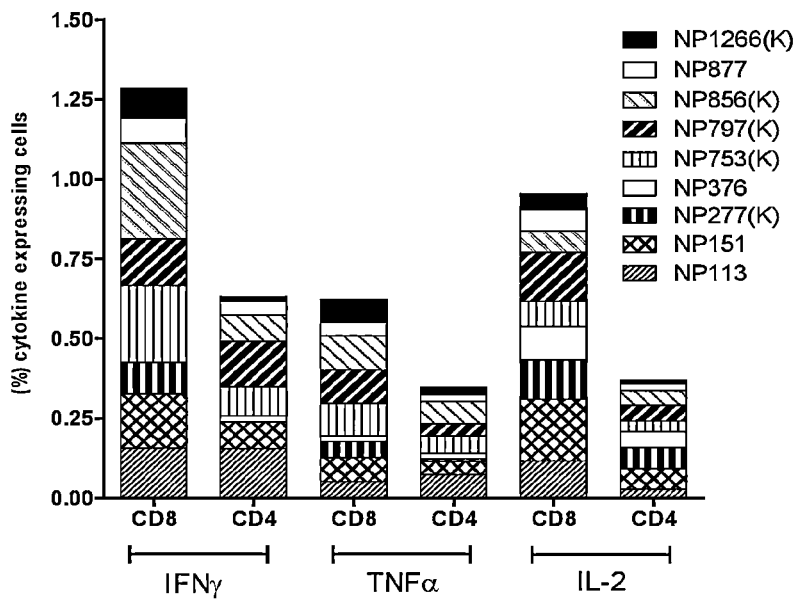

FIG. 12 shows that all peptides promote T cell responses across all ethnic groups tested. Peptides NP113, NP151, NP376, NP753(K), NP797(K), NP856(K) and NP877 promote the highest responses across all three ethnic groups compared to NP277(K) and NP1266(K).

In addition, all nine peptides show the ability to promote Th1 cytokine-producing CD4 and/or CD8 T cell responses as measured by intracellular cytokine staining across all HBV genotypes (FIGS. 13A-13E).

Example 6: Superiority of the Fluorocarbon-Conjugated Peptides Compared to Unconjugated Peptides in their Ability to Promote T Cell Responses In Vivo Methods and Materials The immunogenicity in mice of FP02.1 (containing nine fluorocarbon-conjugated peptides) was compared to NP02.1 (containing nine equivalent unconjugated peptides). Female BALB/c mice (n=7/group) were immunised intramuscularly with FP02.1 at a dose of 50 µg per peptide in a volume of 50 µL or with NP02.1 (containing the unconjugated HBV peptides (NP113, NP151, NP277(K), NP376, NP753(K), NP797(K), NP856(K), NP877 and NP1266(K)) at a equimolar dose (compared to FP02.1) of 43.8 µg per peptide in a volume of 50 µL. Mice were immunised on day 0 and sacrificed on day 14. Splenocytes were stimulated in vitro with 5 µg/mL/peptide of a mixture of each of the nine HBV peptides described in Example 3 for 18 hours in an ELISpot assay.

Alternatively, splenocytes were stimulated in vitro with 5 µg/mL/peptide of nine individual peptides for 18 hours in an ELISpot assay. The number of IFNγ+ spot forming cells (SFC) was counted. Plates then were washed with PBS, incubated with an IFNγ detection peroxidase-labelled antibody, followed by a substrate, according to the manufacturer's instructions. The developed spots were counted using an automated plate counting system (CTL Europe) to quantify the number of IFNγ+ SFCs.

Results

Figure 14:
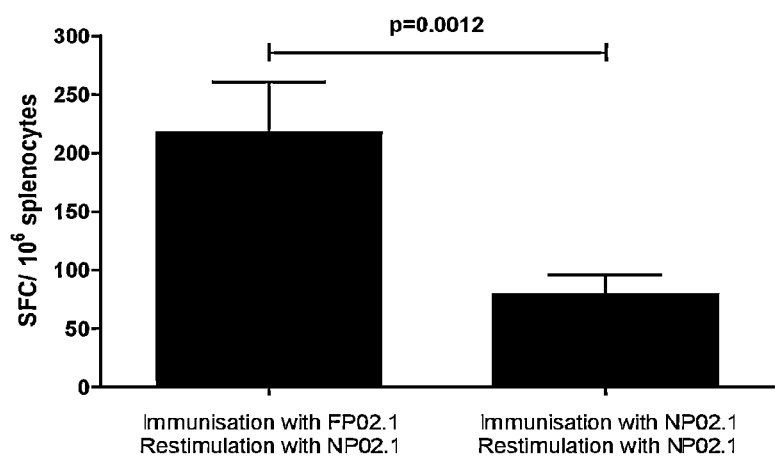
FIG. 14 shows IFNγ production by splenocytes from BALB/c mice (n=7) immunised with FP-02.1 or NP02.1. The graphic represents the number of IFNγ spot-forming cells per $10^6$ splenocytes measured in response to the 9 peptide components of the vaccines. Statistical analyses were performed using paired t tests, ns=not significant.
Figure 15:
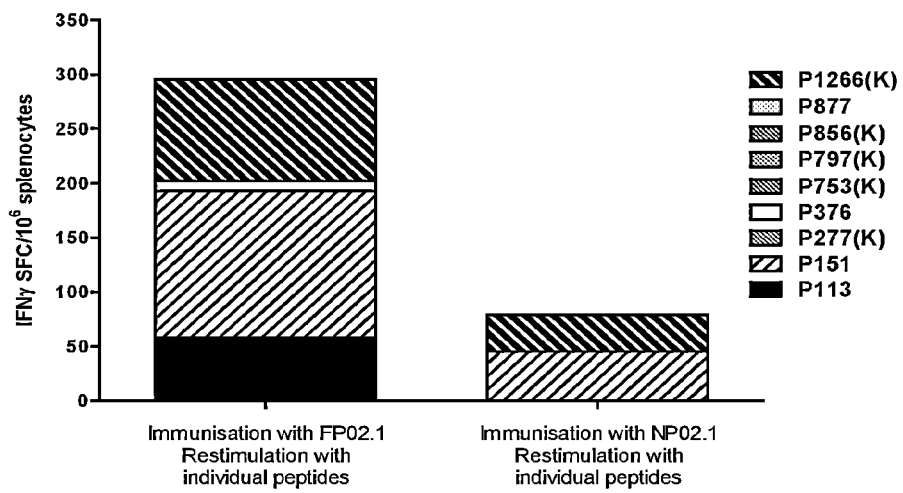
FIG. 15 shows IFNγ production by splenocytes from BALB/c mice (n=7) immunised with FP-02.1 or NP02.1. The graphic represents the number of IFNγ spot-forming cells per $10^6$ splenocytes measured in response each of the 9 peptide components of the vaccines. Bars represent cumulative median responses to each individual peptide.

Significantly higher magnitude T cell responses were observed in mice immunised with the mixture of fluorocarbon-conjugated peptides (FP02.1) compared to the equivalent mixture of unconjugated peptides (NP02.1) (see FIG. 14). Due to the MHC restriction in the syngeneic BALC/C model, immune responses were dominated by four out of the 9 peptides contained in the vaccine (peptides NP113, NP151, NP376 and NP1266(K); see FIG. 15).

Responses induced by FP02.1 were dominated by peptides NP113, NP151, NP376 and NP1266(K). Surprisingly, immune responses against peptide P113 and P376 were only observed with the formulation containing the fluorocarbon-conjugated peptides (see FIG. 15).

In conclusion, the conjugation of a fluorocarbon vector to the HBV derived peptide sequences promote higher and broader T cell responses compared to the equivalent unconjugated peptides.

Example 7: Fluorocarbon-Conjugated Peptides Promote a CTL/CD8+ T Cell Response

Methods and Materials

The quality of the immune response induced by FP02.1 (containing nine fluorocarbon-conjugated peptides) was evaluated in mice. Female BALB/c mice (n=7/group) were immunized intramuscularly with FP02.1 at a dose of 25 µg per peptide in a volume of 50 µL. Mice were immunised on day 0 and sacrificed on day 14.

Splenocytes were stimulated in vitro with either a CIL epitope derived from peptide NP113 (CTLI KYLPLDKGI) or a CTL epitope derived from NP151 (CTL 2 HYFQTRHYL) at concentrations ranging from $10^1$ to $10^{-9}$ µg/ml for 18 hours in an ELISpot assay. The number of IFNγ+ SFC was counted. Plates then were washed with PBS, incubated with an IFNγ detection peroxidase-labelled antibody, followed by a substrate, according to the manufacturer's instructions. The developed spots were counted using an automated plate counting system (CTL Europe) to quantify the number of IFNγ+ SFCs.

Results

Figure 16:
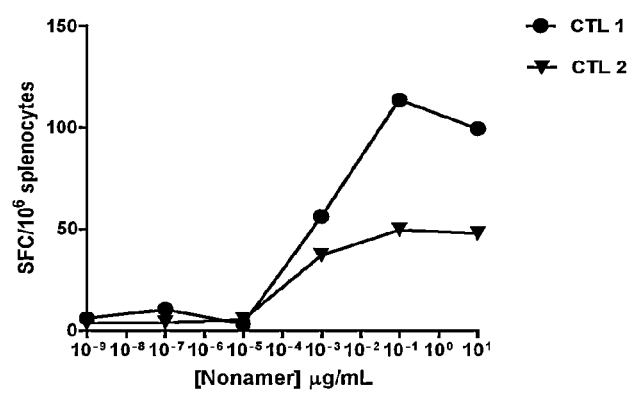
FIG. 16 shows that FP02.1 promotes T cell responses against CTL epitopes 5 restricted by MHC class I molecules after a single immunisation.

As shown in FIG. 16, FP02.1 promotes T cell responses against CTL epitopes restricted by MHC class I molecules after a single immunisation.

Example 8: Synergy Between Fluorocarbon-Peptides Contained in the Same Formulation Methods and Materials The immunogenicity of FA-P113 administered in mice alone or as part of a co-formulation with other fluorocarbon-conjugated peptides (FP02.1) was evaluated in mice. Female BALB/c mice (n=7/group) were immunised intramuscularly with FA-P113 at a dose of 25 µg or FP02.1 at a dose of 25 µg per peptide in a volume of 50 µL. Mice were immunised on day 0 and sacrificed on day 14. Splenocytes were stimulated in vitro with 5 µg/mL of NP113 (not conjugated to a fluorocarbon vector) for 18 hours in an ELISpot assay. The number of IFNγ+ SFC was counted. Plates then were washed with PBS, incubated with an IFNγ detection peroxidase-labeled antibody, followed by a substrate, according to the manufacturer's instructions. The developed spots were counted using an automated plate counting system (CTL Europe) to quantify the number of IFNγ+ SFCs.

Results

Figure 17:
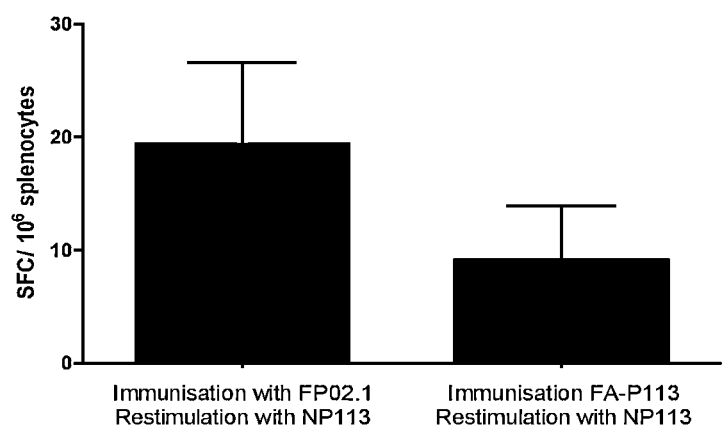
FIG. 17 shows IFNγ production by BALB/c mice immunised with FP-02.1 or NP02.1. Number of IFNγ SFC/$10^6$ splenocytes produced in response to a mixture of the nine peptides for each splenocyte population.

A higher magnitude of NP-113-specific T cell responses was observed in mice immunised with the mixture of fluorocarbon-conjugated peptides (FP02.1) than FA-P113 alone (see FIG. 17).

Example 9: Preferred HBV Peptides and Combinations Contain Epitopes Having the Ability to Bind to a Broad Range of HLA Class I Molecules Methods and Materials The ProImmune REVEAL binding assay was used to determine the ability of short peptides of nine amino-acids (derived from the HBV long peptides NP113, NP151, NP277(K), NP376, NP753(K), NP797(K), NP856(K), NP877 and NP1266(K)) to bind to one or more MHC class I alleles and stabilize the MHC-peptide complex. Detection is based on the presence or absence of the native conformation of the MHC-peptide complex. The highly frequent HLA class I alleles (HLA-A*0201, A*0301, A*1101, A*2402, B*0702, B*0801, and B*3501) were selected. Binding to MHC molecules was compared to that of a known T-cell epitope, a positive control peptide, with very strong binding properties. All potential nonamers for each HBV peptides (NP113, NP151, NP277(K), NP376, NP753 (K), NP797(K), NP856(K), NP877 and NP1266(K)) except those containing extra-lysines not present in the consensus HBV sequences were synthesised at a purity >90%. The score of the test peptide is reported quantitatively as a percentage of the signal generated by the positive control peptide, and the peptide is indicated as having a putative pass or fail result. Good binders are considered to be those peptides with scores 45% of the positive control as defined by ProImmune.

Results

The results shown in Table 6 represent the number of nonamers derived from each HBV long peptide (NP113, NP151, NP277, NP376, NP753, NP797, NP856, NP877 and NP1266) having a binding score >=45% for each HLA allele. All long HBV peptides contain at least six epitopes having the ability to bind to at least 4 alleles. Any combination of six long peptides contains nonamer epitopes having the ability to bind to all alleles tested.

TABLE 6

Number of nonamers derived from each HBV long peptide (NP113, NP151, NP277(K), NP376, NP753(K), NP797(K), NP856(K), NP877 and NP1266(K)) having a binding score >= 45% for each HLA class I alleles.

| Long peptide | HLA-A*0201 | HLA-A*0301 | HLA-A*1101 | HLA-A*2402 | HLA-B*0702 | HLA-B*0801 | HLA-B*3501 | Number of HLA binders (a) | Number of allele (b) |
|---|---|---|---|---|---|---|---|---|---|
| NP113 | 2 | 3 | 5 | 3 | 2 | 3 | 2 | 20 | 7 |
| NP797(K) | 6 | 1 | 1 | 5 | 4 | 3 | 2 | 22 | 7 |
| NP151 | 3 | 4 | 3 | 4 | 3 | 4 | 0 | 21 | 6 |
| NP376 | 8 | 0 | 1 | 10 | 4 | 6 | 6 | 35 | 6 |
| NP753(K) | 3 | 0 | 1 | 3 | 1 | 1 | 1 | 10 | 6 |
| NP1266(K) | 6 | 3 | 3 | 9 | 0 | 1 | 2 | 24 | 6 |
| NP277(K) | 6 | 0 | 0 | 5 | 3 | 1 | 3 | 18 | 5 |
| NP856(K) | 4 | 0 | 0 | 4 | 2 | 1 | 0 | 11 | 4 |
| NP877 | 2 | 0 | 0 | 2 | 1 | 1 | 0 | 6 | 4 |

(a) represents the total number binding epitopes detected for each long peptide
(b) represents the number of alleles for which positive binding was detected for each long peptide.

Example 10: Preferred HBV Peptides and Combinations Contain Epitopes Having the Ability to Bind to a Broad Range of HLA Class II Molecules Methods The ProImmune REVEAL® MHC-peptide binding assay was used to determine the ability of each HBV long peptide (NP113, NP151, NP277(K), NP376, NP753(K), NP797(K), NP856(K), NP877 and NP1266(K)) to bind one or more MHC class II allele and stabilise the MHC-peptide complex. The highly frequent HLA class II alleles HLA-DR1 (α1*01: 01;β1*01:01), HLA-DR15 (α1*01:01;β1*15:01), HLA-DR3 (α1*01:01;β1*03:01), HLA-DR4 (α1*01:01;β1*04: 01), HLA-DR11 (α1*01:01;β1*11:01), HLA-DR13 (α1*01:01;β1*13:01), and HLA-DR7 (α1*01:01;β1*07:01) were selected. Each peptide was given a score relative to the positive control peptide, which is a known T-cell epitope.

The score of the test peptide is reported quantitatively as a percentage of the signal generated by the positive control peptide, and the peptide is indicated as having a putative pass or fail result. Good binders are considered to be those peptides with scores >=15% of the positive control as defined by Proimmune.

Results

The results in Table 7 represent the binding score of each HBV long peptide (NP113, NP151, NP277(K), NP376, NP753(K), NP797(K), NP856(K), NP877 and NP1266(K)) across the range of HLA class II alleles. Six out of the nine HBV peptides bind to at least one HLA allele with a score>=15%. NP113, NP151 and NP376 bind to more than 3 different HLA class II alleles. Surprisingly, NP113 binds to a total 6 alleles.

The combination of peptides NP113 and NP877 binds to all HLA class II alleles tested.

TABLE 7

Binding of HBV peptides to a range of HLA class II molecules. Positive binding was defined as score >=15%

| Long peptide | HLA-DR1 (α1*01:01; β1*01:01) | HLA-DR15 (α1*01:01; β1*15:01) | HLA-DR3 (α1*01:01; β1*03:0) | HLA-DP4 (α1*01:03; β1*04:01). | HLA-DR11 (α1*01:01; β1*11:01) | HLA-DR13 (α1*01:01; β1*13:01) | HLA-DR7 (α1*01:01; β1*07:01) | Number of allele (a) |
|---|---|---|---|---|---|---|---|---|
| NP113 | 54.44 | 28.04 | 49.98 | 33.51 | 52.86 | 0.00 | 99.17 | 6 |
| NP151 | 14.59 | 38.96 | 0.00 | 74.36 | 49.16 | 0.00 | 19.41 | 4 |
| NP277(K) | 0.49 | 0.18 | 0.10 | 36.19 | 1.25 | 0.00 | 0.01 | 1 |
| NP376 | 27.71 | 6.29 | 0.00 | 53.66 | 31.38 | 0.00 | 8.83 | 3 |
| NP753(K) | 0.11 | 0.00 | 0.00 | 0.65 | 1.51 | 0.00 | 0.00 | 0 |
| NP797(K) | 0.20 | 1.14 | 0.00 | 6.65 | 2.86 | 0.00 | 0.01 | 0 |
| NP856(K) | 2.33 | 5.71 | 0.13 | 10.72 | 0.33 | 0.00 | 0.40 | 0 |
| NP877 | 0.24 | 0.09 | 5.58 | 0.04 | 4.98 | 16.34 | 2.78 | 1 |
| NP1266(K) | 1.48 | 0.64 | 0.00 | 11.22 | 21.64 | 0.00 | 0.62 | 1 |

(a) represents the number of alleles for which positive binding was detected for each long peptide

The invention claimed is:

1. A sterile, dried pharmaceutical composition comprising a combination of two or more fluorocarbon-linked peptide constructs, wherein each construct comprises an immunogenic hepatitis B virus peptide sequence covalently attached to a vector for intracellular delivery of the peptide, wherein the vector comprises a chain comprising from 3 to 30 carbon atoms, at least one of which is substituted with fluorine, chlorine, bromine or iodine, and wherein the peptide is from 15 to 60 amino acids in length comprising at least 15 contiguous amino acids shown in any one of SEQ ID NOs: 1 to 4 or SEQ ID No: 55 or of a sequence having at least 90% identity to one of the sequences shown in SEQ ID NOs: 1 to 4 or SEQ ID NO: 55 wherein each peptide comprises at least one CD8+ T-cell epitope and at least one CD4+ T-cell epitope and wherein the peptide binds two or more HLA class 1 alleles; and wherein the mixture is in a solid form.

2. The composition of claim 1, wherein at least one of the peptides comprises a sequence shown in one of SEQ ID NOs: 24 to 29 and at least a second peptide comprises a sequence shown in one of the SEQ ID Nos: 30 to 33.

3. The composition of claim 1, wherein at least one peptide further comprises one or more additional amino acid at the N-terminus and/or C-terminus to increase the net positive charge and/or to reduce hydrophobicity of the peptide.

4. The composition of claim 1, which comprises a peptide comprising a sequence shown in one of SEQ ID NOs: 34 to 38.

5. The composition of claim 1, wherein the composition is capable of eliciting an immune response in PBMC from at least two individuals of different ethnicities and from two individuals infected with different HBV genotypes.

6. The composition of claim 5, wherein the composition is capable of eliciting an immune response in PBMC from two, three or all of: an individual infected with HBV genotype A, an individual infected with HBV genotype B, an individual infected with HBV genotype C and an individual infected with HBV genotype D.

7. The composition of claim 5, wherein the composition is capable of eliciting an immune response in PBMC from two, three or all of: an Oriental or Indian individual infected with HBV, a Caucasian individual infected with HBV and an African or Arabic individual infected with HBV.

8. The composition of claim 1, wherein the vector is a fluorocarbon chain having the structure $C_mF_n—C_yH_x(Sp)$-R, where m=3 to 30, n<=2m+1, y=0 to 15, x<=2y, (m+y)=3-30 and Sp is an optional spacer moiety and R is the peptide.

9. The composition of claim 8, wherein the fluorocarbon chain is selected from:

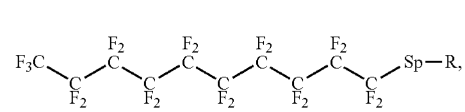

, or

.

10. The composition of claim 8, wherein the fluorocarbon chain has the formula $C_8F_{17}(CH_2)_2(Sp)$-R.

11. The composition of claim 1, which comprises from 2 to 10 said peptides.

12. The composition of claim 1, which comprises at least two of the ten peptides comprising the sequences shown in SEQ ID NOs: 24, 25, 27, 28, 33, 34, 35, 36, 37, 38, 221 and 222.

13. A method for treatment or prevention of HBV or hepatitis D virus (HDV) infection, comprising:
reconstituting the sterile dried pharmaceutical composition of claim 1 in a pharmaceutically acceptable diluent or buffer; and administering the reconstituted composition to a patient in need thereof.

14. The method of claim 13, wherein the patient is HBeAg-negative.

15. The method of claim 13, wherein the patient is HBeAg-positive.

16. A sterile, dried pharmaceutical composition comprising a combination of peptides comprising a sequence shown in each of SEQ ID NOs: 24, 25, 28, 34, 33, 36, 37, 38 and 222, wherein each peptide is attached to a fluorocarbon chain having the structure $C_mF_n—C_yH_x(Sp)$-R, where m=3 to 30, n<=2m+1, y=0 to 15, x<=2y, (m+y)=3-30, where Sp is an optional spacer moiety and R is the peptide; and wherein the mixture is in a solid form.

17. The composition of claim 16, wherein the fluorocarbon chain has the formula $C_8F_{17}(CH_2)_2(Sp)$-R.

18. The composition of claim 16, wherein the fluorocarbon chain is selected from:

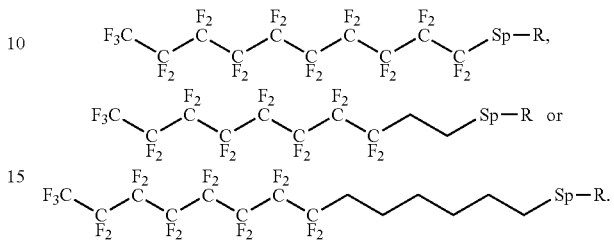

* * * * *